US008790699B2

(12) United States Patent
Lauritzen et al.

(10) Patent No.: US 8,790,699 B2
(45) Date of Patent: *Jul. 29, 2014

(54) FOAM-FORMED COLLAGEN STRAND

(75) Inventors: Nels Lauritzen, Piscataway, NJ (US); Lawrence A. Shimp, Morganville, NJ (US); Brent Mitchell, Piscataway, NJ (US)

(73) Assignee: Warsaw Orthpedic, Inc., Warsaw, IN (US)

( * ) Notice: Subject to any disclaimer, the term of this patent is extended or adjusted under 35 U.S.C. 154(b) by 276 days.

This patent is subject to a terminal disclaimer.

(21) Appl. No.: 12/766,422

(22) Filed: Apr. 23, 2010

(65) Prior Publication Data

US 2011/0262541 A1    Oct. 27, 2011

(51) Int. Cl.
| A61K 38/39 | (2006.01) |
| A61K 35/00 | (2006.01) |
| A61P 19/04 | (2006.01) |
| A61K 38/18 | (2006.01) |
| A61P 17/02 | (2006.01) |
| A61K 9/10 | (2006.01) |
| B05D 3/00 | (2006.01) |

(52) U.S. Cl.
USPC .......... 424/484; 424/93.1; 427/2.31; 514/7.6; 514/17.2

(58) Field of Classification Search
None
See application file for complete search history.

(56) References Cited

U.S. PATENT DOCUMENTS

| 3,276,448 A | 10/1966 | Kronenthal |
| 3,366,440 A | 1/1968 | Nuwayser |
| 4,060,081 A | 11/1977 | Yannas et al. |
| 4,089,333 A | 5/1978 | Utsuo et al. |
| 4,215,693 A | 8/1980 | Rothman et al. |
| 4,233,360 A | 11/1980 | Luck et al. |
| 4,440,750 A | 4/1984 | Glowacki et al. |
| 4,621,631 A | 11/1986 | Paques et al. |
| 4,642,118 A | 2/1987 | Kuroyanagi et al. |
| 4,725,671 A | 2/1988 | Chu et al. |
| 4,803,075 A | 2/1989 | Wallace et al. |
| 4,841,962 A | 6/1989 | Berg et al. |

(Continued)

FOREIGN PATENT DOCUMENTS

| WO | WO 85/05274 | 12/1985 |
| WO | WO 96/31157 | 10/1996 |

(Continued)

OTHER PUBLICATIONS

Merriam Webster's Dictionary for "Fenestrated" http://www.merriam-webster.com/medical/fenestrated (2013).*

(Continued)

*Primary Examiner* — Scott Long
*Assistant Examiner* — Sarah Alawadi
(74) *Attorney, Agent, or Firm* — Sorell Lenna & Schmidt LLP

(57) ABSTRACT

Foam-formed collagen strands and methods for forming strands involve depositing a dispersed solution of an isolated cleaned, de-fatted, enzymatically-treated (or non-enzyme treated) human-derived collagen product having a preserved amount of its natural constituents into grooves of a grooved plate, and processing the dispersed collagen product to provide a foam-formed collagen strand. Foam-formed collagen strands may be processed into threads having a matrix of reticulated pores to conduct biological materials in and through the strand, the collagen of the collagen strand comprising isolated, enzymatically-treated human derived collagen having a preserved amount of its natural collagen constituents.

19 Claims, 42 Drawing Sheets

(56) References Cited

U.S. PATENT DOCUMENTS

| | | | |
|---|---|---|---|
| 4,937,323 A | 6/1990 | Silver et al. | |
| 4,956,178 A | 9/1990 | Badylak et al. | |
| 4,963,146 A | 10/1990 | Li | |
| 5,043,426 A | 8/1991 | Goldstein | |
| 5,064,941 A | 11/1991 | Davison | |
| 5,116,389 A | 5/1992 | Mitz | |
| 5,133,755 A | 7/1992 | Brekke | |
| 5,141,747 A | 8/1992 | Scholz | |
| 5,162,430 A | 11/1992 | Rhee et al. | |
| 5,207,705 A | 5/1993 | Trudell et al. | |
| 5,282,859 A | 2/1994 | Eisenberg | |
| 5,350,583 A | 9/1994 | Yoshizato et al. | |
| 5,378,469 A | 1/1995 | Kemp et al. | |
| 5,428,022 A | 6/1995 | Palefsky et al. | |
| 5,436,135 A | 7/1995 | Tayot et al. | |
| 5,523,291 A | 6/1996 | Janzen et al. | |
| 5,532,217 A | 7/1996 | Silver et al. | |
| 5,554,389 A | 9/1996 | Badylak et al. | |
| 5,595,571 A | 1/1997 | Jaffe et al. | |
| 5,607,590 A | 3/1997 | Shimizu | |
| 5,618,312 A | 4/1997 | Yui et al. | |
| 5,658,593 A | 8/1997 | Orly et al. | |
| 5,716,411 A | 2/1998 | Orgill et al. | |
| 5,814,328 A | 9/1998 | Gunasekaran | |
| 5,837,278 A | 11/1998 | Geistlich et al. | |
| 5,855,619 A | 1/1999 | Caplan et al. | |
| 5,861,034 A | 1/1999 | Taira et al. | |
| 5,948,426 A | 9/1999 | Jefferies | |
| 5,997,895 A | 12/1999 | Narotam et al. | |
| 6,022,557 A | 2/2000 | Maser | |
| 6,057,148 A | 5/2000 | Sugiyama et al. | |
| 6,080,194 A | 6/2000 | Pachence et al. | |
| 6,179,872 B1 | 1/2001 | Bell et al. | |
| 6,277,397 B1 | 8/2001 | Shimizu | |
| 6,290,718 B1 | 9/2001 | Grooms et al. | |
| 6,391,333 B1 | 5/2002 | Li et al. | |
| 6,417,166 B2 | 7/2002 | Liu | |
| 6,440,167 B2 | 8/2002 | Shimizu | |
| 6,444,222 B1 | 9/2002 | Asculai et al. | |
| 6,455,309 B2 | 9/2002 | Stone | |
| 6,485,723 B1 | 11/2002 | Badylak et al. | |
| 6,500,464 B2 | 12/2002 | Ceres et al. | |
| 6,599,323 B2 | 7/2003 | Melican et al. | |
| 6,599,524 B2 | 7/2003 | Li et al. | |
| 6,658,626 B1 | 12/2003 | Aiken | |
| 6,682,760 B2 | 1/2004 | Noff et al. | |
| 6,685,626 B2 | 2/2004 | Wironen | |
| 6,699,287 B2 | 3/2004 | Son et al. | |
| 6,713,085 B2 | 3/2004 | Geistlich et al. | |
| 6,733,787 B2 | 5/2004 | Peterson et al. | |
| 6,752,834 B2 | 6/2004 | Geistlich et al. | |
| 6,753,311 B2 | 6/2004 | Fertala et al. | |
| 6,790,454 B1 | 9/2004 | Abdul Malak et al. | |
| 6,855,860 B2 | 2/2005 | Ruszczak et al. | |
| 6,893,462 B2 | 5/2005 | Buskirk et al. | |
| 6,893,653 B2 | 5/2005 | Abraham et al. | |
| 6,932,833 B1 | 8/2005 | Sandoval et al. | |
| 6,939,562 B2 | 9/2005 | Spiro et al. | |
| 6,977,231 B1 | 12/2005 | Matsuda | |
| 7,004,977 B2 | 2/2006 | Ashman | |
| 7,025,739 B2 | 4/2006 | Saul | |
| 7,025,742 B2 | 4/2006 | Rubenstein et al. | |
| 7,029,689 B2 | 4/2006 | Berglund et al. | |
| 7,041,868 B2 | 5/2006 | Greene et al. | |
| 7,084,082 B1 | 8/2006 | Shimizu | |
| 7,141,072 B2 | 11/2006 | Geistlich et al. | |
| 7,147,871 B2 | 12/2006 | Voytik-Harbin et al. | |
| 7,153,518 B2 | 12/2006 | Wironen et al. | |
| 7,189,221 B2 | 3/2007 | Silverberg et al. | |
| 7,201,917 B2 | 4/2007 | Malaviya et al. | |
| 7,204,825 B2 | 4/2007 | Cimino et al. | |
| 7,226,611 B2 | 6/2007 | Yura et al. | |
| 7,232,411 B2 | 6/2007 | Dinkler, II et al. | |
| 2001/0016772 A1* | 8/2001 | Lee et al. | 623/14.12 |
| 2001/0053839 A1 | 12/2001 | Noishiki et al. | |
| 2002/0103542 A1 | 8/2002 | Bilbo | |
| 2003/0114061 A1 | 6/2003 | Matsuda et al. | |
| 2004/0001877 A1 | 1/2004 | Li et al. | |
| 2004/0013712 A1 | 1/2004 | Parma | |
| 2004/0034374 A1 | 2/2004 | Zatzsch et al. | |
| 2005/0065616 A1 | 3/2005 | Ankorina-Stark et al. | |
| 2005/0100578 A1* | 5/2005 | Schmid et al. | 424/423 |
| 2005/0142161 A1 | 6/2005 | Freeman et al. | |
| 2005/0260251 A1 | 11/2005 | Hiltner et al. | |
| 2005/0267527 A1 | 12/2005 | Sandoval et al. | |
| 2005/0283256 A1 | 12/2005 | Sommerich et al. | |
| 2006/0088578 A1 | 4/2006 | Li et al. | |
| 2006/0093644 A1 | 5/2006 | Quelle et al. | |
| 2006/0147501 A1 | 7/2006 | Hillas et al. | |
| 2006/0159731 A1 | 7/2006 | Shoshan | |
| 2006/0167561 A1 | 7/2006 | Odar et al. | |
| 2006/0184098 A1 | 8/2006 | Barnitz et al. | |
| 2006/0235306 A1 | 10/2006 | Cotter et al. | |
| 2006/0252981 A1 | 11/2006 | Matsuda et al. | |
| 2006/0286144 A1 | 12/2006 | Yang et al. | |
| 2006/0293760 A1 | 12/2006 | DeDeyne | |
| 2007/0009585 A1 | 1/2007 | Morinaga et al. | |
| 2007/0021704 A1 | 1/2007 | Hariri et al. | |
| 2007/0027414 A1 | 2/2007 | Hoffman et al. | |
| 2007/0073415 A1 | 3/2007 | Sommerich et al. | |
| 2007/0088445 A1 | 4/2007 | Patel et al. | |
| 2007/0098755 A1 | 5/2007 | Patel et al. | |
| 2007/0154515 A1 | 7/2007 | Johnson et al. | |
| 2007/0161109 A1 | 7/2007 | Archibald et al. | |
| 2008/0050417 A1 | 2/2008 | Dufrane et al. | |
| 2008/0195202 A1* | 8/2008 | Lauritzen et al. | 623/11.11 |
| 2008/0213389 A1* | 9/2008 | Lelkes et al. | 424/572 |
| 2008/0260794 A1 | 10/2008 | Lauritzen et al. | |
| 2008/0280360 A1* | 11/2008 | Kaplan et al. | 435/396 |
| 2009/0306790 A1 | 12/2009 | Sun | |
| 2009/0311298 A1 | 12/2009 | Nixon et al. | |
| 2009/0312524 A1 | 12/2009 | Lauritzen | |
| 2010/0028309 A1 | 2/2010 | Odar et al. | |

FOREIGN PATENT DOCUMENTS

| | | | |
|---|---|---|---|
| WO | WO 00/35375 | | 6/2000 |
| WO | WO 2008/100967 | | 8/2008 |
| WO | WO 2011/030185 | * | 3/2011 |

OTHER PUBLICATIONS

Curtis et al. An In Vivo Microfabricated Scaffold for Tendon Repair. European Cells and Materials vol. 9, 2005. Retrieved online at http://www.ecmjournal.org/journal/papers/vol009a07.pdf.*

Zeugolis, D.I. et al. "Factors influencing the properties of reconstituted collagen fibers prior to self-assembly: Animal species and collagen extraction method," Wiley InterScience, published online Nov. 27, 2007 (www.interscience.wiley.com).

Abe et al., "Clinical Experiences with Solvent-Dried Fascia Lata in Plastic Surgery", *Jap. Journal Plast. Reconst. Surg.*, 1991, vol. 11, pp. 721-730.

Bigaré, A. et al., "Clinical Application of Human Acellular Collagen Matrix as a Dural Substitute", University Tissue Bank and Department of Neurosurgery, 1pg., 2003.

"Bioelevation™—Ptosis Slings (Brow Suspension Surgery)", *Surgeons & Med Professionals*, © 2007 IOP, Inc., 2 pp.

Brown P. et al., "Sodium Hydroxide Decontamination of Creutzfeld-Jakob Disease Virus", *The New England Journal of Medicine*, vol. 310, No. 11, 1 p., Apr. 1984.

Burres, Steven, "Preserved Particulate Fascia Lata for Injection: A New Alternative", *Dermatol Surg*, vol. 25 Oct. 1999, 790-794.

Burgeson, R. et al., "Collagen Types Molecular Structure and Tissue Distribution", Basic Science and Pathology, pp. 250-272 1991.

Derwin, K. et al., "Regional variability, processing methods, and biophysical properties of human fascia lata extracellular matrix", *Wiley Periodicals*, 2007, pp. 500-507.

Dufrane, D. et al., "Clinical application of a physically and chemically processed human substitute for dura mater", *J. Neurosurg* 98, pp. 1198-1202 (2003).

(56) References Cited

OTHER PUBLICATIONS

Dufrane, D. et al., "Physical and Chemical Processing for a human dura mater substitute", *Biomaterials 23* pp. 2979-2988 (2002).

Freytes, D. et al., "Unixial and Biaxial Properties of Terminally Sterilized Porcine Urinary Bladder Matrix Scaffolds", *Journal Biomed Mater Res Part B: Appln Biomater 84B*, pp. 408-414, 2008.

Gouk, S. et al., Alterations of human acellular tissue matrix by gamma irradiation: Histology, biomechanical property, stability, in vitro cell repopulation, and remodeling, *Journal of Biomedical Materials Research Part B: Applied Biomaterials*, 16pgs., 2007.

Guo, C. et al., Flow and Magnetic Field Induced Collagen Alignment, *Biomaterials 28* (2007), pp. 1105-1114.

Hegedus, et al., "Non-Surgical Treatment Modalities of Facial Photodamage: Practical Knowledge for the Oral and Maxillofacial Professional", *International Journal of Oral and Maxillofacial Surgery*, Copenhagen, Denmark, vol. 35, No. 5 May 1, 2006 , 389-398.

Hinton, R. et al., "A biomechanical analysis of solvent-dehydrated and freeze-dried human fascia lata allografts", *The American Journal of Sports Medicine*, vol. 20, No. 6, © 1992, pp. 607-612.

Hodde, Jason, "Naturally Occurring Scaffolds for Soft Tissue Repair and Regeneration", Tissue Engineering, vol. 8, No. 2, pp. 295-308, 2002.

Nakata, K. et al., "Reconstruction of the lateral ligaments of the ankle using solvent-dried and gamma irradiated allogenic fascia lata", *The Journal of Bone and Joint Surgery*, vol. 82-B, No. 4, May 2000, 4pgs.

Zerris, V. et al., "Repair of the Dura Mater with Processed Collagen Devices", *Journal of Biomedical Materials Research Part B: Appl Biomater* 83B: 580-588, 207, Nov. 2007.

\* cited by examiner

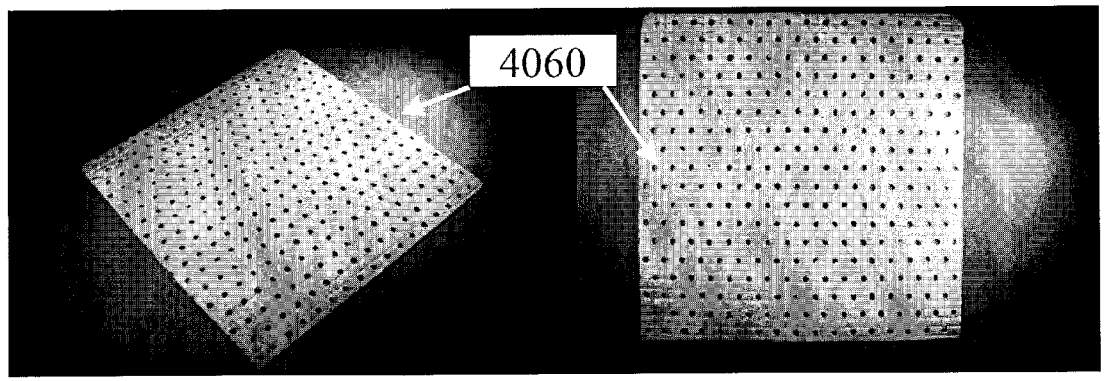
Fig. 4L     Fig. 4M
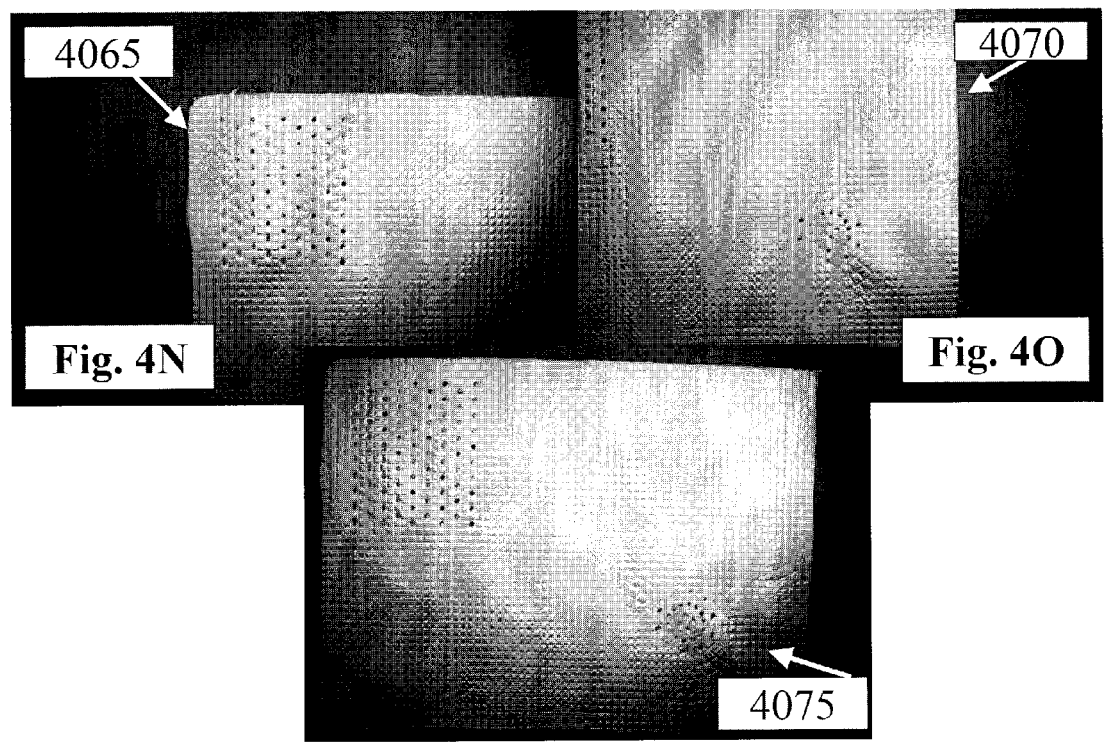
Fig. 4N     Fig. 4O
Fig. 4P

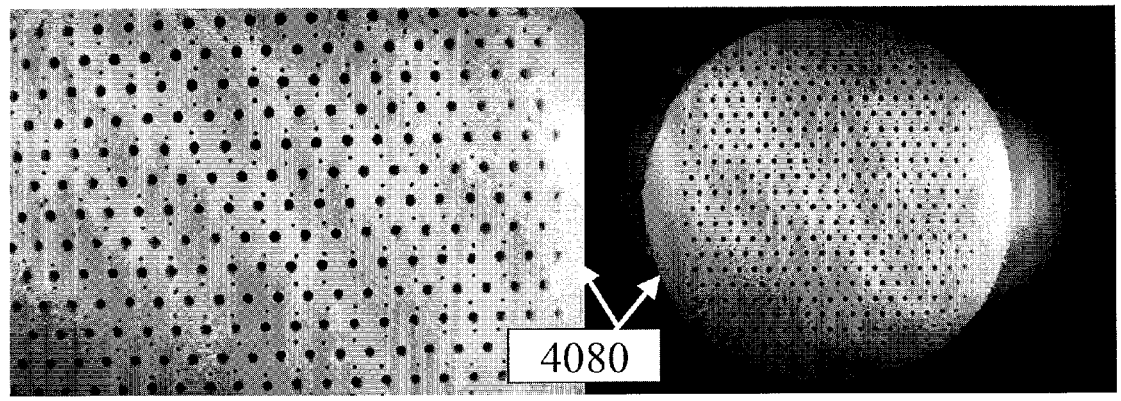
Fig. 4Q                                   Fig. 4R
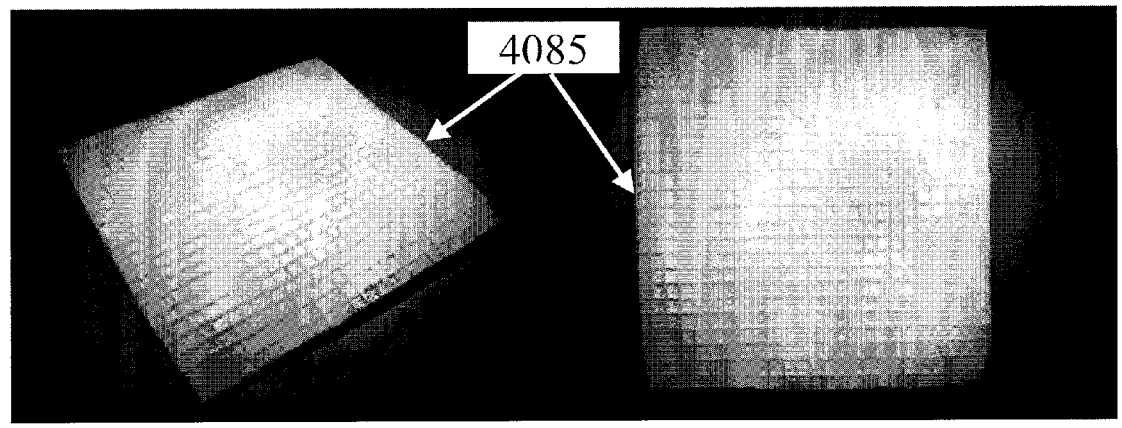
Fig. 4S                                   Fig. 4T Fig. 20A
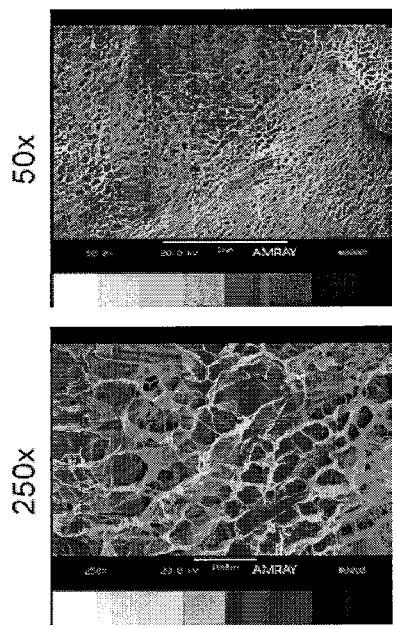
Fig. 20B
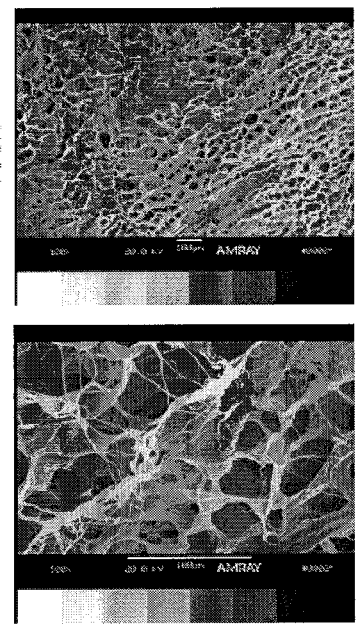
2001
Fig. 20C
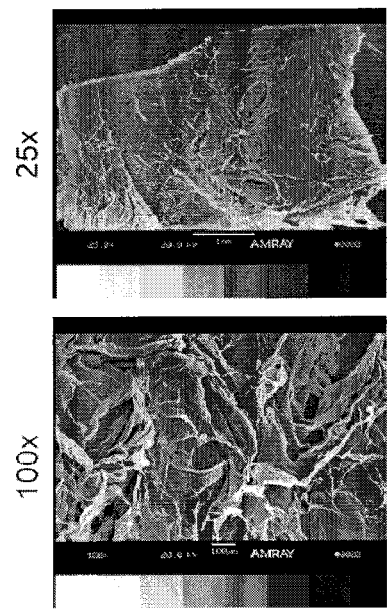
Fig. 20D
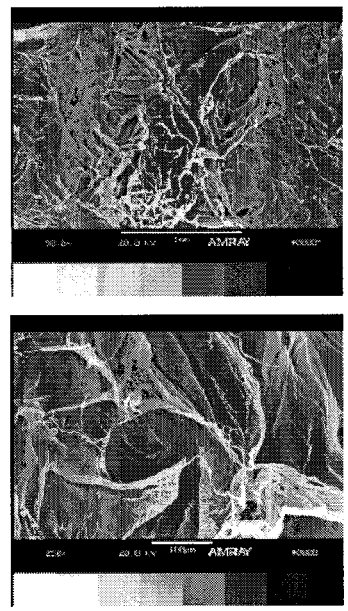
Fig. 21A
Fig. 21B
2101
Fig. 21C
Fig. 21D

FOAM-FORMED COLLAGEN STRAND

FIELD OF THE INVENTION

The invention relates generally to a method for preparing human-derived collagen fiber and/or thread base materials and collagen implants using the collagen fiber and/or thread base materials.

BACKGROUND

Collagen is used as an implant material to replace or augment hard or soft connective tissue, such as skin, tendons, cartilage, and bone. Some implants are formed as solid, flexible, or deformable collagen masses cross-linked with chemical agents, radiation, or other means to improve mechanical properties, decrease the chance of an immunogenic response, and/or to manage the resorption rate, or to improve the mechanical properties.

Collagen-based medical implants for use in humans generally have been of a non-human origin, i.e., xenogenic. A problem with the use of xenogenic tissue as a starting material when generating medical implants is that the tissue may be contaminated with viruses or prions. For example, products using bovine sourced tissue have the potential for transmitting BSE (Bovine Spongiform Encephalopathy).

Another problem with the use of xenogenic tissue is the potential for inflammation responses, hematomas, adhesions, and rejection after implantation. This is because xenogenic collagen and telopeptides can include antigens and other constituents that can initiate an immunogenic response in humans. Additionally, a certain proportion of patients can develop allergic reactions to implanted xenogeneic materials.

Thus, there is a need for methods to isolate collagen fiber and/or thread base materials for products made from the collagen fiber and/or thread base materials that are less likely to produce an immunogenic response.

SUMMARY

Various embodiments of the invention address the issues described above by providing collagen-based medical implants suitable for implantation into humans that are derived from human or human-like collagen. The collagen-based medical implants may include one or more of the following: growth factors and other non-collagenous proteins, a low immunogenicity, and desirable handling properties.

In some embodiments collagen implants may be formed from collagen products having a preserved amount of native human or human-like constituents. Such collagen products may include collagen fiber, fibrillar collagen, microfibrillar collagen, particulate collagen, collagen thread, intermediate collagen products that may or may not contain alcohol, and that may or may not be derived from a foam containing collagen and a leveling agent. Collagen implants may include collagen films, collagen coatings, collagen strands, fibers, filaments, threads and fabrics produced therefrom, foam-formed threads and fabrics produced therefrom, injectable collagen, collagen tubes, collagen plugs, collagen for in vitro applications, collagen scaffolds, fenestrated collagen scaffolds, and combinations and variations thereof. In various embodiments, fenestrated scaffolds refer to channels that pass completely through the scaffold, and/or channels that pass into, but not completely through, the scaffold.

In one embodiment, a method for forming a medical implant includes blending a dispersion of human or human-like collagen product fiber and/or thread base materials and a volume between about 2% to about 15% of an alcohol having a purity of about 70% to about 99.999%; reconstituting a foam component of the blended collagen product dispersion into a liquid phase; and removing the liquid component of the reconstituted collagen product dispersion.

In another embodiment, a method for forming a medical implant includes removing a liquid component from an intermediate collagen product to form collagen products including: collagen films, collagen coatings, collagen strands, fibers, filaments, threads and fabrics produced therefrom, collagen tubes, collagen plugs, collagen scaffolds, and collagen products for injection and in vitro applications, and combinations and variations thereof.

Other features and advantages of the invention will become apparent from the following detailed description, taken in conjunction with the accompanying drawings, which illustrate, by way of example, various features of embodiments of the invention.

DESCRIPTION OF THE DRAWINGS

FIGS. 4L-M are photographs of perspective and top views of a fenestrated patterned wound repair scaffold having a composite of fenestrations with embossed channels in accordance with certain embodiments of the present invention.

FIGS. 4N-P are photographs of top views of a fenestrated patterned wound repair scaffolds having a composite of fenestrations with embossed channels with varying fenestration and embossing patterns in accordance with certain embodiments of the present invention.

FIGS. 4Q-R are photographs of another fenestrated patterned wound repair scaffold having a combination of larger and smaller fenestrations in accordance with certain embodiments of the present invention.

FIGS. 4S-T are photographs of perspective and top views of fiber modified wound repair scaffold in accordance with certain embodiments of the present invention.

FIGS. 20A-D are scanning electron microscope (SEM) photographs of a surface of a compressed collagen product matrix provided in accordance with certain embodiments of the present invention.

FIGS. 21A-D are scanning electron microscope (SEM) photographs of another surface of a compressed collagen product matrix provided in accordance with certain embodiments of the present invention.

DETAILED DESCRIPTION

Figure 1A:
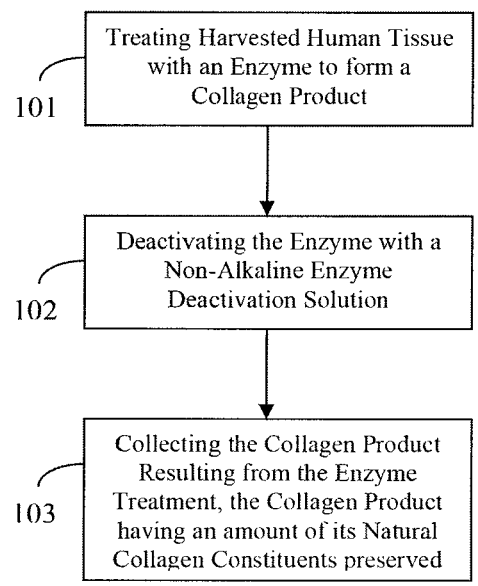
FIG. 1A depicts a method for preparing a human or human-like collagen product from harvested human or human-like tissue that may be employed according to certain embodiments of the invention.

Collagen is a connective tissue found in a variety of organisms, including humans and other mammals, aquatic species, avian species, etc. Collagen accounts for approximately 30% of the human body, and at least 26 collagen types in the human body are presently known, each adding specific function(s) to the collagen's structural role as connective tissue. For example, type I collagen found in tendons and the pericardium and represents approximately 90% of the body's total collagen content, type III collagen is found in intestines, type I or III collagen is found in fascia, i.e., tensor fascia lata, fascia lata, iliotibial band, and/or skin, type II collagen is found in cartilage and trachea, and type V collagen is found in interstitial tissue and placental tissue. In one example of the present invention, human fascia including type I collagen, type III collagen and/or elastin may be used as starting collagen material. In another example, human skin, pericardium, tendon, intestinal tissue, bladder wall tissue, placenta, etc., may be used as starting material. Collagens are described in Robert E. Burgeson and Marcel E. Nimi, *Collagen Types Molecular Structure and Tissue Distribution,* 282 Clinical Orthopaedics and Related Research 250-272 (1992), which is incorporated by reference herein in its entirety. Fascia, a collagen-containing tissue, is described in Kathleen A. Derwin et al., *Regional variability, processing methods, and biophysical properties of human fascia lata extracellular matrix,* 84 J. Biomed. Mater. Res. A 500-07 (2008); Ken Nakata et al., *Reconstruction of the lateral ligaments of the ankle using solvent-dried and gamma-irradiated allogenic fascia lata,* 82 J. Bone Joint Surg. 570-82 (2000); and Jason Hodde, *Naturally Occurring Scaffolds for Soft Tissue Repair and Regeneration,* 8 Tissue Engineering 295-308 (2002), which are herein incorporated by reference in their entireties for any purpose.

For purposes of the present invention, the following collagen-related terms are used as follows. "Collagen" is a collagen molecule, which may contain various levels of cross-linking, or a material that is made of approximately pure or native collagen fibers or molecules. In some situations, it may have a portion of the molecule removed by treatment, as in the removal of end telopeptides, etc. A "collagen product" is a medical product containing collagen, but which may also contain other extracellular matrix constituents (e.g., proteins such as noncollagenous proteins, including growth factors, bone morphogenic proteins (BMPs), etc.), but is processed to exclude cells that are naturally found in the collagen from the tissue source. Collagen products may be scaffolds, fibrils, fibers, particles, strands, matrices, sponges, foams, foam-formed fibers, etc., or any other suitable form. "Purified collagen products" are medical products containing essentially pure collagen and are largely devoid of other natural extracellular matrix components. "Collagen-containing tissue" is a tissue sourced from one of the connective tissues, such as the fascia lata, placenta, etc., which contains collagen, but which may also contain cells and other extracellular matrix components.

The present invention discloses methods for preparing human-based or human-like collagen products including fiber and/or thread base materials and for producing collagen fibers, fibrils, particles, threads, strands and other implants that use human-based or human-like collagen products, so that when implanted, no or a low immunogenic response in humans results. Human-like collagen is collagen derived from a non-human source that may be treated to result in a collagen product that is implantable and produces no or a low immunogenic response in humans. Human-like collagen may be transgenic or genetically engineered collagen and may be enzymatically treated to remove immunologically active glycoproteins and recombinant collagen. The collagen-containing medical implants provided according to some embodiments have one or more of the following attributes, including physiologically compatible, sufficiently noninfectious to prevent transmission of viruses and prions and growth of bacteria (vegetative and spores) and fungi, pliable, available for a wide variety of applications in a variety of shapes and sizes, high in tensile strength, and inert.

According to various embodiments of the invention, any of a variety of types of human connective tissue and connective tissue from other organisms including genetically engineered animals may be processed to yield human collagen products, or products that do not produce an antigenic response in humans. Collagen products provided according to some embodiments may be supplemented with cells and/or proteins such as stem cells. Accordingly, collagen products provided according to aspects of the invention may include collagen with non-collagenous proteins and/or extracellular matrix, which may or may not be supplemented with cells not naturally present in the source collagen tissue.

Preparing Collagen Fiber and/or Thread Base Materials

FIG. 1A depicts a method for preparing human-derived or human-like collagen products from harvested human or human-like collagen-containing tissue, according to certain embodiments of the invention. The method of FIG. 1A includes treating (101) harvested human or human-like collagen-containing tissue with one or more enzymes to yield a collagen product that is suitable for implantation into humans. The enzyme is deactivated (102) using a non-alkaline enzyme deactivation solution, and the collagen product resulting from the enzyme treatment is collected (103). Where the original collagen source is human, the resulting collagen product, e.g., non-immunogenic human collagen fiber, includes a preserved amount of its native human constituents, e.g. native signaling factors. Collagen products that contain a preserved amount of its native human constituents retains a sufficient or effective amount of the original collagen structure and/or constituents, including non-collagenous proteins and/or cross-link chemistries, to be suitable or therapeutically beneficial for its intended application.

Figure 1B:
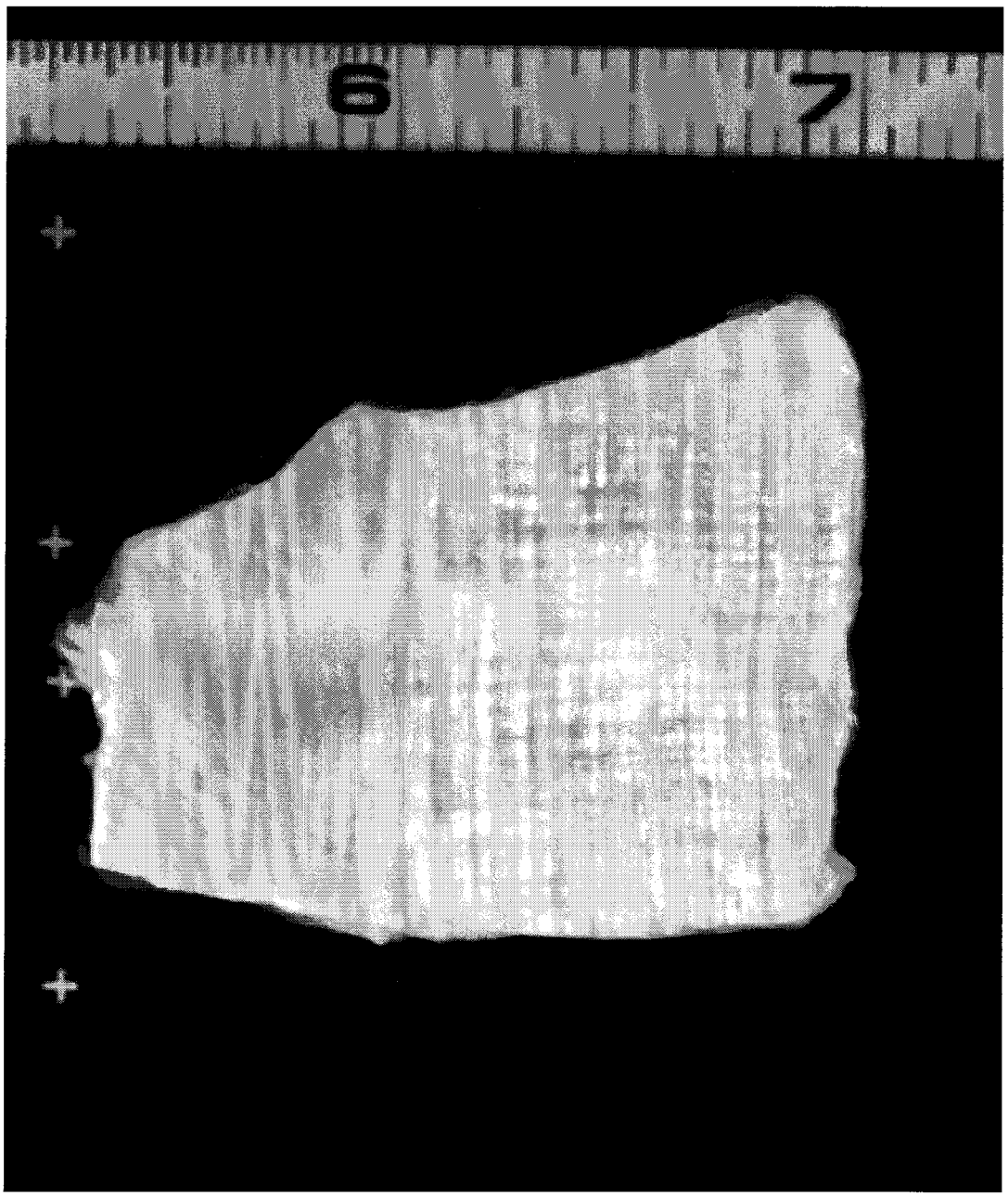
FIG. 1B is a photograph of human fascia, which may be used as a starting material for preparing a human collagen product.

FIG. 1B is a photograph of human fascia, which may be used as a starting material for preparing human collagen products according to the method of FIG. 1A. The human fascia depicted in FIG. 1B includes banded collagen evidenced by its vertical stripes that traverse the fascia sample. Collagen fibers bound in fascia are biologically manufactured as extra-cellular protein units (e.g., helical assemblies of amino acids) that are about 300,000 nanometers in length.

Figure 1C:
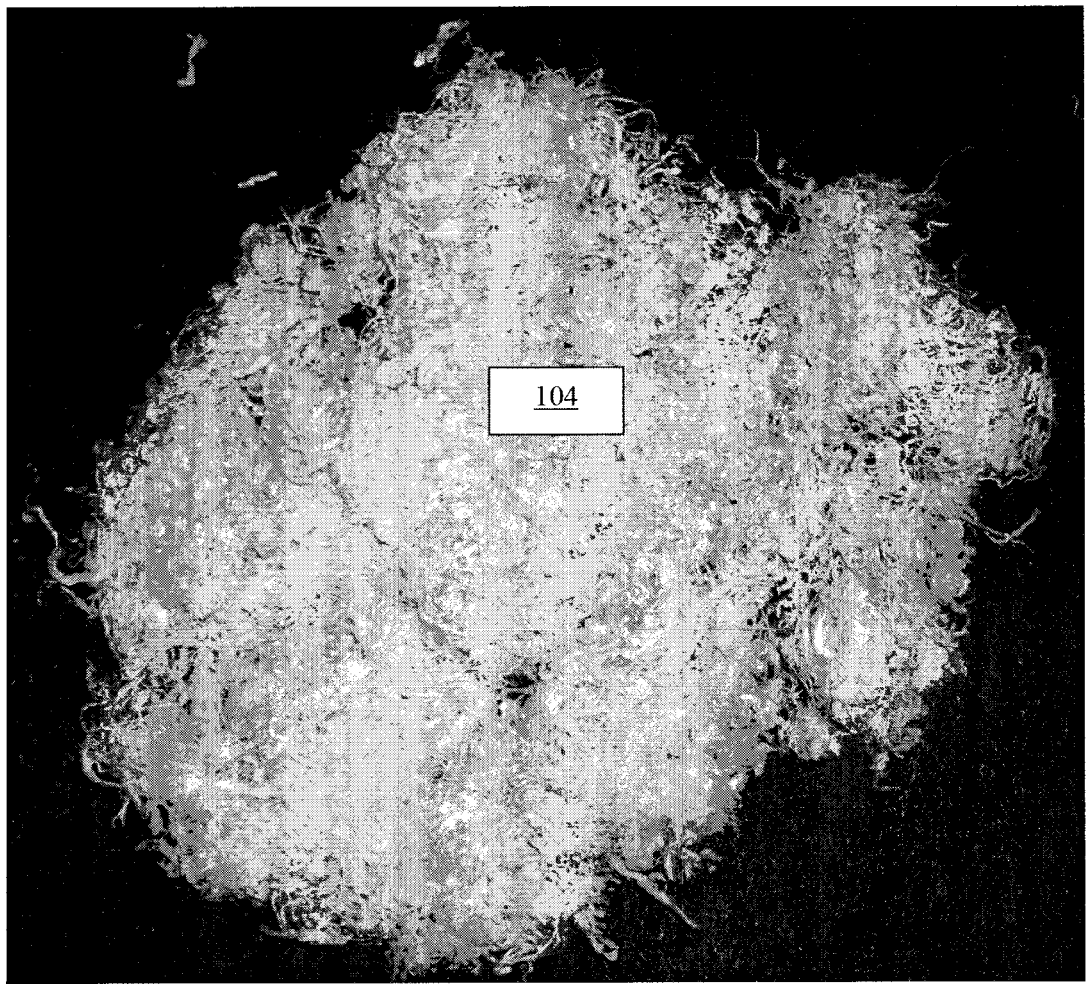
FIG. 1C is a photograph of human-derived collagen product fiber and/or thread base materials made from human fascia that is or may be prepared for use as a medical implant in accordance with certain embodiments of the present invention.

FIG. 1C is a photograph of human collagen fiber and/or thread base materials 104 that may result from processing bound collagen in human fascia according to the collagen product production method of FIG. 1A. The human collagen fibers 104 may be used as or prepared for use in a medical implant in accordance with certain embodiments of the present invention. In FIG. 1C, the prepared human collagen fiber and/or thread base materials 104 appear beige in color, have a diameter of about the diameter of a human hair to about the diameter of a plant fiber, e.g., flax, a length of about 10 cm to a particulate size such as about 50 microns, with an average length of about 3.2 cm (1.25 in., e.g., common staple fiber), are coarse to the touch like coarse cotton, hemp or hair.

Figure 1D:
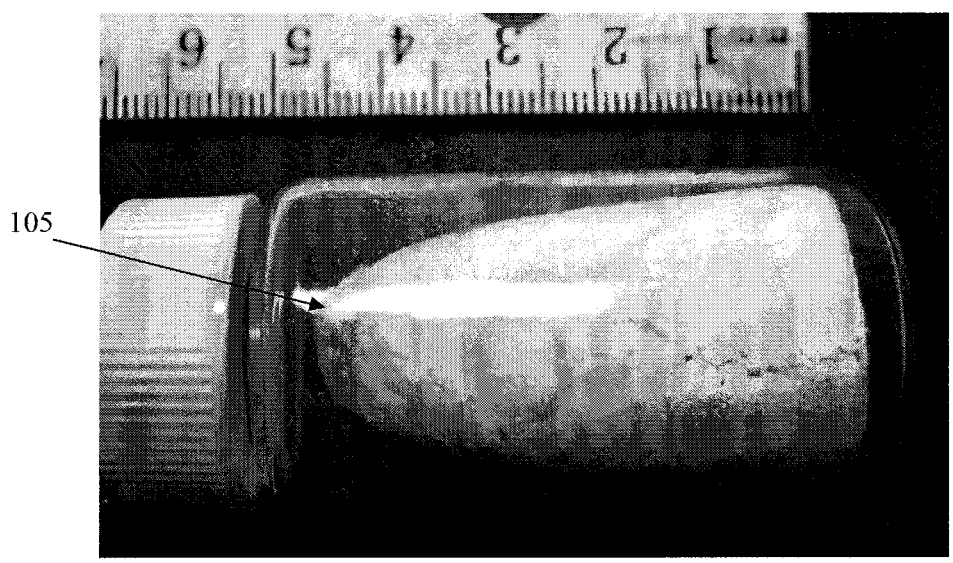
FIG. 1D is a photograph of human-derived fibrillar collagen product made from human fascia that is or may be prepared for use as a medical implant in accordance with certain embodiments of the present invention.

FIG. 1D is a photograph of prepared fibrillar collagen 105 made from milled collagen fibers like those pictured in FIG. 1C, for example. In FIG. 1D, the fibrillar collagen 105 appears like a particulate, but when viewed microscopically may be fiber-like in appearance. Accordingly, the characteristics of fibrillar collagen may be similar to the collagen fiber and/or thread base materials but for the shorter length of the individual fibrillar collagen grains and possibly smaller diameters.

The above-described method for preparing human or human-like collagen products, e.g., fiber and/or thread base materials, involves enzymatically treating (e.g., ficin treatment, treatment with a proteoglycan-depleting factor and/or glycosidase, or treatment with a mild enzyme that does not destroy all non-collagenous proteins in the human or human-like collagen) harvested human or human-like collagen-containing tissue to separate collagen fiber and/or thread base materials in tissue from other components and to break down peptide bonds between amino acids of proteins in the collagen, while retaining certain native constituents and receptivity of the human-derived or human-like collagen. For example, native constituents may include uniquely human or human-like biological characteristics, which allow the collagen product to be biocompatible. In some implementations, the enzyme treatment breaks down some of the telopeptide bonds, while leaving others intact. This results in partly bound collagen fiber and/or thread base materials retaining a portion of the native non-collagenous proteins. The fiber and/or thread base materials are non-immunogenic due to their human or human-like origins. The method of FIG. 1A and additional methods for preparing human collagen products with native human constituents preserved involving the use of enzyme treatment are described in U.S. patent application Ser. No. 11/673,972, filed Feb. 12, 2007, entitled "Methods for Collagen Processing and Products using Processed Collagen," which is incorporated by reference herein in its entirety for any relevant purpose. However, it will be understood that collagen products may be prepared using any known method.

Figure 1E:
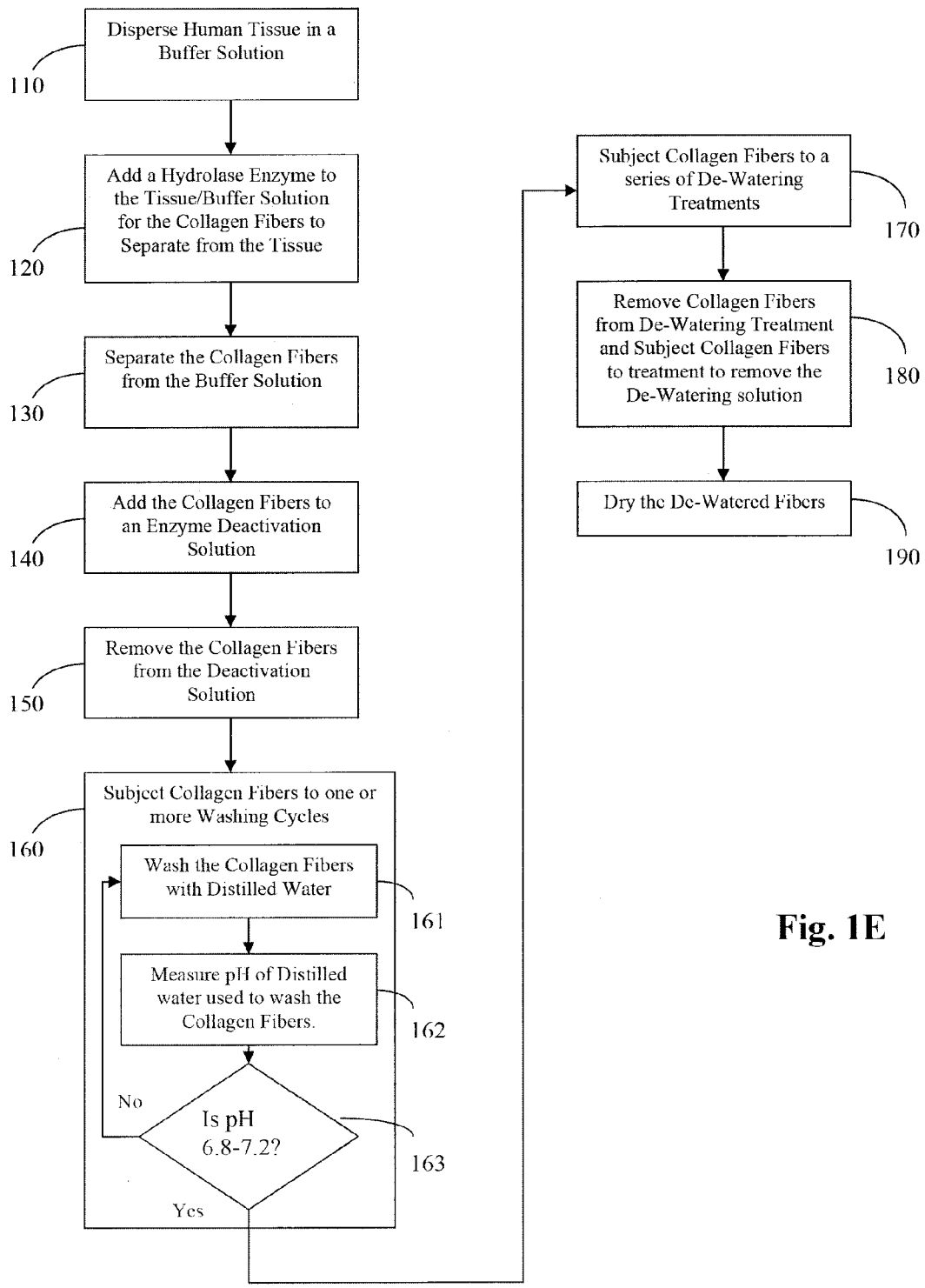
FIG. 1E depicts methods for recovering a human-derived collagen product from human tissue according to certain embodiments of the present invention.

FIG. 1E depicts a more detailed collagen product preparation method according to certain embodiments of the present invention. According to one method, finely ground or sliced human collagen-containing tissue (such as fascia, tendon, and/or small intestine submucosa) containing bound collagen is dispersed (110) in a buffer solution at a suitable temperature and pH. Any suitable buffer solution at any appropriate pH and temperature may be used for providing an environment for the efficient use of a particular enzyme to enable the enzyme to attack and remove material. In the exemplary use of ficin in a buffer solution of potassium phosphate ($KH_2PO_4$) and sodium hydroxide (NaOH), enzymatic activity is carried out efficiently at a pH of 6.3+/−0.15 and at a temperature of 37° C.+/−1.5° C. However, it will be understood that buffer solutions may be suitable at any appropriate pH, such as a pH from about 3 to about 9, from about 5 to about 7, or from about 6.0 to about 6.3. Further, buffer solutions may be suitable at any appropriate temperature such as between about 20° C. and about 50° C., between about 30° C. and about 40° C., or about 37° C. After the collagen-containing tissue is added to a buffer solution, a hydrolase enzyme is added (120). Any suitable enzyme may be used, such as hydrolase enzymes that include ficin, pancreatin, amylases, lipases, and/or various proteolytic enzymes such as pepsin, trypsin, chymotrypsin, and papain, etc. The hydrolase enzyme assists in catalyzing the cleavage of proteins and solubilizing other tissue components and non-collagenous impurities. The enzyme may be kept in solution for an appropriate amount of time for the enzymatic activity to cause telo-peptide bonds to be broken down, which may allow the collagen fibers to unwind, as evidenced by the appearance of strand-like collagen in solution. Any suitable length of time may be used, including time ranging from seconds to minutes to hours or longer. For ficin, the enzymatic activity occurs for about 30 minutes with intermittent stirring. However, the amount of time the enzymatic activity the tissue in solution undergoes may be adjusted so that the collagen fibers from the collagen-containing tissue preserve their fiber orientation and/or native constituents that may provide potential benefits. For example, by preserving the original or native constituents in human-derived collagen products, an implant may provide that, when implanted, produces no or a low immunogenic response and allows implants to disperse and/or cross-link after implantation. In addition, retaining components of the extracellular matrix in the collagen product may promote healing.

The enzyme-treated collagen fibers are separated (130) from the enzyme-buffer solution and added (140) to an enzyme deactivation solution selected based on the enzyme used. In one embodiment, where ficin is used, a suitable deactivation solution may be sodium chlorite ($NaClO_2$) in an ammonium nitrate ($NH_4NO_3$) buffer solution. Alternatively, the deactivation solution may be an oxidizing agent such as hydrogen peroxide in a sodium chlorite buffer solution. In addition, use of an oxidizing agent may also facilitate in bleaching the fibers. The collagen is exposed to the deactivation solution for an amount of time sufficient to deactivate the enzyme reaction, for example about 1 hour when the enzyme is ficin. Generally, the enzyme deactivation solution will be a non-alkaline solution, which may be less harsh on the fibers, thereby assisting in retention of the natural collagen product constituents, e.g., collagen, extracellular protein constituents, but excluding tissue-source-derived cells. Alternatively, the enzyme may be deactivated in the enzyme solution by changing the temperature or the pH, including raising the pH, of the enzyme solution.

The treated fibers are removed (150) from the deactivation solution and subjected (160) to a series of washing cycles. Each washing cycle involves washing (161) the fibers with a suitable amount of liquid, such as about 500 ml distilled water, for a suitable period, such as about 15 minutes. The collagen product is compressed to squeeze out excess water and the pH of the distilled water used in washing the fibers is taken after each wash period (162). The pH after the first and second wash is expected to be about 7.0+/−0.5, and after a third wash is expected to be about 7.0+/−0.2. Although three washes of the fibers are described in the present embodiment, it will be understood that when the pH of the distilled water reaches a desired pH range, e.g., about 7.0+/−0.2, the washing process may be terminated. It will be understood that any suitable pH range can be used for this purpose, including from about 3 to about 9, from about 5 to about 7, or from about 6.0 to about 6.3.

In one embodiment, after washing with distilled water, excess water may be removed from the washed fibers by any suitable method, such as compression or squeezing. For example, fibers may be hand squeezed, pressed onto a fine screen, vacuumed, centrifuged, rolled between rollers separated by a suitable distance, combinations thereof, etc. Optionally, the fibers may undergo (170) a series of de-watering treatments. Any suitable treatment may be used, including, by way of example only, placing the fibers into a bath of about 100% isopropanol (IPA), heating to about 60° C., and blending for about 15 to about 60 seconds. The fibers may remain in the de-watering solution as appropriate, including for about 2 hours at about 60° C., optionally with intermittent stirring. After the first de-watering treatment, the fibers may be separated from the solution, squeezed, and subjected to another de-watering treatment, e.g, by treatment in another IPA bath and/or in a 95% ethanol/5% IPA bath (e.g., SDA 3C) for 30 minutes, as desired. The subsequent de-watering cycle may be repeated in the same manner, or the de-watering cycles may each have a duration of about 30 minutes, for a total of about 1.5 to about 2 hours of de-watering treatment. Thus, in various embodiments, the time spent by the fibers in the de-watering solution may vary. For example, in subsequent de-watering steps, the fibers may remain in the de-watering solution for about one hour as opposed to about two. In the exemplary use of about 100% IPA as the de-watering solution, the IPA, in addition to removing water from the fibers, also may assist in the removal of any oils present in the collagen product mixture.

After the de-watering cycles, the fibers are transferred (180) to another bath for removing the de-watering solution. For example, when IPA is the de-watering solution, the fibers may be added to an about 100% acetone bath and heated to about 40° C. In addition, the fibers in the bath may be blended for a period of about 15 to about 60 seconds. Removing the de-watering solution with about 100% acetone, in addition to removing alcohols or water, also may remove any oils potentially present in the collagen product mixture.

The purified fibers may be removed from the bath, separated apart from each other, and dried (190) as appropriate. One suitable drying procedure includes drying at about 40-45° C. for a period of time, such as about 4-12 hours, although any other suitable drying procedure also may be used. The isolated, enzyme treated human collagen fibers in particular embodiments includes natural, native collagen constituents, and may be used for a variety of applications including for medical implants.

The collagen product preparation and purification method may be supplemented or steps may be altered to preserve a desirable components in the collagen product. In one example, a milder processing method may be used to prepare a collagen product, and the step of adding a hydrolase enzyme, such as ficin, to the collagen-containing buffer solution (e.g., step 120) may be eliminated or replaced in order to prevent denaturing proteins in the collagen and/or to facilitate preservation of growth factors present in the collagen. By preserving growth factors in collagen, inductivity may be facilitated upon implanting collagen products formed using such an alternative method. Moreover, when a hydrolase enzyme is not used to treat the collagen, an enzyme deactivation step (e.g., step 140) may not be included. In addition, and as described further below, milder collagen implant preparation methods such as cross-linking using transglutaminase may be employed in combination with the milder collagen processing method described above.

In a further example, the collagen preparation process may include a terminal sterilization procedure such as dialysis, irradiation, filtration, chemical treatment, or other suitable procedure. In addition, collagen or tissue-containing collagen may be blended at various other points in the recovery process in addition or as an alternative to the blending processes described above. Further, homogenizing the collagen mixture may replace or supplement blending. Moreover, in order to further express water from the fibers after washing with distilled water or after the de-watering step, the collagen fibers may be frozen so that any remaining water is expelled.

The collagen preparation methods of the present application may result in human collagen fibers that are relatively pure, e.g., greater than about 70%, greater than about 80%, greater than about 90%, greater than about 95%, or greater than about 98%. According to the embodiments of the present invention, purified collagen fibers means that the fibers are treated, cleansed, or made suitable for implantation and for use as medical devices using any suitable collagen preparation, preservation, recovery or purification methods, including the methods described above. Purity does not denote any particular degree of purity, and may include a variety of levels of purity, as appropriate for the intended purpose.

In some embodiments, the collagen recovery and collagen product preparation method of the present invention does not use an alkali treatment step, and a non-alkaline solution is used for enzyme deactivation. This is useful according to embodiments of the present invention because certain collagen constituents native to humans, e.g., human growth factors and morphogenic proteins that would otherwise be stripped away by exposure to an alkaline solution, are maintained. In addition, because the collagen fibers are derived from humans, harsh purification and/or treatment processes may be unnecessary because human based collagen-containing tissue is less likely to be contaminated as compared to xenogenic collagen-containing tissue. It will be understood that collagen product preparation may be accomplished using a variety of methods and may include collagen processing steps in addition to or as an alternative to the processing steps described above.

Moreover, because the collagen fibers are sourced from humans, collagen products formed from these fibers are less likely to produce an immunogenic response when used for implantation into humans. Accordingly, the human collagen recovery and collagen product production methods, according to certain embodiments of the present invention, are simplified method compared to xenogenic collagen recovery methods, and end products made from the human derived collagen products are desirable, as they are likely to be accepted at an implant site.

Other collagen product preparation methods may also be employed according to embodiments of the invention. For example, harvested collagen-containing tissue may be scraped, sliced, e.g., from frozen specimens, lyophilized, and/or treated enzymatically, etc., to yield collagen products including fibers, fibrils, microfibrils, particles, threads, strands, etc.

Prepared collagen products may be stored in fiber, fibrillar (e.g., milled fibers), microfibrillar (e.g., appear like a fiber when viewed microscopically) and/or particulate form (e.g., ground collagen). Such prepared collagen products may be suitable for medical use in humans in their native form. Fibrous, fibrillar, microfibrillar and/or particulate collagen products in their native form may be useful as a hemostat in applications such as general surgery and/or to treat injuries, e.g., for emergency field treatment or other treatment.

Alternatively, collagen products may be processed into another form of a medical implant. Because the collagen product retains a portion of its collagen constituents that remain at least partly bound to each other and retain a portion of native non-collagenous proteins, implants may be non-immunogenic (e.g., due to the human or human-like origin), and may have improved elasticity and strength characteristics (e.g., resistant to cracking) compared to collagen implants derived from other sources (e.g., bovine-derived collagen).

Figure 2A:
FIGS. 2A-E depict methods of forming an intermediate collagen product using collagen fiber and/or thread base materials.

Intermediate Collagen Products Produced from Prepared Collagen Fiber and/or Thread Base Materials Intermediate Collagen Product I: Dispersed Collagen in Solution According to an aspect of the invention, collagen fiber and/or thread base materials prepared according to the method of FIG. 1A may be used as a starting material to produce an intermediate collagen product I. In FIG. 2A, the intermediate collagen product may be provided by dispersing (200) the prepared collagen in any suitable solution including a distilled water and lactic acid solution, or a buffer solution at any suitable temperature and pH. In various acidic embodiments, the acid can be selected from both organic and/or inorganic groups.

Intermediate Collagen Product II: Foam Containing Collagen and a Leveling Agent

Figure 2B:
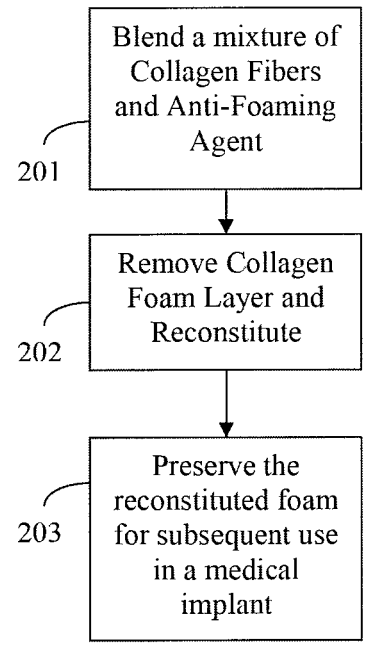

Intermediate collagen product II may be provided according to the method of FIG. 2B in which a mixture of dispersed collagen fiber and/or thread base materials and a volume of a leveling agent (e.g., an alcohol that is about 0.25% to about 15% by volume having a purity of about 50% to about 99%) are blended (201) resulting in a foam containing at least human-derived collagen and the leveling agent. The foam may be removed and reconstituted (202) as desired. For example, the foam may be reconstituted into a liquid phase such as by changing the gas-containing foam into a substantially gas-free liquid by centrifuging the foam at about 1500 to about 3000 rpm for about 1 to about 5 minutes. The collagen-containing foam reconstituted into a liquid is an intermediate product that may be preserved (203) for subsequent use in medical implant production processes. In the present invention, intermediate collagen product II is one or both of a foam containing collagen and a leveling agent (e.g., alcohol) or its reconstituted liquid. Medical implants having improved properties may be produced using such an intermediate product containing and are described in relation to collagen products below.

According to the method of FIG. 2B, when a leveling agent is blended (201) with the collagen dispersion, a separation occurs leaving a foam layer on top of a flowable liquid. The resulting foam may be separated and reconstituted (202) into a liquid. The foam layer is believed to consist of one or more types or constituents that may be different from the flowable liquid component because collagen products formed from the foam is more firm and hard compared to the collagen products from the flowable liquid. While not desiring to be bound to any particular theory, such physical characteristics may indicate that the foam constituents may include collagen that is feral/native collagen having bonds (telopeptide and carbohydrate) that have not been broken or removed, or may be a specific type or types of collagen, e.g., elastin and type III collagen, and/or may be indicative of additional components such as non-collagenous proteins, e.g., growth factors.

Figure 2C:
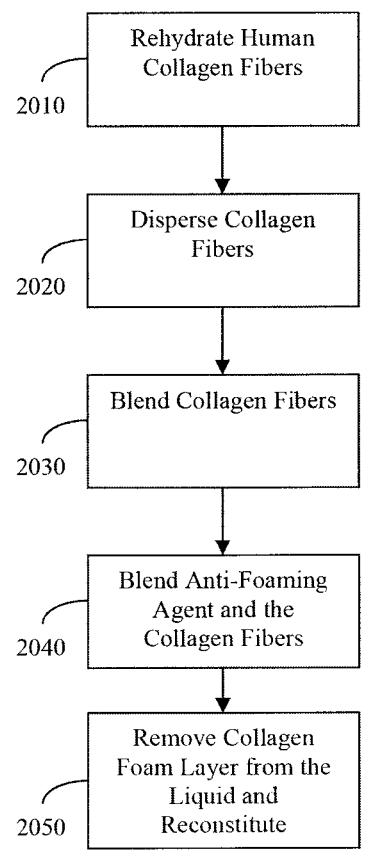

The intermediate collagen product II may also be formed using the method of FIG. 2C in which a collagen product of prepared human-derived or human-like collagen fiber and/or thread base materials are hydrated (2010), dispersed (2020) by blending (2030) or homogenizing, blended with a leveling agent (2040), and the foam removed and reconstituted (2050). Collagen fiber and/or thread base materials are hydrated (2010) by adding dehydrated or dried collagen fiber and/or thread base materials to a media that allows the fiber and/or thread base materials to become swollen and take up water without denaturing the triple helix structure of the collagen. Any suitable media may be used, including an acidic media. One example of an acidic dispersing media that is suitable for dispersion of the human collagen fiber and/or thread base materials and their resulting rehydration when forming a dura/meningeal repair matrix is an about 85% lactic acid solution in distilled water at a ratio of about 1:500, where the collagen fiber and/or thread base materials are permitted to swell for about 1 hour at a temperature of ≤about 15° C. Any of these parameters may be adjusted as desired for the particular application. The reconstituted collagen product in solution may have an about 0.5 to about 1.25% collagen density, or an about 0.75% collagen density, although any other values can be used, as appropriate. As used herein, "density" refers to the weight percent processed collagen fiber (weight/weight or w/w).

After reconstitution, the collagen product dispersion is prepared (2020) by any suitable method. "Dispersion" used in the present application encompasses any type of dispersion method including blending, mixing, agitating, and/or suspending in a mixture of water, water and an acid, e.g., lactic acid. One example of a suitable dispersion preparation method includes blending (2030) or homogenizing the fiber and/or thread base materials in solution having a preferred temperature of about 10 to about 40° C., about 10 to about 35° C., or about 10 to about 20° C., at various speeds for intervals of about 5 to about 25 seconds, with a time period of about 10 to about 60 minutes between blending intervals. In a particular example, a blending series includes blending at low, e.g., about 14,000 to about 16,000 rpm, medium, e.g., about 16,000 to about 19,000 rpm, and high speeds, e.g., about 19,000 to about 22,000 rpm, for about 10 seconds, with an interval of about 30 minutes between each blending speed, and is repeated about three times. Any of these parameters may be varied as dictated by the fiber and density specified by the product under construction. According to the presently described embodiment, the resulting dispersion may have an about 0.75% collagen density at a pH of about 2.8 to about 3.2, though any desired density and pH may be achieved.

The blended dispersion may be mixed with a leveling/precipitating agent and blended (2040) in intervals, e.g., low, medium, and high speed blending with about 30 minutes between intervals. The leveling/precipitating agent cause the collagen to at least partly precipitate in the solution. Such leveling/precipitating agents may include polyhydroxy compounds (e.g., ketones such as acetone), alcohols (e.g., ethyl alcohol (EtOH), isopropanol (IPA), surfactants, salts, etc. In one example, an alcohol having a purity of about 60% to about 99%, about 70% to about 99%, about 90% to about 99%, or greater than about 99%, at a concentration between about 0% to about 15% by volume, between about 3% to about 6% by volume, or about 5% by volume (e.g., EtOH having a purity of about 70% to about 99% at a concentration of about 5% EtOH by volume) may be added to the blended dispersion. Alternatively isopropanol (IPA), e.g. about 60% to about 99% pure IPA, may be used alone or in combination with EtOH. Other polyhydroxy compounds are disclosed in U.S. Pat. No. 5,290,558, issued on Mar. 1, 1994, entitled "Flowable demineralized bone powder composition and its use in bone repair," which is herein incorporated by reference in its entirety. Moreover, in addition to or as an alternative to the precipitating mechanisms, dewatering mechanisms are also contemplated which dehydrate collagen in solution causing the collagen to separate from water.

The resulting dispersion includes a foam layer on top of a liquid or fluid layer, each of which may contain a precipitated amount of collagen. Any resulting foam is removed and reconstituted (2050) into a gas free liquid phase, for example, by decanting the fluid from the foam, collecting the foam, and centrifuging the foam, e.g., at about 2500 rpm for about 1 to about 5 minutes.

When the leveling agents discussed above are used in preparing collagen product suspensions for collagen derived from non-human sources, foam is typically reduced or eliminated. That is, a leveling agent for a human-sourced collagen product would be an anti-foaming agent for a non-human sourced collagen. For example, upon blending an alcohol, such as ethanol, with a bovine collagen suspension, foam is typically reduced or eliminated. In the present invention, it has been discovered that by adding a component traditionally believed to be an anti-foaming agent and blending with a collagen product, a leveling effect is instead produced, and leveling agents for human-derived collagen products are not leveling agents for non-human-derived collagen. Where a leveling agent such as EtOH is used, the resulting product (e.g., sponge matrix) may be less susceptible to cracking during lyophilization, may be more homogeneous (with no or fewer fault lines that could be susceptible to tearing), and may have a crystal formation that is more regular, with less sharding.

Intermediate Collagen Product III: Collagen Containing a Leveling Agent

Figures 2D, 2E:
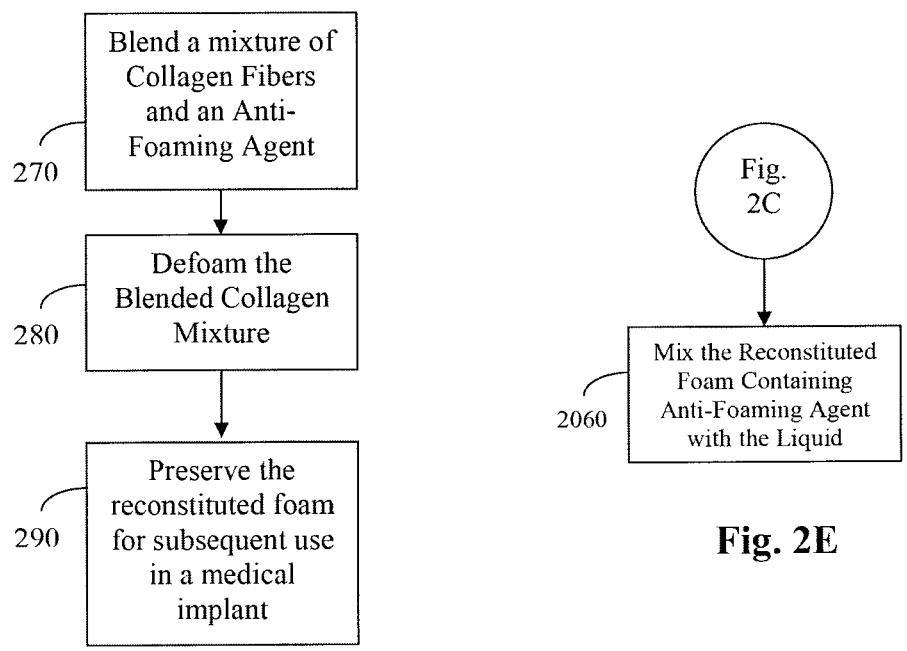

Intermediate collagen product III may be provided according to the method of FIG. 2D in which collagen fiber and/or thread base materials are dispersed in a suitable water, lactic acid, and leveling agent mixture and blended (270), and the resulting foam/liquid mixture defoamed (280) using any known method, such as by adding defoaming agents including surfactants, soaps, alcohols, tension reducing materials that are acceptable to biological activity or that are removed in processing, by mechanical means including mixing platforms that do not form surface foams (e.g., airless static, planetary Ross or Lee mixers, Graeco in line airless), or by foam elimination using degassing (e.g., centrifuging) and homogenization, ultrasonic and/or vacuum-break processes. The defoamed collagen product mixture is preserved (290) for subsequent use in forming a medical implant. Accordingly, the intermediate collagen product in the present case includes all of the collagen product originally dispersed mixed with a volume of a leveling agent.

Other intermediate collagen product production methods may also be employed. For example, intermediate collagen product III may be produced by reconstituting, dispersing, and blending a collagen product, separating the collagen product's collagen-containing foam and reconstituting, filtering, degassing, and/or centrifuging the dispersion separate from the foam, remixing the foam component, and/or reincorporating the collagen components, e.g., the collagen product components including the collagen dispersion and the collagen-containing foam. Intermediate collagen product III may also be provided according to FIG. 2E, which includes the method of FIG. 2C plus the introduction of the reconstituted foam component into the decanted collagen fluid and mixing (2060) to form a homogenous collagen product mixture. In some implementations, the homogenous mixture is refrigerated, e.g., at about 4° C. to about 10° C., for about 3 to about 24 hours before undergoing further processing. In further implementations, the decanted collagen fluid is refrigerated before the foam component is re-mixed to form a homogenous mixture.

The third intermediate collagen product may provide various advantages due to its leveling agent (e.g., alcohol) content and due to its retention of all of the originally dispersed collagen product. Certain advantages are provided further below in relation to the collagen product scaffold production methods that involve freezing the collagen product dispersion.

Figure 2F:
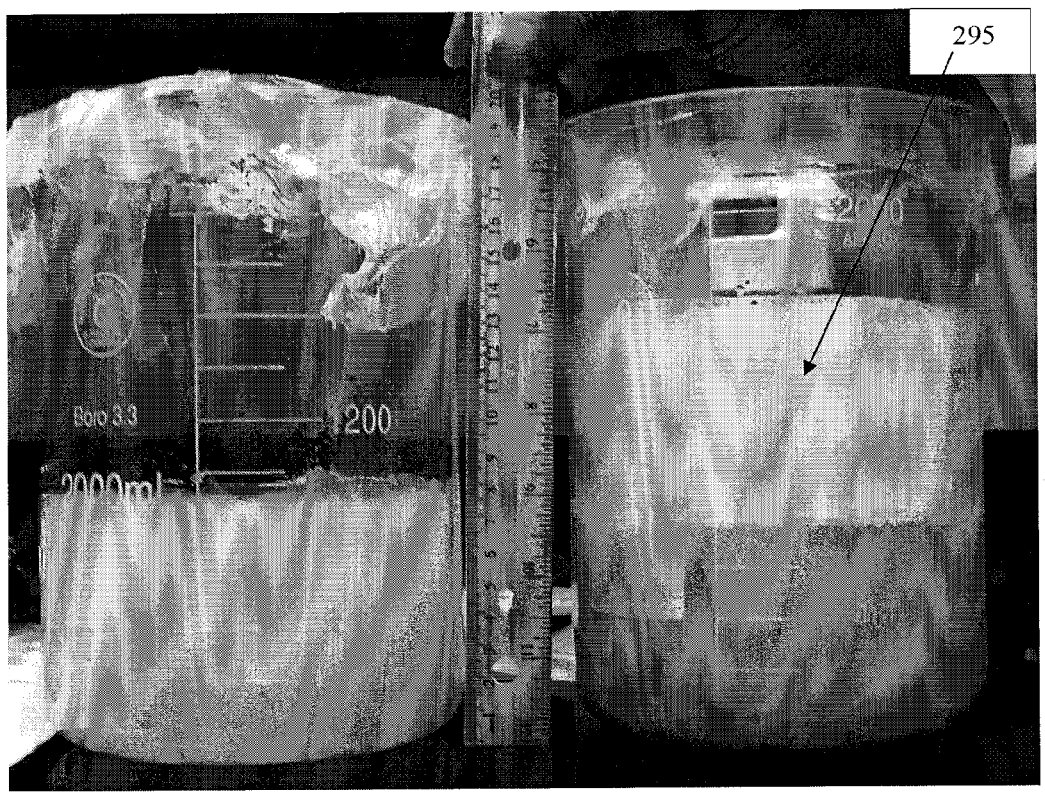
FIG. 2F is a photograph of bovine-derived collagen dispersion and human-derived collagen dispersion.

The methods described above in relation to intermediate collagen products II and III differ from other collagen product production and processing methods because typically leveling agents for human-derived collagen product are not leveling agents for non-human-derived collagen, and the type of foam produced when blending human-derived collagen product with a leveling agent is not produced upon blending collagen derived from other non-human-like sources (see FIG. 2F, discussed below). Even where foam is produced in human-derived or non-human-derived collagen product, it would typically be considered waste and discarded, while the liquid homogenous phase would be retained for further use. This is because the foam: 1) is not homogeneous with the rest of the dispersion, 2) is not a typical result when blending other non-human forms of collagen with alcohol, 3) is persistent and does not dissolve into solution unless manipulated mechanically and/or chemically, 4) may contain a relatively small amount of the dispersed collagen and thus be easily discarded without affecting the batch size, and/or 5) may be easily removed by pouring and employing a weir or spatula.

Figure 2G:
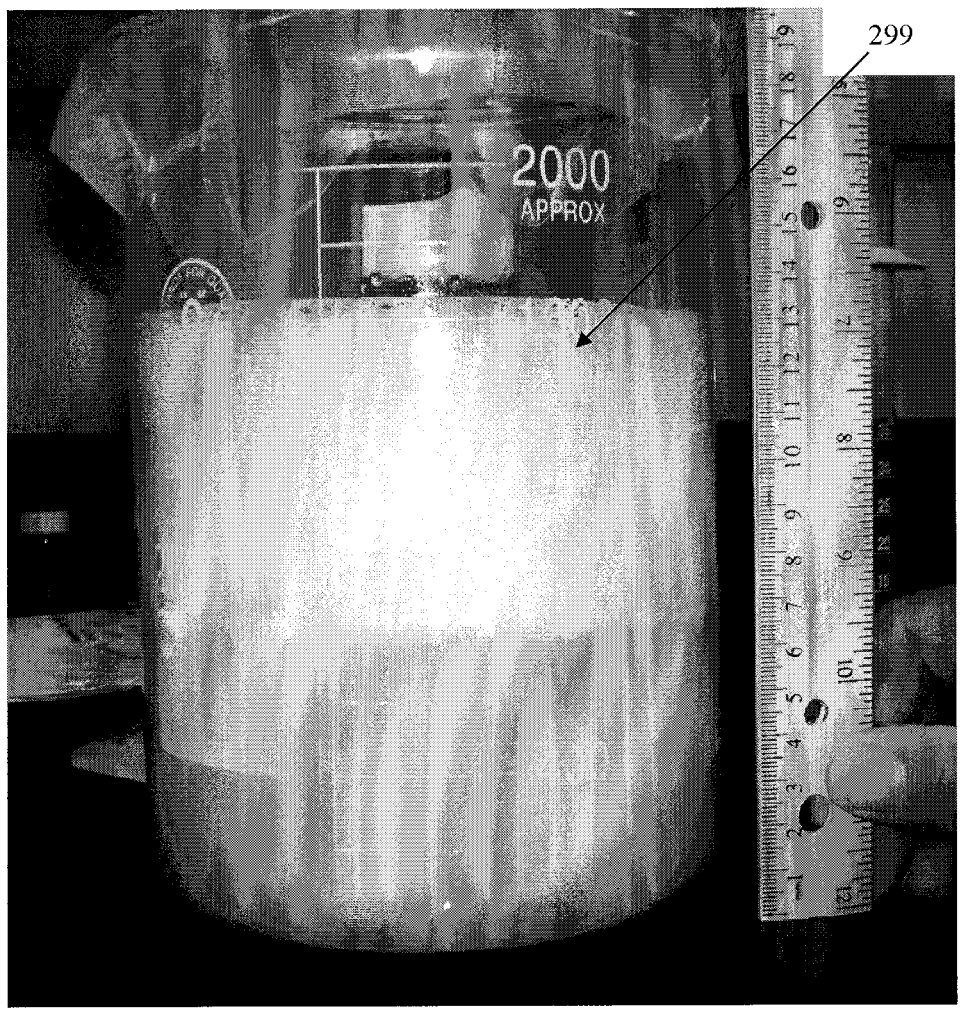
FIG. 2G is a photograph of a human-derived collagen product dispersion produced according to certain embodiments of the present invention.

Each of the above-disclosed intermediate collagen products I-III, when in dispersion, may appear to have a greenish/yellow tinge, that is slightly thickened, yet self-leveling. When the dispersion includes alcohol or another leveling/precipitating agent, mixing and/or shaking the dispersion creates a foam layer containing collagen and alcohol. FIG. 2F is a photograph of bovine-derived collagen dispersion (left) and human-derived collagen product dispersion (right) after blending, each dispersion having about a 0.75% collagen density in an about 1 Liter batch having about 50 ml of 99.99% EtOH and about 5 ml of 85% lactic acid. From FIG. 2F it can be seen that human-derived collagen product in dispersion (right) produces a foam layer 295 when blended, whereas bovine-derived collagen in dispersion (left) does not. FIG. 2G is a picture of the human-derived collagen product dispersion from FIG. 2F, in which foam layer 299 having about a 6 cm depth can be more easily discerned. The human-derived collagen product foam pictured in FIG. 2G is persistent foam that is sustained over time, and no observable change in the foam occurs when it is refrigerated for about a month. In addition, when the human-derived foam is permitted to dry at room temperature, a nearly transparent film is produced that is flexible and exhibits some plasticity. While not desiring to be held to any particular theories, it is believed that human-derived collagen product foam includes constituents or properties different from bovine-derived collagen at least because mixing a bovine collagen suspension does not produce persistent foam. Additional reasons human-derived collagen foam is believed to have unique constituents are discussed below in relation to producing collagen scaffolds using the foam component of a human-derived collagen suspension. Possible reasons for the differences in bovine and human collagen products include the relative age of the collagen specimen results in a different amount of cross-linking, bipedal vs. quadrapedal locomotion cause fascia to differ, differing food intake or uncontrolled substances can vary the composition of collagen-containing tissue, human collagen-containing tissue may be affected by different diseases, weight is controllable for bovine samples, and bovine samples may have increased growth hormones.

Various medical implants may be constructed using any of the intermediate collagen products described above, and include: films, coatings, drug delivery devices, monofilament fibers, foam &awed fibers, woven structures, mesh structures, injectable substances, vascular/neural grafts, bilary, neural and/or small intestine stents, tubes, plugs, repair matrices, scaffolds, and/or hemostats. Additional medical implants that may be produced are described in U.S. Pat. No. 6,485,723, issued Nov. 26, 2002, entitled "Enhanced submucosal tissue graft constructs;" U.S. Pat. No. 7,147,871, issued Dec. 12, 2006, entitled "Submucosa gel compositions;" U.S. Pat. No. 4,956,178, issued Sep. 11, 1990, entitled "Tissue graft composition;" and U.S. Pat. No. 5,554,389, issued Sep. 10, 1996, entitled "Urinary bladder submucosa derived tissue graft;" and in the article, Stephen F. Badylak, *The Extracellular Matrix as a Biologic Scaffold Material*, 28 Biomaterials 3587-3593 (2007), which are incorporated by reference herein in their entireties. The various implant fabrication processes described below use one or more of the intermediate collagen products to yield a collagen implant that is suitable for implantation into humans. However, it should be understood that, in some embodiments, the intermediate collagen products may be suitable as a finished product for implantation into humans without further processing.

Medical Implants Formed from Intermediate Collagen Products I-III

Collagen Product Films/Coatings

Figure 12:
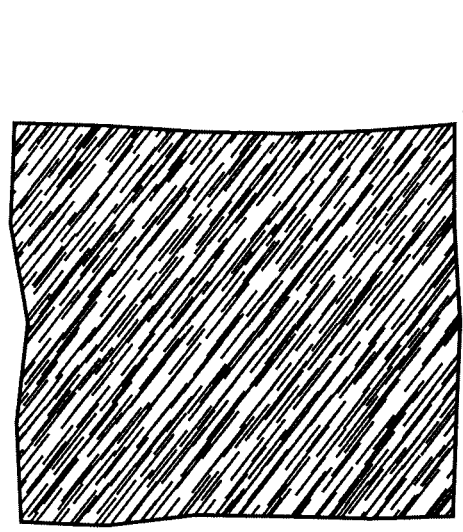
FIG. 12 is an illustration of a film formed with a human or human-like collagen product in accordance with an embodiment of the present invention.

A film barrier 1201 from FIG. 12, may be produced using any one of the intermediate collagen products described above. According to FIG. 3A, a film barrier may be fabricated by depositing (310) the intermediate collagen product in a thin layer and removing (320) the liquid component. "Removing the liquid component" used in present application encompasses any type of moisture removal process and includes freezing and lyophilizing, lyophilizing, evaporating by heating, allowing the dispersion to remain at room temperature while the liquid component evaporates naturally, or any other suitable moisture removal process. The resulting sheet may be used as a film, or may be processed further to achieve desired characteristics. In addition, before removing liquid from the intermediate collagen product, other biocompatible materials may be mixed with the collagen suspension where certain performance characteristics are desirable.

Figures 3A, 3B:
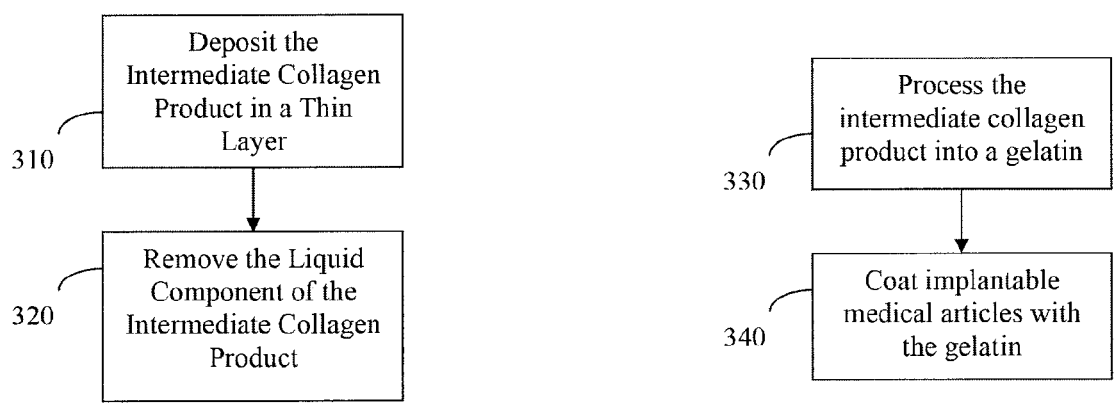
FIGS. 3A-B depicts methods of forming collagen products using an intermediate collagen product.
Figure 10:
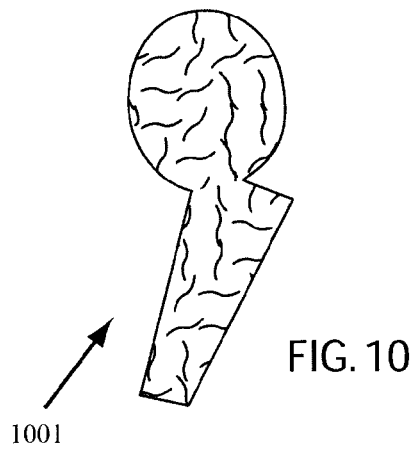
FIG. 10 is an illustration of a prosthetic coated with a human or human-like collagen product in accordance with an embodiment of the present invention.
Figure 11:
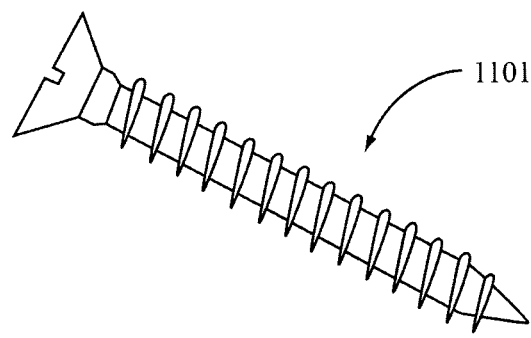
FIG. 11 is an illustration of an implantable instrument coated with a human or human-like collagen product in accordance with an embodiment of the present invention.

According to FIG. 3B, an intermediate collagen product may be processed (330) into a gelatin, and the gelatin may be used as a coating to coat (340) medical implants. In certain implementations, various prosthetics, e.g., prosthetic 1001 in FIG. 10, and/or instruments, e.g., instrument 1101 in FIG. 11, may be coated with the gelatin produced from the intermediate collagen product.

Films and/or coatings may be useful, for example, in barrier dressings (e.g., adhesion barriers and barriers to liquids), occlusions, structural supports, osteochondral retainers for cells/matrices (+/−analgesic), drug delivery devices, e.g., collagen product coating combined with analgesic, anti-inflammatory, antibiotic, and/or growth factors, and wraps for bone defects. In addition, catheters and stents may be coated. In a further implementation, a plasticizer, bioactive, bioabsorbable, soluble, and/or biocompatible component may be combined with the collagen product or the gelatin formed from human-derived or human-like collagen product in order to form a collagen product paste, slurry and/or putty, etc. In a further embodiment, a collagen product gel or film may be combined with a structural backing, e.g., a thin film, e.g., about 100 to about 200 um or about 0.05 to about 0.5 mm, such as a polylactide and/or chitosan film. The collagen product coatings and/or films may provide one or more durable layers of collagen product that may be used in general medical, cardiovascular, and/or orthopaedic settings.

Figure 3C:
FIG. 3C is a photograph of a human-derived collagen product film made from human fascia that may be prepared for use as a medical implant in accordance with certain embodiments of the present invention.

A human-derived collagen product film 341 made from human fascia is depicted in the photograph of FIG. 3C, which may be prepared for medical use in humans in accordance with certain embodiments of the present invention. Exemplary physical characteristics of the collagen product film and/or coating may depend on the type of starting material and/or intermediate collagen product or products used to produce the film and/or coating, and may include: pliable, flexible, resistant to cracking, strong, and/or dense.

Collagen Product Strands, Fibers, Filaments, Threads and Foam-Formed Strands, and Collagen Products Formed Therefrom Collagen products including collagen strands, fibers, filaments, threads and foam-formed strands formed from collagen base materials and/or intermediate collagen products, and collagen fabrics produced therefrom, are provided according to certain embodiments. Collagen strands are lengths of collagen material generally having a length that is longer than the width of the strand. Collagen fibers are arrangements of generally aligned and directionally oriented collagen materials having a material composition that includes collagen, and a selected strength for integrating the fiber into more complex structures such as collagen threads and collagen textiles, including collagen webs and non-woven and woven collagen fabrics. Collagen fibers may be natural fibers having a wide variety of assembled lengths, which may be twisted to form uniform yarns and threads of desired dimensions and strengths. Collagen threads may be a bundle of twisted fibers formed into a length for use in textile applications, for example. Collagen filaments may be formed of one or more monolithic collagen structures to provide collagen mono-filaments or multi-filaments. Collagen filaments may be fabricated from extruding and/or spinning processes. Foam-formed collagen strands are an open cell network or matrix of collagen formed into a strand and are described below.

Figure 3D:
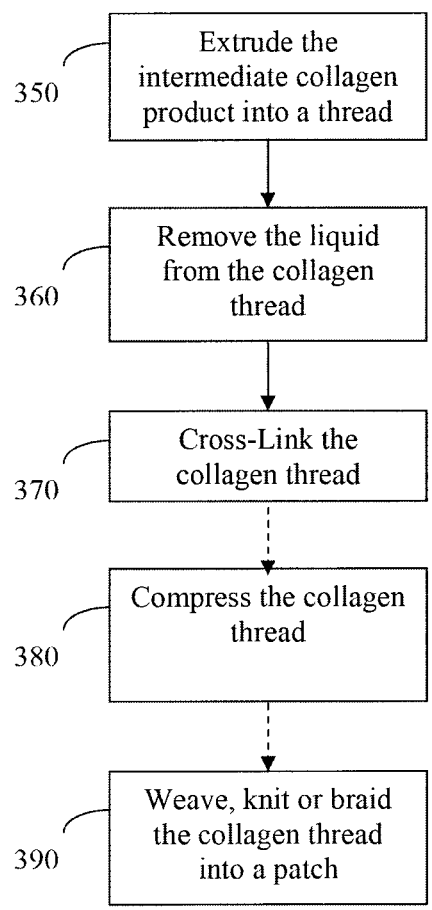
FIG. 3D depicts a method of forming a collagen product using an intermediate collagen product.
Figure 3E:
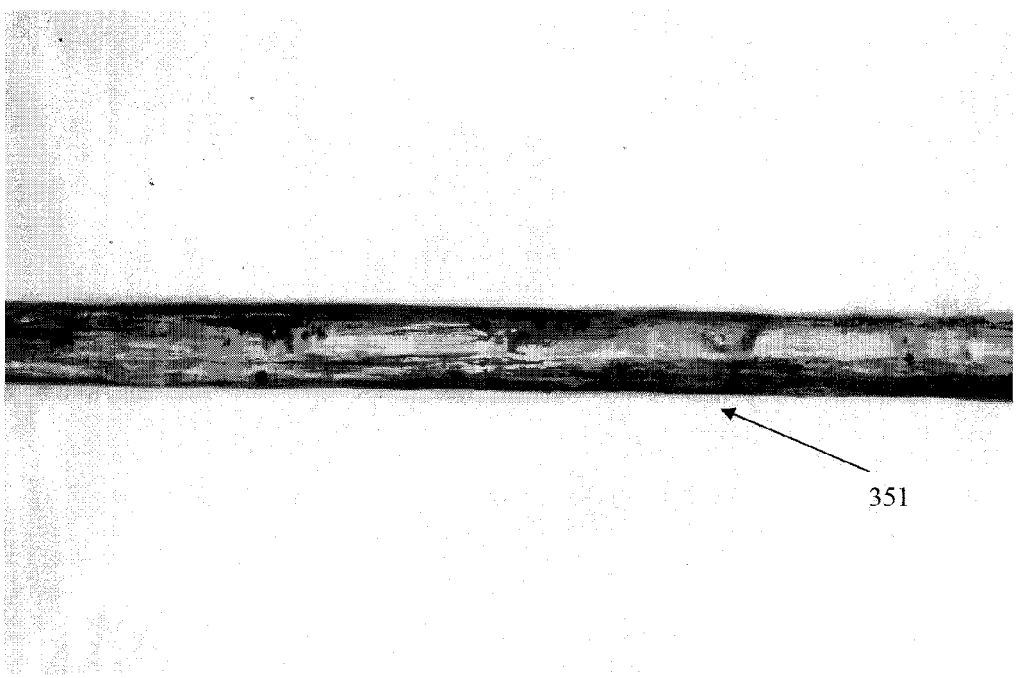
FIG. 3E is a photograph of a human-derived collagen product strand made from human fascia that may be used or prepared for use as a medical implant in accordance with certain embodiments of the present invention.
Figure 3F:
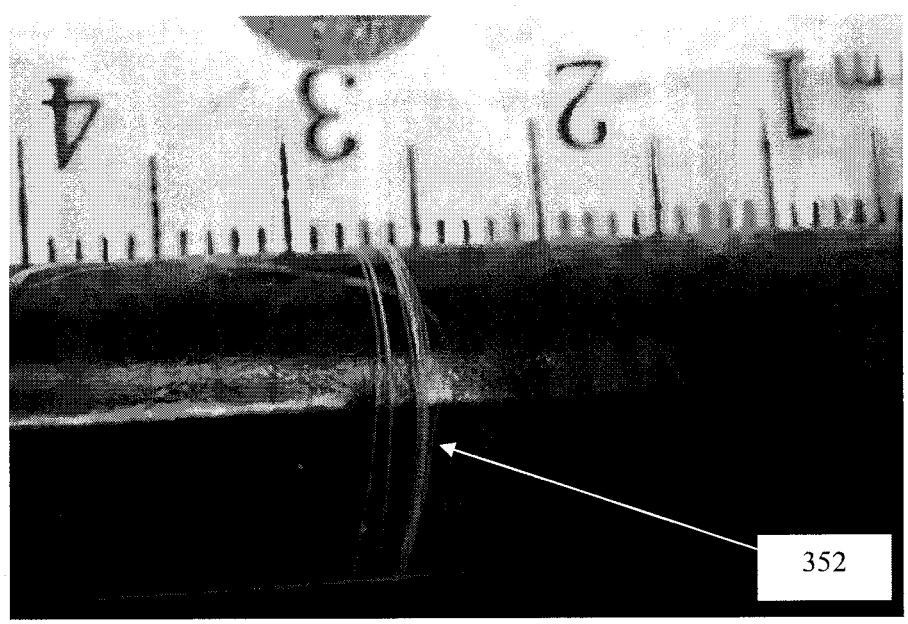
FIG. 3F is a photograph of another human-derived collagen product strand made from human fascia that may be used or prepared for use as a medical implant in accordance with certain embodiments of the present invention.
Figure 3G:
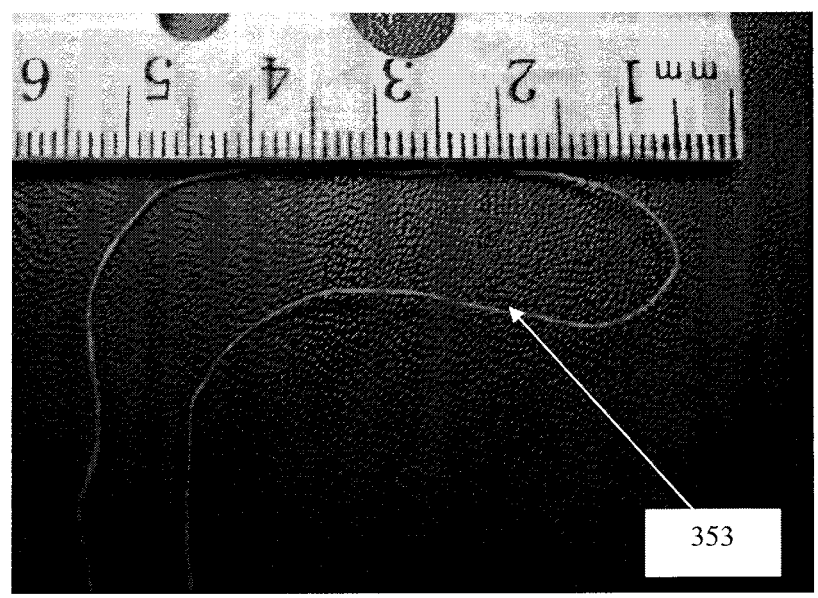
FIG. 3G is a photograph of another human-derived collagen product strand made from human fascia that may be used or prepared for use as a medical implant in accordance with certain embodiments of the present invention.
Figure 3H:
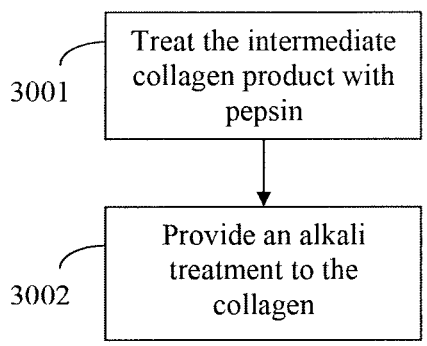
FIGS. 3H-J depict methods of forming collagen products using an intermediate collagen product.
Figure 3I:
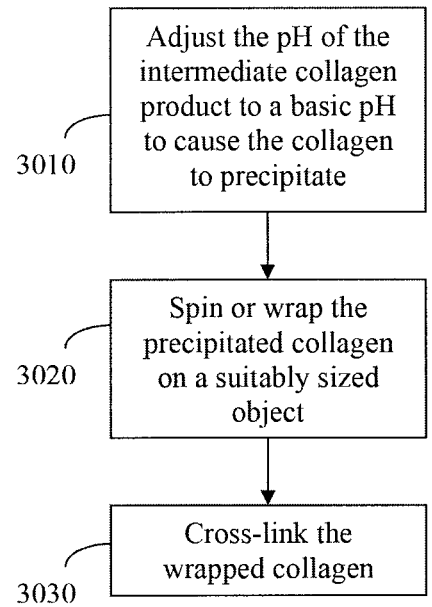
Figure 3J:
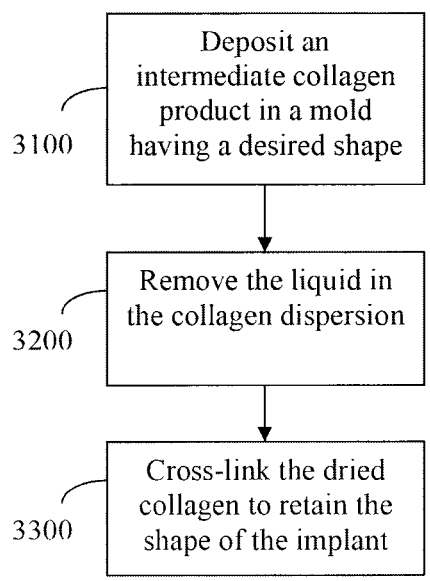
Figure 3K:
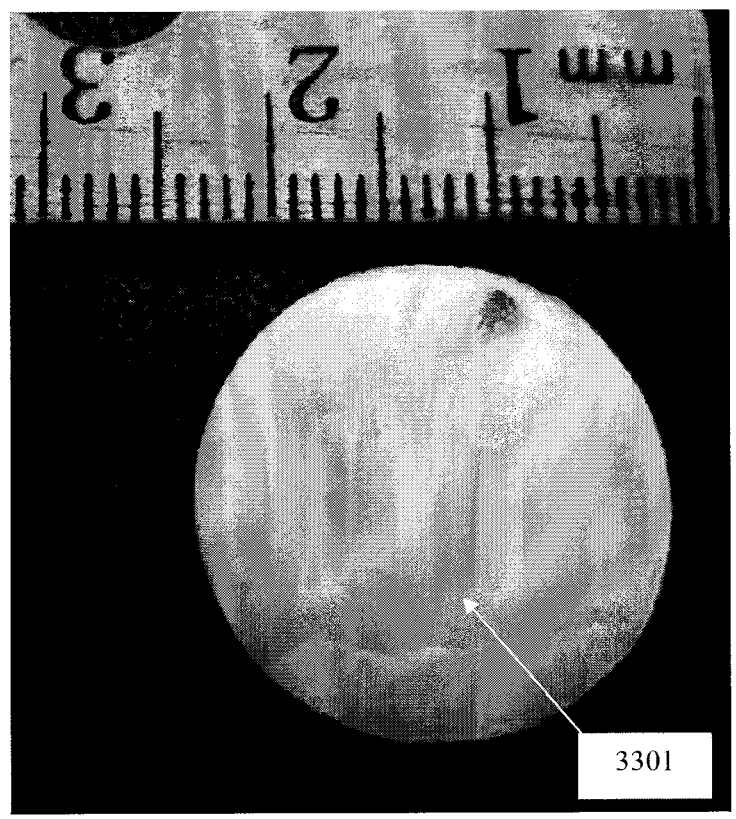
FIG. 3K is a photograph of a human-derived collagen product plug made from human fascia that may be prepared for use as a medical implant in accordance with certain embodiments of the present invention.
Figure 3L:
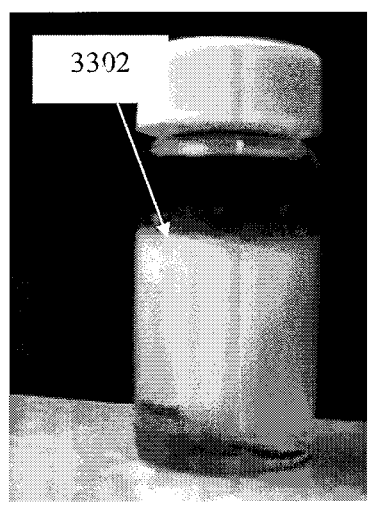
FIG. 3L is a photograph of precipitated human-derived collagen product made from human fascia that is prepared for use as a medical implant in accordance with certain embodiments of the present invention.
Figure 3M:
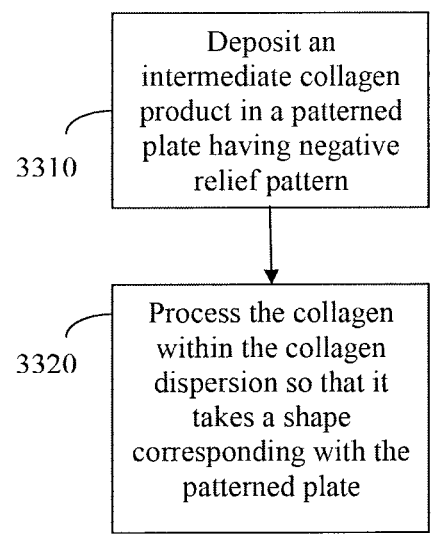
FIG. 3M depicts a method of forming a foam-formed collagen thread made from human fascia that may be used as or prepared for used a medical implant in accordance with certain embodiments of the present invention.

Foam-Formed Strands:

Intermediate collagen products may be processed into a foam-formed collagen strand according to the method depicted in FIG. 3M. According to FIG. 3M, the intermediate collagen product is deposited (3310) as a dispersion into a patterned plate having a negative relief pattern designed for forming a desired shape and size of strand. The plate containing the intermediate collagen product is processed (3320) so that the collagen within the collagen dispersion takes a shape complementary to the patterned plate, and achieves a desired porosity and density. Processing steps may include lyophilization, cross-linking, coating, and/or strand removal followed by twisting and compression. The resulting foam-formed strand includes a porous foam structure that may facilitate movement of biological materials (e.g., cells and fluid) within and through spaces of the reticulated cells of the collagen fiber walls. In various embodiments, reticulated cells are networked, communicating, or connected. The reticulated cells of the foam-formed collagen strand form an open cell network or matrix, which allows the biological materials to enter and move with relative freedom in a direction following the strand length when the strand is implanted. In various embodiments, the reticulated pores are greater than 0.60 mm, 0.70 mm, 0.80 mm, 0.90 mm, 1.0 mm, 1.1 mm, 1.2 mm, 1.3 mm, 1.4 mm, or 1.5, or less than 2.0 mm, 1.9 mm, 1.8 mm, 1.7 mm, 1.6 mm, 1.5 mm, 1.4 mm, 1.3 mm, 1.2 mm, 1.1 mm, 1.0 mm, 0.9 mm, 0.8 mm, or 0.7 mm.

According to certain implementations, the plate used to receive the collagen dispersion includes a grooved area having a predetermined shape, such as linear grooves or one or more spiral shaped grooves, curved grooves, any other desired configuration, and combinations of these. The plates may be configured so that a predetermined volume of the intermediate collagen product is deposited in the grooves. The plate may be constructed of materials that readily release the foam-formed collagen strand, such as clay, stainless steel, aluminum, plastics. The plate may be treated with a non-stick material such as Teflon to facilitate the strand removal. Methods involving the use of plates may facilitate providing a foam-formed strand with a finished edge, free of defects. However, certain implementations may not use a plate, but instead may use other forming means such as by cutting pre-lyophilized collagen sponge into strands, assembling the lengths of the strands end-to-end, and lyophilizing and cross-linking the strands to form a single length of a foam-formed collagen strand.

Figure 3N:
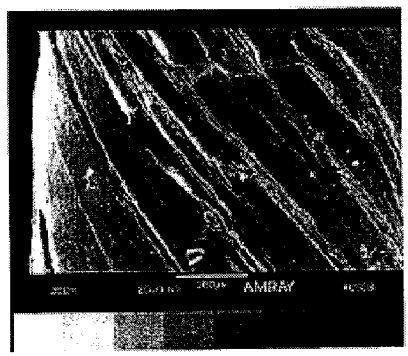
FIG. 3N is a photograph of a foam-formed collagen thread at a 250× magnification.
Figure 3O:
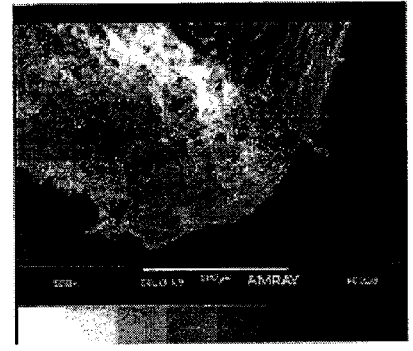
FIG. 3O is a photograph of a cross-sectional view of a foam-formed collagen thread at a 500× magnification.

In one embodiment, the plate includes U-shaped grooves with dimensions for providing a partially rounded foam-formed collagen strand that is initially about ⅛" to about ¼" wide and about ⅛" to about ¼" tall, or which has a cross-section that is about ⅛" to about ¼", or which ranges from mils to about an inch in width and mils to about an inch in height. However, the grooves may have a number of cross-sectional shapes to provide the desired strand shape. In addition, the width and depth of the grooves may vary so that the width and height of the foam-formed collagen strand is about 1/16" to about ⅛", from about ⅛" to about 3/32", from about 1/16" to about ¾", and from about 1/32" to about ⅝". It will be understood that the width and height of the strand may differ relative to each other, and that the cross-sectional shape may be irregular or substantially consistent along the length of the strand, which may be about several inches (such as 12 inches) to about 30 feet long. FIGS. 3N and 3O are photographs of twisted foam-formed collagen threads. In FIG. 3N, the collagen thread is shown at a 250× magnification. In FIG. 3O, the photograph is of a cross-sectional view of a h-collagen coated foam-formed collagen thread at a 500× magnification.

The intermediate collagen product may be deposited (3310) by casting as a dispersion and pouring or extruding into the plate. The collagen dispersion may have any desired collagen density, including from about 0.001% to about 20%, about 0.1% to about 10%, about 0.5% to about 5%, or about 0.5% to about 1.5% collagen density. In one example, the dispersion may have an about 0.75% collagen density.

Upon initial processing (3320), such as by removal of the liquid component, e.g., evaporation, lyophilization or freezing and lyophilization, the formed strand may have an initial strength similar to a lyophilized collagen sponge having a similar cross-sectional dimension, which may correspond to the selected collagen density. With increasing collagen density, the strength of the foam-formed strand increases.

Additional processing, including collagen cross-linking, may take place while the dispersion remains on the plate, following removal of the formed strand, or during another preparation phase. When the collagen is cross-linked in its dispersed form, e.g. while the dispersion remains on the plate, the dispersion may include cross-linking components and may facilitate strand formation. After removal from the form, the post-formed strand may be cross-linked using one or more chemical cross-linking agents such as those disclosed below in the section entitled "Methods for Preparing Collagen Product Scaffolds Formed from Intermediate Collagen Products II-III." The post-form cross-linking may take place pre- or post-compression and/or pre- or post-turning, where applicable. In certain implementations, multiple foam-formed collagen strands may be cross-linked end-to-end to form a continuous strand having a length spanning hundreds of feet. In other implementations, multiple foam-formed collagen strands may be cross-linked side-by-side to form a collagen strand having a diameter that is an order of magnitude larger than the diameter of a single foam-formed collagen strand.

Upon its removal from the plate, the foam-formed collagen strand may be further processed. According to certain implementations, the foam-formed collagen strand may be compressed. Concurrently with or following compression, the foam-formed collagen strand may be turned or twisted to reach a desired thread dimension, spiral orientation, and/or density. Compressing and/or twisting reduces the diameter of the foam-formed collagen strand down to a fraction of its initial diameter. Upon compressing and/or twisting, a foam-formed collagen strand having an initial cross-sectional diameter of about ¼" (e.g., derived from a ¼" tool), may have a cross-sectional diameter of about 0.010" to 0.012", whereas a compressed and/or twisted about ⅛" diameter foam-formed collagen strand may have a cross-sectional diameter of about 0.006" to 0.009". The resulting compressed and/or twisted foam-formed collagen strand appears thread-like, and exhibits an increased strength due to the compressed nature of the matrix or network of reticulated cells. Spiraling the foam-formed collagen thread also increases uniformity while providing directional cell growth opportunity. In addition, the network of reticulated cells may be altered upon compression and/or twisting, which tends to close-off a portion of the reticulated cells that were open upon initial processing. Strand compression and/or twisting may be performed by hand or via processes involving twisting machines.

In certain implementations, the foam-formed collagen strand may be coated to impart a variety of properties. Coatings may be provided to the strand upon initial formation, upon compression and/or twisting, or in connection with lyophilization and/or cross-linking. Coatings compositions may include collagen, pharmacologic, synthetic and hybrid mixtures. Collagen coatings may serve to prevent or delay degradation of the collagen. For example, collagen fibers used as core fibers may be coated in order to delay the degradation of the core of a collagen product in a controlled manner. This provides for the preservation of engineered characteristics such as tensile strength, which may be useful in facilitating healing and returning the native tissue to its native tensile strength during the healing process. Collagen coatings may also include drugs, therapeutic agents or other non-collagenous components that are released over time. Time release mechanism may be influenced by bulk erosion, surface dissolution or metabolic digestion characteristics. Taking one or more of these characteristics into account, the components may be provided as coatings in a desired amount in order to control or influence a variety of conditions. For example, a non-steroidal anti-inflammatory drugs (NSAIDS) may be incorporated into a coating to control and meter inflammation in order to induce, accelerate and/or promote healing. Analgesics may also be incorporated into a coating in order to control pain. Collagen coatings may also facilitate the prevention of adhesion. For example, coatings of sodium citrate disposed on a collagen product may prevent thrombosis and fibrotic tissue from attaching one organ or tissue plane to another. In a particular example, coatings disposed on a collagen product used in ovarian or fallopian surgery may facilitate maintaining fertility post-surgically. In open heart surgery applications, coatings for preventing adhesion may prevent attachment of the heart to the sternum, which could otherwise result in restraint of the heart muscle and reduced efficacy.

The above-described processing methods involved in preparing the foam-formed collagen strand may be tailored to achieve desired foam-formed collagen strand properties including collagen foam density, inner foam structure, and/or strength. The collagen density of the intermediate collagen product dispersion is relevant to the strand's collagen foam density. The degree and type of collagen cross-linking may affect the porosity and/or strength of the foam-formed collagen strand. Methods of cross linking can include a) altering pH, freezing rate, and freezing point by altering the chemistry of a mixture, such as by adding alcohol to control collagen matrix/sponge porosity. In various embodiments, pore uniformity and size can be used to control matrix/foam integrity as well as resistance to tearing. Using aldehyde cross-linking can be used to influence strength in terms of 'shrink' resistance, tensile performance and resistance to degradation. Other cross linking chemistries can increase resistance to in vitro degradation and tensile failure. In addition, the degree of strand turning or twisting affects the inner foam structure, which tends to reduce foam porosity by closing reticulated cells initially having an open pore structure, or by reducing the available channels for biological materials to enter and move freely. By adjusting foam density and/or the porosity for cellular movement, it is possible to match the resorption/remodeling of the implant material to the healing rate of the repair site. Density can be controlled by regulating the quantity of collagen included in its dispersing media. Porosity can be controlled by altering pH, density of collagen, freeze rate and freeze point adjustment, such as by introducing alcohol.

In another implementation, the collagen dispersion may include EtOH for managing ice crystal formation and reducing sharding, resulting in a post-lyophilized foam-formed collagen strand having a substantially consistent reticulated cell size, which may facilitate predicting rate of movement of biological materials over time. In various embodiments, from about 3% to about 5% or about 7% by volume to volume alcohol is added. In more specific embodiments, about 5% is used.

In alternative embodiments, it may be desirable to twist and compress the foam-formed strand to an exaggerated degree in order to provide an impenetrable strand having high strength. In other embodiments, however, a high-strength strand may be formed that includes a desirable degree of porosity to facilitate movement of biological materials.

Foam-formed collagen strands may be used in further processes including braiding, weaving, knitting, felting and/or in fabric production, for example.

Extruded Strands:

According to FIG. 3D, the intermediate collagen product may be processed into a strand by extruding (350) the intermediate collagen product into a strand, removing (360) the liquid component from the collagen product, e.g., by lyophilization or dewatering in which the strand is extruded directly into a solvent media to extract water, and cross-linking (370) the collagen product to form a cross-linked strand. In some implementations, pH adjustment and cross-linking (370) the strand may be achieved within the dewatering solvent media. In addition, the collagen product strand may be compressed (380), woven, knitted, and/or braided (390) into a patch. Alternatively, the strand may be cross-linked in-situ during the extrusion process.

The strand, according to certain configurations, may have monofilament type structure, or multi-filament structure, and may appear like fine fishing line, sewing thread, yarn, or a suture. The photographs of FIGS. 3E-G are collagen product strands. The strand pictured in FIG. 3E is a monofilament strand 351 similar to a fishing line. FIG. 3F is another photograph of collagen product strands 352 wrapped around a spindle. FIG. 3G is another photograph of a towed and twisted collagen product strand. As compared to the collagen product strand in FIG. 3F, the collagen product strand 353 in FIG. 3G is more robust and appears yarn-like. Each of the strands pictured may be prepared by wet extruding through a spinneret (single and multi-ported) resulting in a multitude of collagen product fibers being assembled in a linear agglomeration while being cross-linked, precipitated, and dewatered. The strand may be about 50 nanometers to about 3 millimeters, or about 50 microns to about 200 microns in diameter. The strands may be a fiber mass of loosely formed fibers that cling together by crimping or by their surface geometry, similar to how cotton fibers cling together. The strands may be slightly twisted or spun to form a strand having a more uniform diameter resembling sewing thread. In addition, the strands may be formed into a ribbon by positioning multiple strands side-by-side and drying the strands. In another example, the ribbon may be twisted to form a collagen product strand similar to a sewing thread, which may or may not be thicker than the twisted strand of collagen product described above. For example, a collagen product rope may be formed using the collagen product strand, which may have a diameter of between about 200 microns to about 3 millimeters. The strands resembling sewing thread may be about 100 microns to about a millimeter or more (e.g., about 2 mm to about 5 cm) in diameter. Collagen product strands may be used in further processes including weaving, knitting and/or braiding, for example.

Strands Formed by Electrostatic Spinning:

Alternatively, the stand may be formed by electrostatic spinning in which high electrical energy is used to form a Taylor Cone and send fiber bursts to a ground plate for deposition. The fiber begins in a collagen product dispersion that exits the electrostatic cone in a liquid form and is dried into a fiber during its flight to a grounding plate. The resulting fiber may be about 50 to about 400 nanometers in diameter. Each of the above-described collagen product strands may be prepared for use as a medical implant or may be further processed into, for example, a collagen product patch, in accordance with certain embodiments of the present invention.

The collagen strand formed from the intermediate collagen product by foam-forming, extruding or electrostatic spinning may be used to produce medical implants or may be used alone for suturing, for example. In certain implementations, the foam-formed collagen strand with its foam fiber core may be combined with various types of non-collagenous filaments (i.e., synthetic polymer) or hybrid (i.e., composed partially of collagen and partially of another non-collagenous material) filaments by braiding or cabling. For example, the foam-formed collagen strand may serve as a core for a braided cable, e.g., a series of braided filaments, having various engineered functions. Braid-based products including foam-formed collagen strands may be used in cable tension bands, and rotary cuff and suture applications.

In another example, the foam-formed collagen strand and/or the cables and braids formed therefrom may be knotted, looped or woven in knitting or weaving processes to form repair scaffolds. Using foam-formed collagen strands in scaffold applications may promote directional movement of biological materials along the length of the strand. It may be appreciated, however, that scaffolds may be engineered using the foam-formed collagen strands to conduct biological materials in a single direction (e.g., towards the wound site), bi-directionally (e.g., towards and away from the wound site), or multi-directionally (e.g., transverse movement about and around the wound site).

Figure 7:
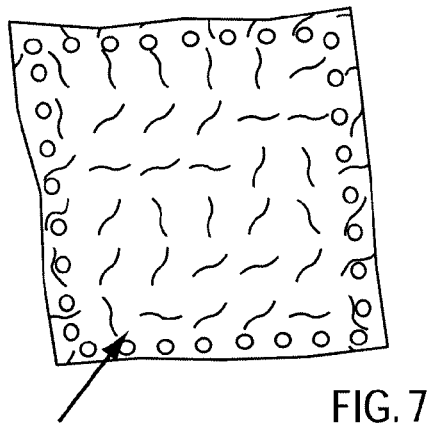
FIG. 7 is an illustration of a non-woven collagen product fabric.
Figure 8:
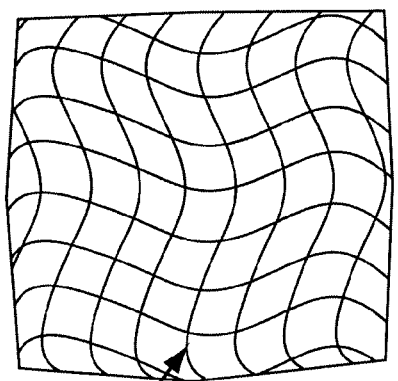
FIG. 8 is an illustration of a woven collagen product fabric.

When the collagen strand formed from the intermediate collagen product by forming, extruding or electrostatic spinning is used to produce medical implants such as a repair patch or sling (FIGS. 7 and 8), a pliable sheet of collagen product may result, which may be sutured around the area to be repaired.

According to certain implementations, a non-woven repair patch (FIG. 7) may be formed using a collagen product thread by employing a felting process.

In alternative implementations, a repair patch 801 or sling may be woven, braided, and/or knitted (FIG. 8), or may be formed from a combination of two or more of weaving, braiding (flat, three-dimensional, etc.) and knitting (warp knitting or three-dimensional knitting involving knitting two or more knitting processes).

Additional tissue repair fabrics and tissue repair fabric production methods are described in U.S. Pat. No. 5,733,337, issued on Mar. 31, 1998, entitled "Tissue Repair Fabric," which is incorporated by reference herein in its entirety. In a further alternative, the collagen product sheet may be formed by any of the above-mentioned processes and formed into tubes, e.g., tubes 1301 from FIG. 13, for applications such as vascular grafts and bilary, neural and/or small intestine stents, described further below.

Repair patches may be useful in applications such as: hernia repair, bladder repair (bladder slings), spinal tension band, tensile loaded implantable products, annular repair for the spine, and/or for repair, reconstruction, augmentation or replacement of a sphincter, meniscus, nucleus, rotator cuff, breast, bladder, and/or vaginal wall. Accordingly, the repair patch or sling may be used in general surgical settings, in spinal, vascular, and/or neurosurgical settings, and/or for sports medicine surgical applications. In addition, collagen strands may be used as reinforcements in a weave or net within a collagen sponge. Furthermore, the aforementioned collagen implants may be further processed upon formation such as by further cross-linking, and/or coating.

Injectable Collagen Products

The intermediate collagen products may be use to produce an injectable form of collagen. According to FIG. 3H, the intermediate collagen product may be treated (3001) with pepsin to remove telopeptides, and subjected to an alkali treatment (3002) so that, when implanted, the collagen product produces no or a low inflammatory response. The injectable collagen product may be useful in applications such as: scar revision, contracture revision, hypertrophic scar treatment, cosmetics, cosmetic surgery, wrinkle removal, cell delivery, drug delivery, clear collagens, dispersed collagens, micronized collagens (cryogenic grinding), and/or collagen product mixtures, e.g., collagen mixed with thrombin. Accordingly, injectable collagen products may be useful in various medical fields including plastic surgery, dermatology, and/or amputee stump revision.

Some methods that use non-human fascia to prepare soft tissue filler, which may be useful in accordance with some embodiments of the present invention, are described in U.S. Patent Application Publication No. 2002/0016637, published on Feb. 7, 2002, entitled "Soft Tissue Filler;" and in Steven Burres, MD, Preserved Particulate Fascia Lata for Injection: A New Alternative, 25 Dermatologic Surg., 790-794 (October 1999) which are incorporated by reference herein in their entireties.

Collagen Product Tubes

Figure 13:
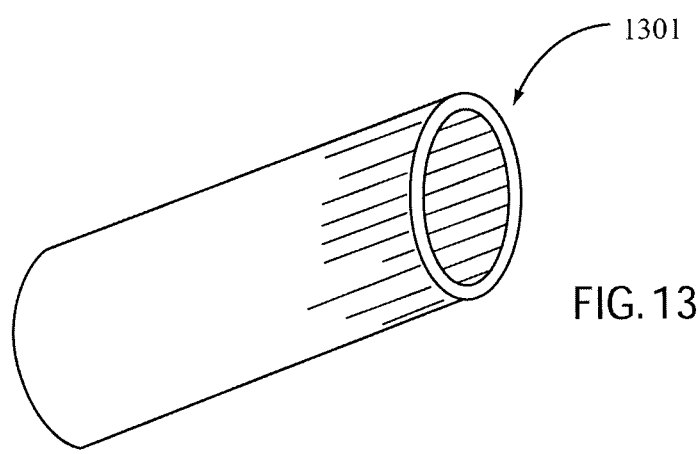
FIG. 13 is an illustration of a collagen product for use as a vascular graft or a bilary, neural or small intestine stent, formed with a human or human-like collagen product in accordance with an embodiment of the present invention.

The intermediate collagen product may be processed and formed into tubes for use as vascular grafts and bilary, neural and/or small intestine stents (FIG. 13). Various processing techniques may be employed to construct a tube-like structure that may serve as vascular material or as a stent. According to the method of FIG. 3I, vascular/neural graft or stent is made by adjusting (3010) the pH of the intermediate collagen product to a more basic condition, resulting in the collagen product fiber and/or thread base materials partly or fully precipitating. The precipitated collagen product fiber and/or thread base materials may be firm and entangled, while being at least partly suspended in the water media, and may be easily be spun or wrapped (3020) onto a dowel or mandrel of a size suitable for reproducing the vascular/neural tissue to be repaired. The resulting grafts may be cross-linked (3030) to maintain their shape after removal of the dowel. In addition to fabricating vascular and neural grafts and/or stents using the process described above, other implants that may be fabricated include: maxillary reconstruction tubes, which also contain mineral or allograft material, and/or hernia repair implants. Collagen product tubes may accordingly be useful in craniomaxillofacial, vascular, neurological, and/or general surgical applications.

Collagen Product Plugs

Figure 9:
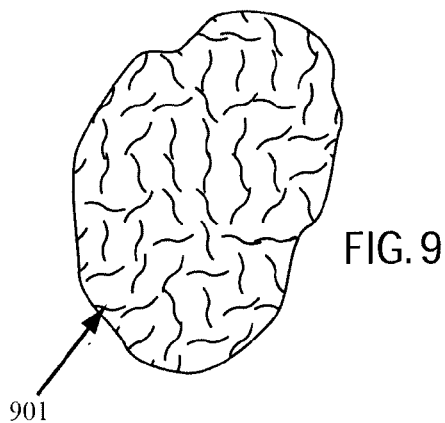
FIG. 9 is an illustration of a meniscus or cartilage repair structure formed using a human or human-like collagen product in accordance with an embodiment of the present invention.

Other medical implants such as plugs, meniscus repair structures, or cartilage repair structures 901 (FIG. 9) may be formed using the intermediate collagen product of the present invention. For example, in the method of FIG. 3J, an implant structure is formed by depositing (3100) a collagen product dispersion in a mold having a desired shape, removing (3200) the liquid in the collagen product dispersion, for example by lyophilizing, and cross-linking (3300) the implant in order to retain its desired shape. For an implantable plug, the dispersion may be deposited into a bullet-like mold, for example. Liquid may be removed from the dispersion using any suitable method including by lyophilization. Subsequently, the lyophilized collagen product structure may be cross-linked so that the implant retains its shape. In another example, the collagen product dispersion is mixed with a suitable biocompatible substance before depositing the dispersion into the mold. Collagen product plugs may be useful in cardiovascular surgical applications where the plugs may be inserted into vasculature to treat certain conditions, such as "blue baby" conditions. Collagen product plugs may be compressed by, for example, twisting, so that they can be inserted into the surgical site through a catheter. Upon rehydration in the surgical site, the plugs will assume their original shape.

A collagen product plug 3301 is depicted in the photograph of FIG. 3K, in which the collagen is processed in a similar manner compared to the human-derived collagen product scaffolds described below except the collagen product is bounded by a form or a mold. From FIG. 3K, the collagen product plug 3301 has about a 22 mm diameter. However, the collagen plug may be of any suitable diameter depending on its intended use.

In Vitro Collagen Product Applications

The intermediate collagen product may be used in any suitable context. For example, the intermediate collagen product may be useful for in vitro applications and may be prepared for in vitro applications by various methods. For example, collagen products may be precipitated by any suitable method. Alternatively, the intermediate collagen product may be preserved, e.g., FIG. 1A, and may be used for in vitro applications. The intermediate collagen product or the precipitated collagen product may be useful in applications such as for the manufacture of ex vivo tissue engineered products, cell culture media, and/or assays. Accordingly, collagen products for in vitro applications may be used in the cell tissue and engineering industry and/or in the medical testing industry.

FIG. 3L is a photograph of precipitated collagen product fibers 3302 in a vial having been precipitated from a collagen product dispersion. The precipitated collagen product may be of a self-assembling type where, once a precipitating agent is added to the collagen product suspension, collagen product fibers precipitate into the solution that appear like a broken-apart cotton ball. Such an en masse precipitated collagen product is easily recovered from the solution and may be used as a medical implant, or may be further processed depending on the in vitro application of the human-derived collagen product.

Collagen Product Scaffolds

Method for Preparing Collagen Product Scaffolds from Intermediate Collagen Product I Intermediate collagen product I may be formed into a collagen scaffold according to the method described in FIG. 2D in U.S. patent application Ser. No. 11/673,972, filed Feb. 12, 2007, entitled "Methods for Collagen Processing and Products using Processed Collagen."

Methods for Preparing Collagen Product Scaffolds Formed from Intermediate Collagen Products II-III Alternatively, intermediate collagen product II or III may be formed into a collagen product scaffold according to the methods described below. According to FIG. 4A, an intermediate collagen product produced according to FIG. 2B, 2C, 2D or 2E is frozen (401) and the liquid component is removed (402) to yield a medical implant. It will be understood that additional processing steps may be involved in preparing collagen product scaffolds, which may include the formation of holes or fenestrations in the intermediate collagen product prior to freezing (401) described further in relation to FIG. 4B.

According to the invention, an alcohol, such as EtOH, or another substance, which forms the intermediate collagen product II or III, remains in the dispersion when the mixture is frozen and causes the freezing characteristics of the intermediate product to be altered. For example, the crystal size of the ice crystals in the frozen intermediate product containing alcohol may be controlled. Other agents also may be used to control ice crystal formation and size. As a result, the quality of the finished collagen product may be more accurately predicted and/or controlled because controlling crystal size allows the size of the void spaces, i.e., interstices, resulting from removal (such as lyophilization) of the water and alcohol component, and the fiber size of the collagen product to be controlled. Thus, collagen products may be produced that have void spaces similarly sized, e.g., a narrow size distribution of the void spaces, distributed evenly, e.g., homogenous, with a desired pore density, resists cracking, has a high degree of plasticity, and/or an end product that is stronger compared to collagen products not having alcohol in the dispersion. That is, freezing characteristics of collagen product dispersions where there is no agent controlling ice crystal size may result in uncontrolled ice crystal size during freezing, resulting in a wide range of void space sizes. As a result, large shard ice crystals may result in large and/or uneven void spaces in the finished products, which may cause weaknesses and/or brittleness in the finished product.

Figure 4A:
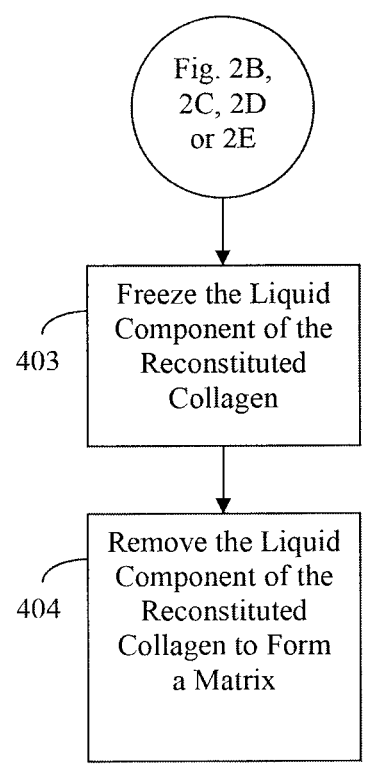
FIGS. 4A-B depict methods of forming collagen product scaffolds.
Figure 4B:
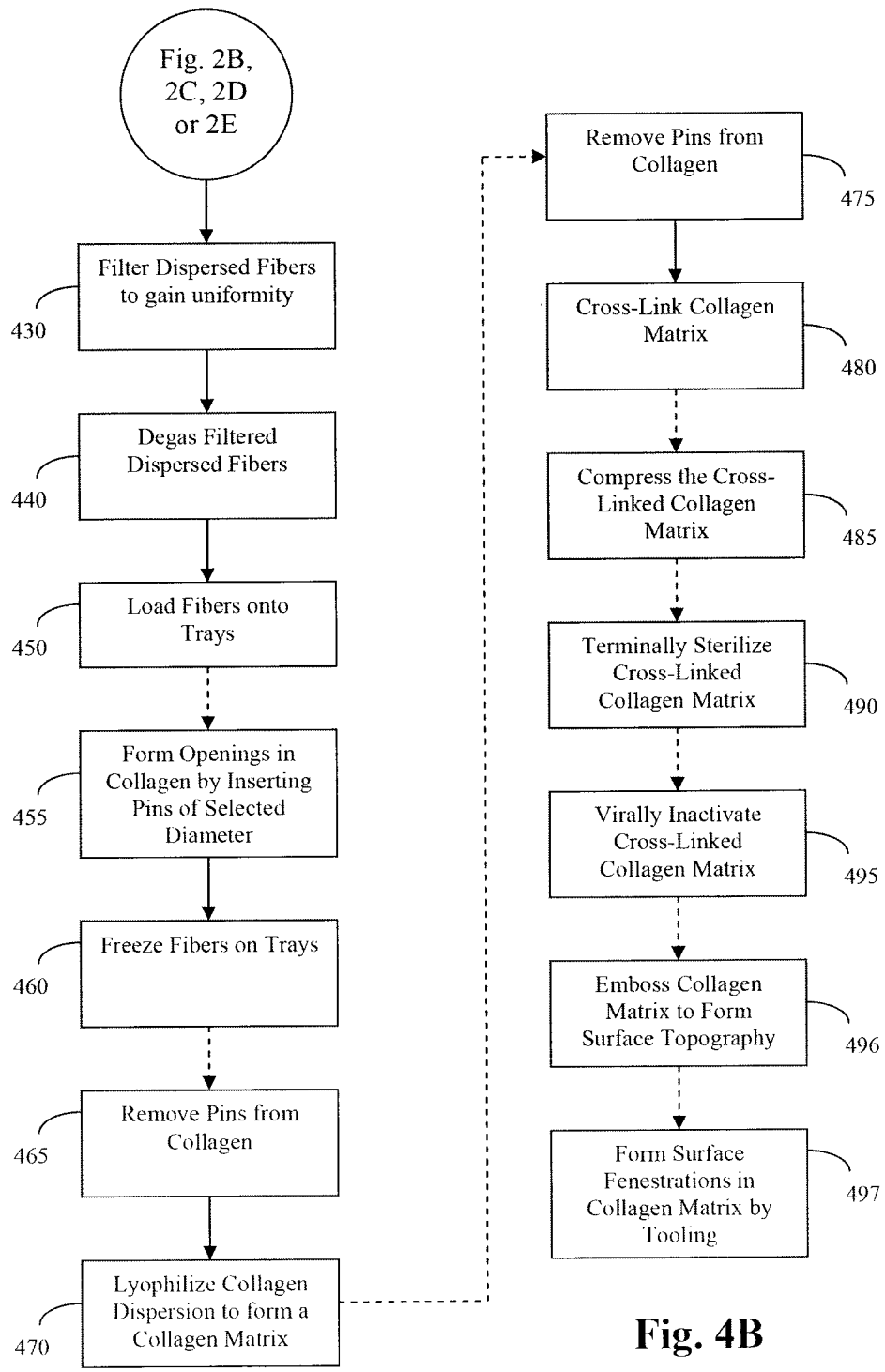

Another method for producing a collagen product scaffold provided in FIG. 4B. According FIG. 4B, a wound repair scaffold or matrix is produced by following the steps of FIG. 2B, 2C, 2D or 2E. The intermediate collagen product in alcohol may be filtered (430), which may enhance uniformity. For example, the dispersion may be filtered through a woven screen mesh having 0.024" round or square openings, through a woven or perforated stainless steel screen having about 8 to 24 gauge holes, or through a screen having a series of openings that form about a 30% open area. Filtering may be repeated to ensure a uniform dispersion. In some embodiments, the filtering is conducted at a desired temperature, e.g., a temperature of ≤about 15° C., or any other desired temperature or range of temperatures.

The filtered collagen product may be subsequently degassed (440), which may affect the porosity of the finished product. In one example, the collagen product is degassed via centrifugation, e.g., at about ≤15° C., which can eliminate large irregular pockets of gas or air. In addition or alternatively, the collagen product may be degassed by vacuuming. The degassed product may be collected by slow decant while discarding any precipitate, such as dense collagen particles resulting from lactic acid not penetrating interior collagen product fiber and/or thread base materials in a dense fiber bundle or pellet.

The filtered collagen product is or can be loaded (450) into stainless steel or aluminum trays to a depth ranging from any thickness greater than 0 mm to several inches thick, or about 0.5 mm to about 35 mm, or at a depth of about 4 mm. For example, some dispersion depths may include about 5, 7, or 12 mm. However, the depth the collagen product is loaded into the trays is based on the desired end product thickness, which may be about 0.1 cm to about 15 cm in height, width, and depth, or about 12 cm to about 15 cm in height and width and about 0.1 mm to about 12 cm in depth, or any suitable dimension.

In some embodiments, openings may be formed (455) in the collagen by inserting pins or structures of a diameter or size selected to form a desired opening size into the filtered collagen within the trays. For example, stainless steel pins or structures, poly-fiber monofilaments and/or rods (e.g., Teflon rods) may be inserted along the x-axis, y-axis, and z-axis of the collagen layer, i.e., along the length, width and height of the collagen product within tray, to provide a selected number of openings having a selected pattern. The pins or structures may be of any desired size, geometry, curvature, and configuration. In one example, a plurality of channels generally oriented in a first direction, i.e., channels that traverse the length of the filtered collagen, may intersect with a plurality of channels generally oriented in a second direction, i.e. channels that traverse the width of the filtered collagen. Channels may directly intersect, in that they connect with one another, or channels may overlap one another but not directly intersect, as when viewed perspectively. Any number or fraction of channels may directly intersect, or overlap, from none to all channels. Further, channels may be within planes, where some channels intersect (or overlap) in a plane or region, and other channels intersect (or overlap) in other planes or regions, where such planes or regions can be considered as layered or stacked within the length or width of the material. In certain implementations, the ratio of openings within the collagen may be about 1%, about 5%, about 10%, about 20%, about 40%, about 50%, about 60%, or greater.

The trays loaded with the collagen product dispersion product may be frozen (460). For example, the trays may be frozen from room temperature, e.g., about 18-23° C., to a temperature of about −20° C. to about −60° C., or about −30° C. to about −50° C., for a duration of about 6 hours, for example, to achieve a uniformly frozen dispersion. This may be accomplished in any suitable manner, including by freezing the product in a freezer or lyophilizer. In certain embodiments, when openings are formed (455) by pins or structures inserted into the filtered collagen, the pins or structures may be removed (465) once the collagen product dispersion is frozen, or the pins or structures may remain in situ for further collagen processing.

Once frozen, the collagen product dispersion may be lyophilized (470) to maintain the shape and distribution of the collagen product sponge matrix while removing the liquid, e.g., water and alcohol, components of the dispersion. According to certain embodiments, a lyophilizer is programmed to conduct a number of cycles, each cycle having a set temperature, at a given vacuum pressure and for a given period of time. For example, the temperature inside the lyophilization chamber can be in the range of about −70° C. to about +30° C., the vacuum pressure can range from about 90 Millitorr to about 2000 Millitorr, and the duration for each cycle may range from about 1 hour to about 10 hours. It will be understood that the cycle parameters may be selected and/or adjusted in order to remove the water component of the collagen product dispersion without causing the collagen product matrix to collapse or become damaged. In certain implementations, when openings are formed (455) by pins or other structures inserted into the filtered collagen, the pins or structures may be removed (475) once the collagen product dispersion is lyophilized.

In some embodiments, the lyophilized collagen product matrix may be cross-linked (480) to maintain the matrix in a desired form, to impart desirable mechanical properties of the finished matrix, and/or to control the residence time of the matrix after implantation. In certain embodiments, cross-linking may be achieved by exposing the lyophilized collagen product matrix to a cross-linking agent. Chemical cross-linking agents include those that contain bifunctional or multifunctional reactive groups, and which react with functional groups on amino acids such as epsilon-amine functional group of lysine or hydroxy-lysine, or the carboxyl functional groups of aspartic and glutamic acids. By reacting with multiple functional groups on the same or different collagen molecules, the reacting chemical cross-linking agent forms a reinforcing cross-bridge. Cross-linking agents may include: monoaldehydes, dialdehydes, polyepoxy compounds, polyvalent metallic oxides, chemicals for esterification of carboxyl groups followed by reaction with hydrazide to form activated acyl azide functionalities in the collagen, organic tannins and other phenolic oxides derived from plants, tanning agents, glycerol polyglycidyl ethers, polyethylene glycol diglycidyl ethers, sugars, enzymes, heterobifunctional cross-linking agents and transglutaminase. Particular examples of vapor phase gasses may include: formaldehyde, glutaraldehyde, acetaldehyde, polyepoxy and diepoxy glycidyl ethers, titanium dioxide, chromium dioxide, aluminum dioxide, zirconium salt, glyoxal pyruvic aldehyde, dialdehyde starch, dicyclohexyl carbodiimide hydrazide, dicyclohexyl carbodiimide, hexamethylene diisocyanate, dicyclohexyl carbodiimide and its derivatives, hexamethylene diisocyanate, glucose, and genipin. Genipin is a naturally-occurring cross-linker, which is discussed in various articles including: Sung H W, Chang Y, Liang I L, Chang W H, Chen Y C. Fixation of biological tissues with a naturally occurring cross-linking agent: fixation rate and effects of pH, temperature, and initial fixative concentration. J Biomed Mater Res 2000; 52(1):77-87; Huang L L, Sung H W, Tsai C C, Huang D M. Biocompatibility study of a biological tissue fixed with a naturally occurring crosslinking reagent. J Biomed Mater Res 1998; 42(4):568-76; Tsai C C, Huang R N, Sung H W, Liang H C. In vitro evaluation of the genotoxicity of a naturally occurring crosslinking agent (genipin) for biologic tissue fixation. J Biomed Mater Res 2000; 52(1):58-65; Sung H W, Huang R N, Huang L L, Tsai C C, Chiu C T. Feasibility study of a natural crosslinking reagent for biological tissue fixation. J Biomed Mater Res 1998; 42(4):560-7, each of which are incorporate by reference in their entireties. Glutaraldehyde cross-linked biomaterials have a tendency to overcalcify in the body. In this situation, should it be deemed necessary, calcification-controlling agents can be used with aldehyde cross-linking agents. These calcification-controlling agents include: dimethyl sulfoxide (DMSO), surfactants, diphosphonates, aminooleic acid, and metallic ions, for example ions of iron and aluminum. The concentrations of these calcification-controlling agents can be determined by routine experimentation by those skilled in the art.

In certain embodiments, cross-linking may be achieved by exposing the lyophilized collagen product matrix to a cross-linking agent in the form of a vapor phase gas including gasses of one or more of the above-listed cross-linking agents. Any suitable cross-linking method may be used. For example, the collagen product matrix may be suspended in a vessel holding a volume of aldehyde solution sufficient to cover the bottom of the vessel. The vessel with the matrix suspended inside may be covered for a suitable period of time, e.g., a range of about 15 minutes to 2 hours, to which allow the vapor phase of the aldehyde to cause vapor phase cross-linking at a suitable temperature, e.g., 18-23° C. Alternatively, the lyophilized collagen product matrix may be cross-linked by dehydrothermal cross-linking, by subjecting the matrix to ultraviolet light, or by any other suitable method. Various cross-linking methods and cross-linking agents are described in U.S. Pat. No. 6,123,731, issued on Sep. 26, 2000, entitled "Osteoimplant and Method for its Manufacture." In alternative embodiments, collagen cross-linking may be achieved using a chemical cross-linking agent such as a citric acid derivative. Cross-linking methods involving the use of citric acid derivatives and other substances are disclosed in PCT/US08/86563, filed Dec. 12, 2008, entitled "Bone/Collagen Composites and Uses Thereof," which is herein incorporated by reference in its entirety for any relevant purpose. In another example, transglutaminase may be used as a collagen cross-linking agent in order to employ milder product formation conditions, which may provide benefits to the final collagen product. For example, transglutaminase may cross-link collagen without damaging living cells, which may facilitate preserving natural human constituents in collagen and promote growth activity. Collagen products, such as collagen sheets, that include living cells and/or native human constituents such as human growth factors, which are prepared by employing collagen processing (e.g., removing the enzyme treatment steps) and product forming methods using milder conditions, may provide the final product with more active collagen containing materials. Alternatively, xenographic tissues substantially equivalent to human SIS, bladder, etc., may be enzymatically treated to render the tissue non-immunogenic and may be cross-linked using transglutaminase in order to provide active collagen products.

Figure 5A:
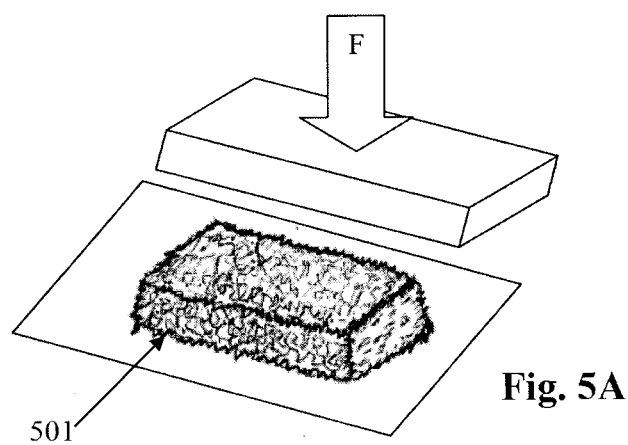
FIG. 5A is an illustration of a collagen product sponge before compression.
Figure 5B:
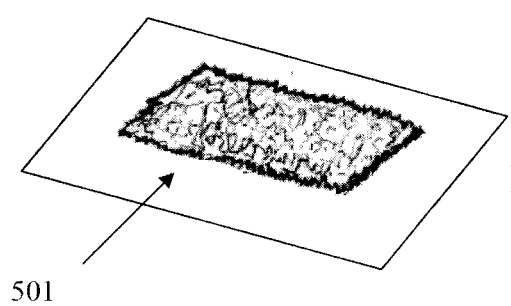
FIG. 5B is an illustration of a collagen product sheet after compression.

According to certain implementations, the cross-linked collagen product may optionally be compressed (485) to yield a collagen product with a smaller thickness compared to its pre-compression thickness. For example, the compressed product may be ⅔, ½, ⅓, ¼, 1/10, 1/20, 1/30, 1/40, or 1/50 to 1/100 the thickness of the original product thickness. In a particular example, for a 4 mm collagen product sponge, compressing at about 125 to 175 psi, about 150 psi, or about 6,000 pounds force on a 4"×5" collagen product, for about 30 seconds yields a collagen product with a thickness of about 0.13 mm. The compressed product may resemble a pliable sheet or film having a paper-like appearance. FIG. 5B depicts a collagen product sheet formed as a result of compressing the collagen product sponge in FIG. 5A by force "F." Furthermore, in some embodiments, the cross-linked collagen product may be cut to size, molded to size, or embossed in addition to or as an alternative to being compressed. In alternative embodiments, the matrix may be compressed and subsequently cross-linked, which may provide a matrix that has a smaller thickness compared to a matrix that is cross-linked and compressed.

In some embodiments, the cross-linked matrix may be terminally sterilized (490) and/or virally inactivated (495). Any suitable terminal sterilization method may be used, including ethylene oxide gas treatment, cobalt radiation, gamma irradiation, electron beam radiation, gas plasma processing, etc. Sterilization and/or viral inactivation methods are provided in Brown P., et al., Sodium hydroxide decontamination of Creutzfeld-Jakob Disease virus, New England J. of Med. Vol. 310, No. 11; Abe S., et al., Clinical experiences with solvent dehydrated fascia lata in plastic surgery, Jap. J. Plast. Reconst. Surg. 1991, Vol. 11, 721-730; and Hinton R., Jinnah R. H., Johnson C., et al., A biomechanical analysis of solvent-dehydrated and freeze-dried human fascia lata allografts, Am. J. Sports Med. 1992, 20: 607-612, each of which are herein incorporated by reference in their entireties.

In addition to or as an alternative to sterilizing, the cross-linked collagen product matrix may be packaged for subsequent use as a wound repair matrix. Packaging the collagen product may protect it from environmental conditions. When the collagen product is compressed, the product may be sealed in an envelope or plastic bag. The compressed product may be prepared for use by, for example, wetting the compressed sheet-like material. In some embodiments, wetting may cause the collagen product to return to its original sponge-like state, for example, when compression occurs after cross-linking. Alternatively, wetting may cause the collagen product to expand to a shape smaller than its original sponge-like state, for example, when compression occurs before cross-linking. The wetting process may include immersing the collagen product in water or spraying the collagen product with water or saline, e.g., about 0.9% saline, and may take place in a medical setting such as an operating room. Alternatively, when the collagen product is not compressed and resembles a sponge, the product may be sealed in a tray and used in medical settings.

In further embodiments, the top, bottom and/or side surfaces of the collagen product matrix optionally may be embossed (496) to form surface topography. When openings or fenestrations are formed (455) in the filtered collagen during processing, surface embossing may converge with the pre-formed channels arranged in the x, y, and/or z direction. For example, embossing a top and bottom surface of the collagen product matrix may provide pathways to the channels to facilitate fluid movement into the graft. Embossing may also provide for fluid management so as to avoid fluid accumulation under the graft and further may provide for the removal of excessive wound fluid drainage. Additionally or as an alternative to forming openings (455), subsequent to forming the collagen matrix, one or more surfaces of the collagen matrix may be tooled (497) to form surface fenestrations. When embossed regions are matched between two or more layers of the collagen product matrix, they combine to provide channels in the plane of the combined collagen implant. Such formed channels can enhance cell and fluid access into the interior of the implant. In-plane channels may also be formed by other means in a single layer, including forming the collagen matrix around a series of wires or meshes, and then removing the wires or meshes after manufacture.

Collagen Product Scaffolds Formed from Intermediate Collagen Products

Wound repair scaffolds produced according to the methods of FIGS. 4A and 4B, U.S. patent application Ser. No. 11/673, 972, and variants thereof, are depicted in FIGS. 4D-W, 5A-B, 6 (Note, the scaffold of FIG. 5A is the same as the scaffold 601 of FIG. 6), and 14, in which the wound repair scaffold resembles a collagen product sponge or film.

Figure 4C:
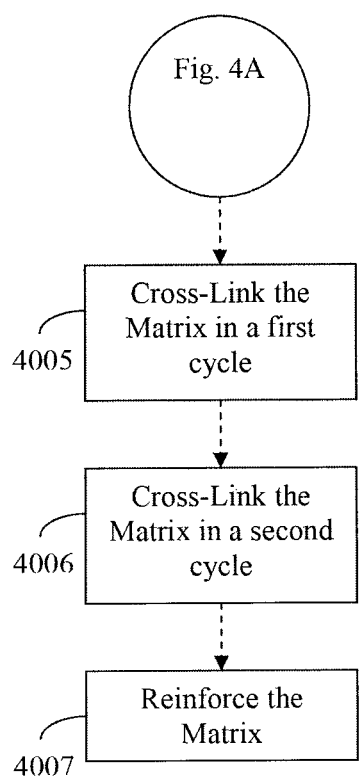
FIG. 4C depicts a method for forming an altered collagen product scaffold.
Figure 4D:
FIGS. 4D-G are photographs of collagen product scaffolds produced according to certain embodiments of the invention made from human fascia that may be prepared for use as a medical implant in accordance with certain embodiments of the present invention.
Figure 4E:
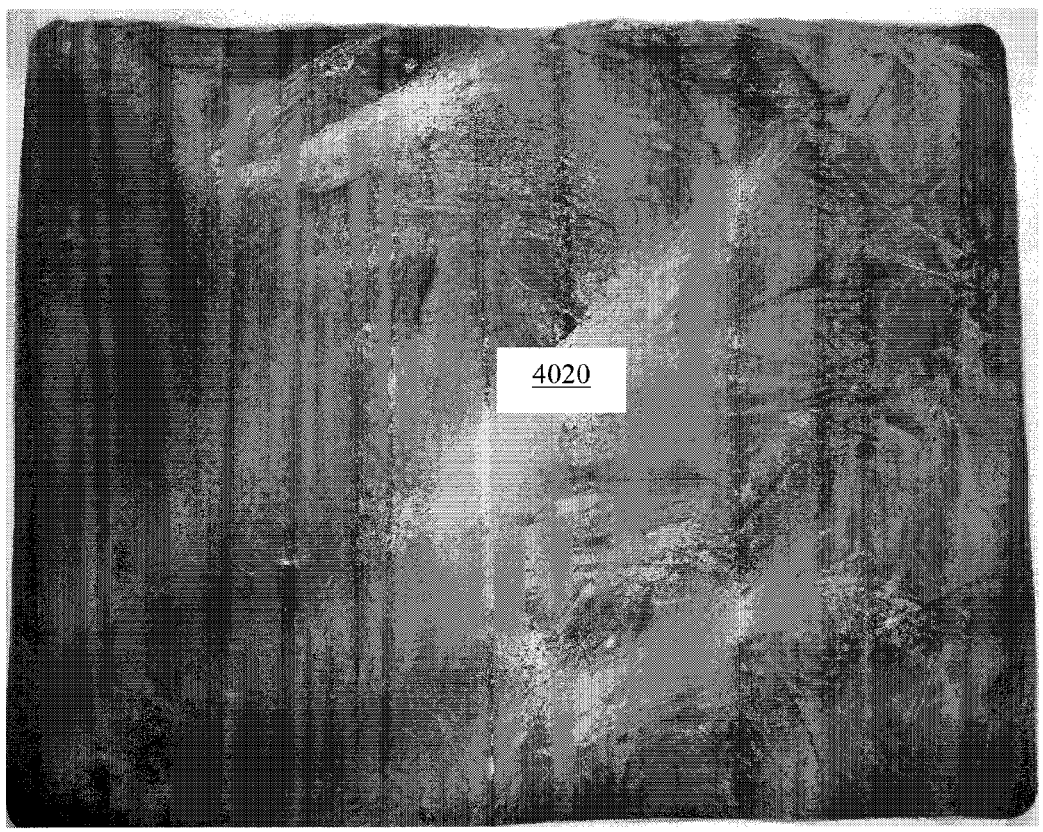
Figure 4F:
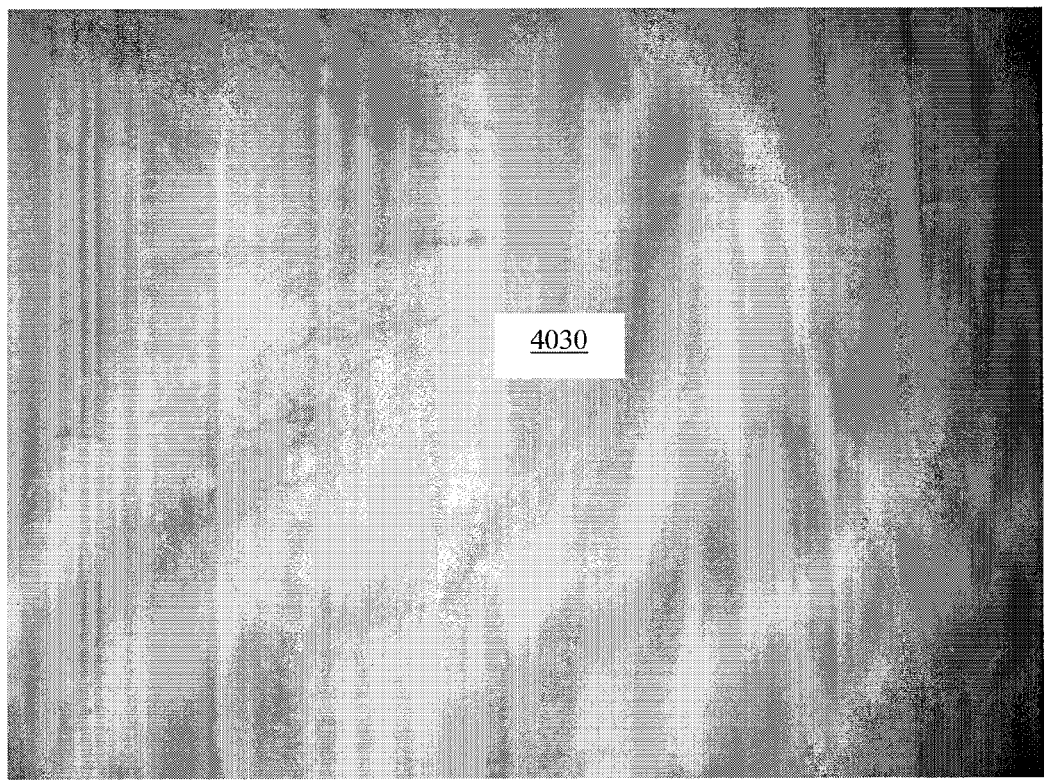
Figure 4G:
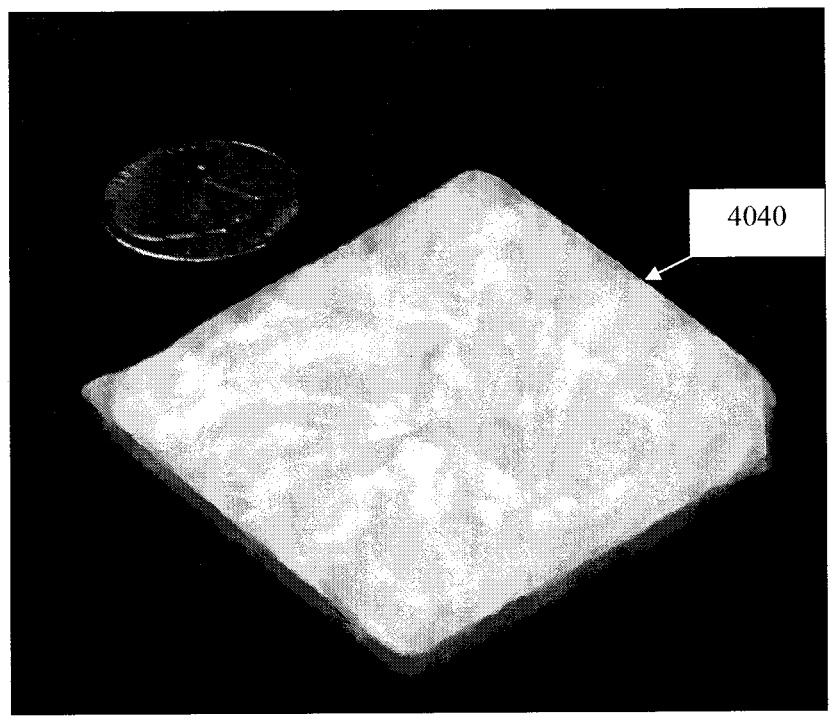

The photographs of FIGS. 4D-G depict collagen product scaffolds 4010, 4020, 4030 and 4040 that are between about 3 to about 6 mm thick that are made from human fascia in the form of an intermediate collagen product containing 5% ethanol that has been frozen, lyophilized and cross-linked with a suitable cross-liking agent for about an hour. The resulting human-derived collagen product 4010 in FIG. 4D is characterized by crystal patterns having a narrow size distribution. In FIG. 4E, the resulting human-derived collagen product 4020 is characterized by a small amount of crystal sharding on the top right side of the sample, and a near homogenous or uniform scaffold product on the bottom left side with no crystal sharding. The photographs of FIGS. 4F and 4G each show a collagen product matrix 4030, 4040 having a marbling pattern across the top surface. A marbled appearance in the end product is desirable because the appearance of an opaque white foam is evidence of the absence of an ice crystal pattern, an amorphous surface, and void spaces with a narrow size distribution. The collagen products 4030, 4040 pictured in FIGS. 4D-G are acceptable collagen products for use as a medical implant because the collagen products do not include quality deviations, e.g. large crystal shard borders, that may cause cracking. This is due to the presence of alcohol in the frozen dispersion, because by its presence the crystal nucleation and crystal size may be controlled during freezing resulting in no or small crystals that are bounded. In contrast, when a collagen product does not include alcohol in the freezing and/or lyophilizing steps in the production method, a thin, nearly transparent foam with frost-like patterns similar to the appearance of onion skin results, which is brittle and prone to cracking when stressed. While the above embodiments are between about 3 mm and about 6 mm thick, it will be understood that collagen product scaffolds produced according to the invention may be between about 1 mm and about 12 mm thick, between about 3 mm and about 6 mm thick, or about 3.5 mm thick.

Figures 4H, 4I:
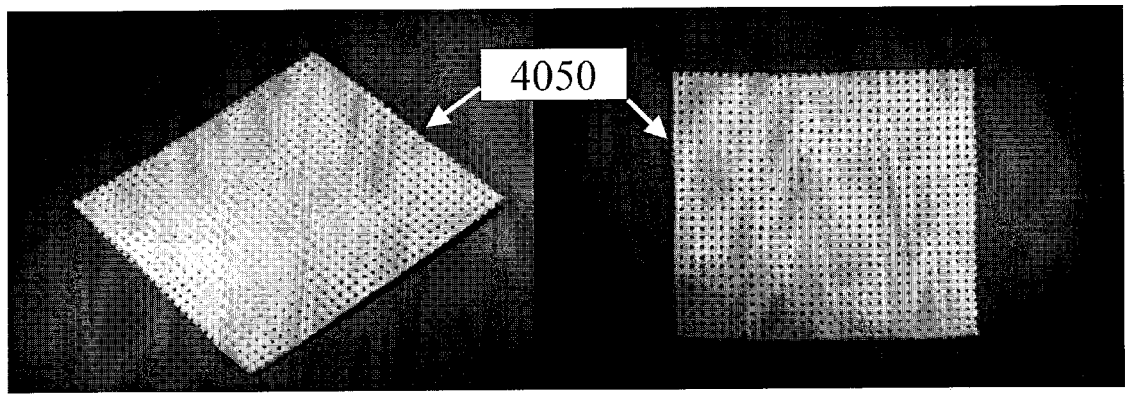
FIGS. 4H-I are photographs of perspective and top views of a 0.56 mm fenestrated patterned wound repair scaffold in accordance with certain embodiments of the present invention.
Figures 4J, 4K:
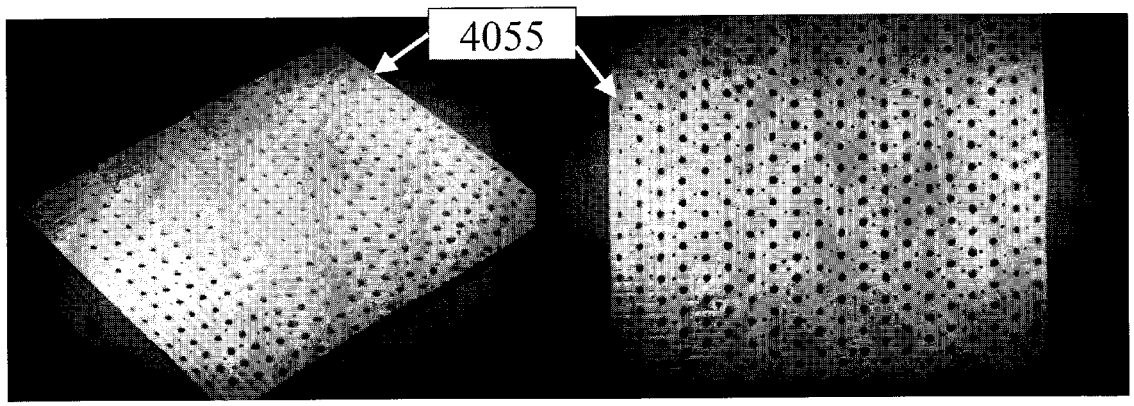
FIGS. 4J-K are photographs of perspective and top views of a fenestrated patterned wound repair scaffold having a combination of larger and smaller fenestrations in accordance with certain embodiments of the present invention.
Figure 4V:
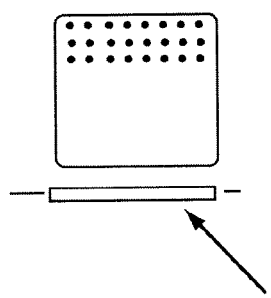
FIGS. 4U-W depicts views of a fenestrated and embossed wound repair scaffold having larger fenestrations and smaller fenestrations with surface embossing intersecting with the smaller fenestrations in accordance with certain embodiments of the present invention.
Figure 4W:
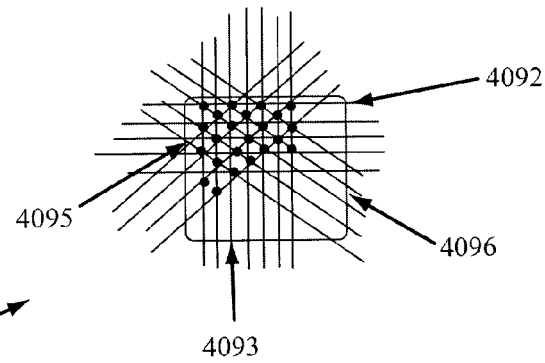
Figure 4U:
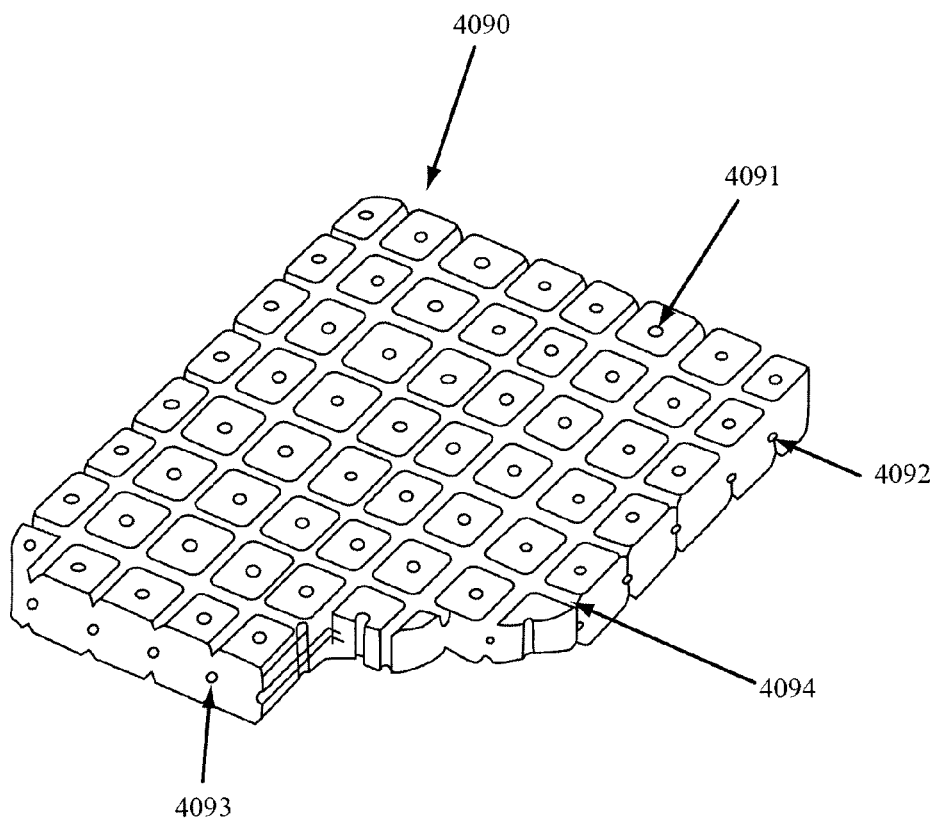

The photographs of FIGS. 4H-T and the drawing of FIGS. 4U-W depict fenestrated collagen wound repair scaffolds 4050, 4055, 4060, 4065, 4070, 4075, 4080, 4085, 4090, and 4095 made from human-derived collagen, including intermediate collagen products containing ethanol. The fenestrated collagen wound repair scaffolds may have an initial thickness of about 1 mm to about 10 mm, 3 mm to about 6 mm, or about 4 mm, and, when compressed and re-lofted by rehydration, may, for example, have a thickness of about 2 mm to about 5 mm for a scaffold having an initial thickness of about 3 mm to about 6 mm. The intermediate collagen product used to prepare the fenestrated collagen wound repair scaffolds may have a collagen dispersion density of about 0.25% to about 4.0%, of about 0.5% to about 0.75%, or of about 0.75 to about 2.0%. The collagen dispersion density may be selected based on its area of implantation or application in order to provide a density most appreciated by populating cells. For example, the density of collagen may facilitate stenting wounds and managing wound closure while controlling contracture and scar formation. Where it is desirable to provide compression resistance and wound stenting, an intermediate collagen product dispersion density of about 4.0% may be employed. In addition, higher dispersion densities of intermediate collagen products may provide a collagen product useful for cartilage repair grafts. In FIGS. 4H-W, the fenestrated collagen wound repair scaffolds include fenestrations having varying sizes, from about 0.56 mm to about 1.51 mm, and may extend in the x, y, and/or z directions. The fenestrations may intersect in order to provide fluid connections between transversely arranged channels. Providing channels across the wound repair scaffold enables biological fluids to move throughout the graft while delivering cells to center areas of the graft from the periphery, e.g., areas generating new cellular growth, and may provide nutrients found in the biological fluids to promote healing and growth. In addition, FIGS. 4N-P and 4U-W depict fenestrated and embossed wound repair scaffolds. Embossing provides surface connections between the fenestrations, which may facilitate fluid integration within the graft, may prevent fluid accumulation under the graft and may further provide for the removal of excessive wound fluid drainage.

FIGS. 4U-W depict an embodiment of a fenestrated and embossed wound repair scaffold 4090, which includes a network of channels linearly extending through the scaffold. Generally axial channel 4091 extends through the depth of scaffold 4090, a first generally transverse channel 4092 extends the width of scaffold 4090, and a second generally transverse channel 4093 extends the length of scaffold 4090. Wound repair scaffold 4090 further includes embossed surface channels 4094 arranged on the top and bottom surfaces, which run along the width and length of the top surfaces to form a matrix composed of a multiplicity of squares. Those of skill in the art will recognize that the surface can also form a multiplicity of any geometric shapes. In FIGS. 4U-W, each of embossed channel intersection points correspond to a generally axial channel 4091. Directly below each embossed channel extending along the width of the surface, at the mid-point of the depth of the wound repair scaffold, is a first generally transverse channel 4092. In addition, directly below each embossed channel extending along the length of the surface, at the mid-point of the depth of the wound repair scaffold is a second generally transverse channel 4093. Thus, according to FIG. 4U, the generally axial channels 4091 at the intersection points of the surface embossed channels intersect with a first and second generally transverse channel 4092 and 4093. However, the generally axial channels arranged in the middle of each square formed by the matrix of surface channels 4094 may provide a fluid passageway through the thickness of the graft, but may not intersect with other channels. However, in certain embodiments another series of generally transverse channels may be arranged within the fenestrated wound repair scaffold.

In certain specific embodiments, the orientation of a channel or a plurality of channels generally can refer to orientation of channels in which at least 50% of the channels are oriented in a single direction and their orientation is along a single direction of alignment, such as a generally first direction or a generally second direction. The orientation of any given channel can deviate from the average axis of alignment and the deviation can be expressed as the angle formed between the alignment axis and orientation of the channel. A deviation angle of 0° exhibits perfect alignment and 90° (or −90°) exhibits orthogonal alignment of the channel with respect to the another axis of alignment. In exemplary embodiments, the standard deviation of the generally axial channel or a generally transverse channel from the average orientation can be an angle selected from between 0° and 1°, between 0° and 3°, between 0° and 5°, between 0° and 10°, between 0° and 20°, or between 0° and 25°.

According to FIG. 4W, in addition to first and second generally transverse channels 4092 and 4093, which run generally transverse relative to each other to form angles including generally 90 degree angles at the intersection points, another set of third and fourth generally transverse channels 4095 and 4096 running transverse relative to each other, but are offset by 45 degrees from the first and second generally transverse channels 4092 and 4093, are provided in scaffold 4090. In the embodiment of FIG. 4W, the generally axial channels 4091 may intersect with third and fourth generally transverse channels 4095 and 4096 in order to form a fluid connection with the periphery of the scaffold in addition to the top and bottom surfaces. Healing of wounds occur from the wound perimeter and closure can be compromised by the size of the wound and open area of the wound. Fenestrations can permit wound fluids to conduct cells toward centrally located open areas of the wound and sustain cells in re-growth, thereby advancing healing and closure more quickly.

Wounds tend to heal from their perimeter and take an extensive amount of time to close, particularly at the central location of the wound. Providing one or multiple sets of intersecting channels or fenestrations within the wound repair scaffold may reduce healing time by promoting cellular migration from the edges of the wound into and/or through the scaffold, thus leading cells towards the center of the scaffold, for example. However, fenestrated wound repair scaffolds may be engineered so that the fenestrations guide fluids and other biologics to a selected area or areas of the wound repair scaffold. When the wound repair scaffold is wet, the fenestrations remain open, and nutrients from the biological fluids, along with living cells, may be distributed throughout the graft via the fenestrations in order to establish cell formations or islands within and around the graft or selected areas of the graft, which facilitates wound closure. In addition, the strength of the wound closure decreases towards central location of the wound. Implanting a wound repair scaffolds may facilitate not only healing in general, but also wound closure strength at the central portion of the wound because growth factors and nutritive materials may migrate from the edges of the scaffold through the open fenestrations to the center of the graft. As a result, fenestrated wound repair scaffolds may shorten healing time and improve wound closure thickness and strength.

According to certain implementations, fenestrated wound repair scaffolds may reduce scarring, improve infection control, and manage fluids. Scarring may be reduced using fenestrated wound repair scaffolds by enabling biological fluids and cells to easily permeate and traverse, e.g., via stenting, the scaffold promotes organized cellular growth. This may avoid contracture and hypertrophy by distributing biological fluids around and through the implant rather than constricting fluid penetration to areas of the wound. The fenestrated wound repair scaffold may also promote or control infection by providing the scaffold over a portion of the wound, which may become occupied by living cells, flooded with blood and wound repair fluids, which may promote re-establishment of continuity at the wound site, and thus promote resistance to infection. In addition, the channels and/or fenestrations provided in the wound repair scaffold may have a desired strength in order to maintain open pathways for biological fluids to pass in and through may thus manage movement of excess of biological fluids that, for example, may accumulate at the wound site in and away from the scaffold.

The fenestrated wound repair scaffold may be used in a variety of applications disclosed herein, and particular applications include grafts for treating dermal wounds, pressure sores, venous stasis wounds, and diabetic ulcers. In addition, the fenestrated wound repair scaffolds may be used in reconstructive applications, such as for scar revisions. According to further implementations, the fenestrated wound repair scaffolds may be coated or formed with antibiotics to prevent or fight infection, vasodilators to widen blood vessels, or angiogenic growth factors in order to activate the formation of new blood vessels.

Figure 14:
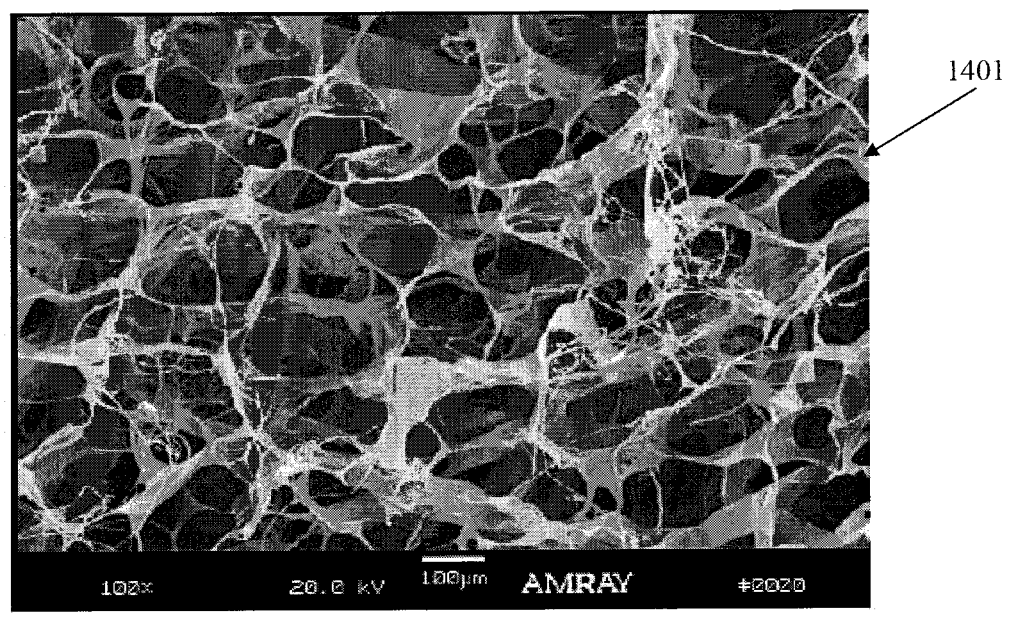
FIG. 14 is a photograph, taken at 100× magnification by scanning electron microscopy, of a collagen product sponge made from human fascia that may be prepared for use as a medical implant in accordance with certain embodiments of the present invention.

A collagen product scaffold 1401 made from human fascia is depicted in FIG. 14, which is a photograph, taken at 100× magnification by scanning electron microscopy. The collagen product scaffold may be prepared according to the scaffold production methods described above, and may be used as a medical implant in accordance with certain embodiments of the present invention. The human-derived collagen product in FIG. 14 results from crystal patterns having a narrow size distribution, which results in a collagen product having a desirable distribution of pore size and pore density.

The sponge-like scaffold 501 of FIG. 5A results from collagen product production methods that do not include a compression step. In contrast, the film-like scaffold 501' of FIG. 5B results from collagen product production methods that include a compression step.

It will be noted that FIG. 5B depicts a wound repair collagen product scaffold 501' in the form of a sheet or film that may be produced in accordance with the methods of FIG. 4A or 4B combined with a compression step. Compressing the collagen product after lyophilizing and cross-linking results in a flexible compressed collagen product. Compressing the collagen product after lyophilizing but before cross-linking results in a slightly less flexible compressed collagen product but with stronger resistance to suture tear-out upon rewetting. Both compressed collagen products are in contrast to a bovine collagen scaffold, which is comparatively stiff or board-like.

Figure 5C:
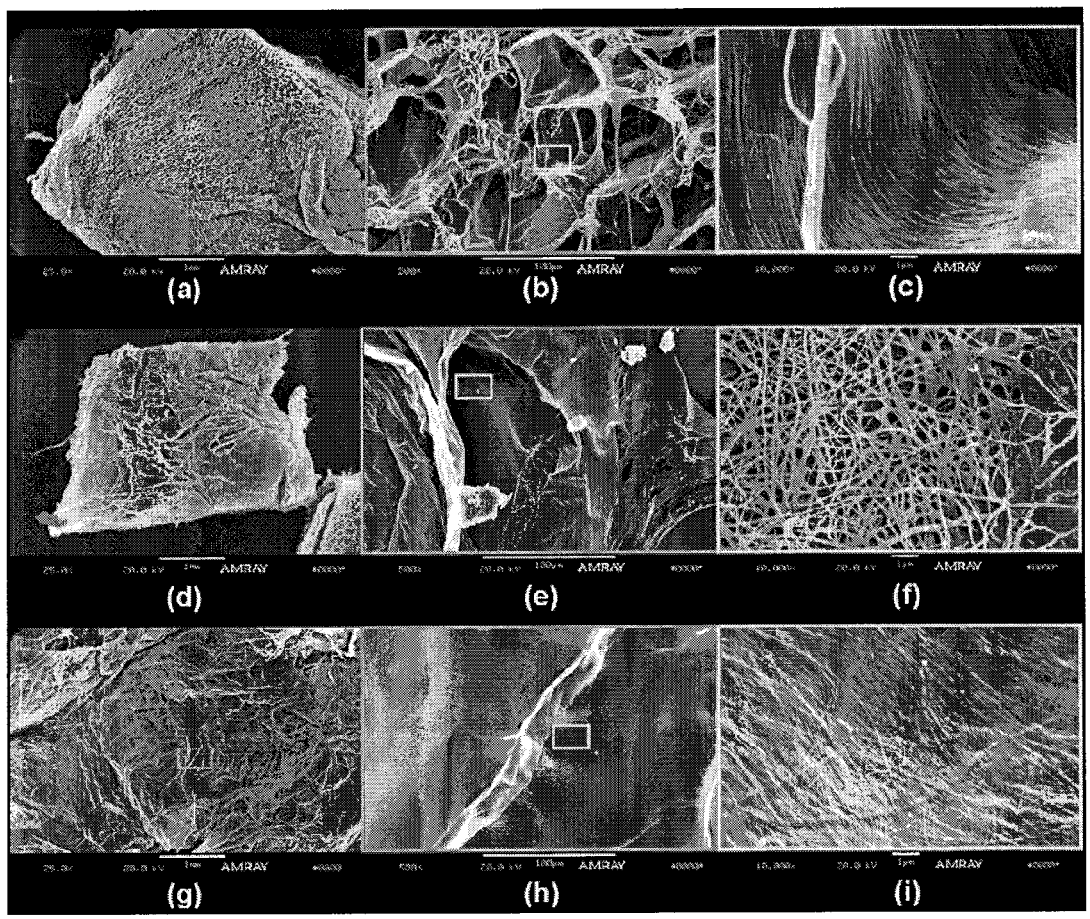
FIGS. 5C(a)-(i) are images of a collagen product scaffold in accordance with certain embodiments of the present invention.

In a further embodiment, collagen product scaffolds are prepared according to the embodiments described above, in which an intermediate collagen product is lyophilized and cross-linked resulting in a collagen grafting material having a macroporous architecture with a nanofibrous micro structure substantially throughout. FIGS. 5C(a)-(i) depict SEM images of an engineered collagen product having an open, porous and three-dimensional scaffold that is formed by an aligned and unoriented nanofiber structure. FIGS. 5C(a)-(c) are images of the top of the collagen product at magnifications of (a) 25×, (b) 500× and (c) 10,000×. The middle row of images, FIGS. 5C(d)-(f), are cross-sectional views of the product at magnifications of (d) 25×, (e) 500× and (f) 10,000×. The bottom row of images, FIGS. 5C(g)-(i), are bottom views of the collagen product at magnifications of (g) 25×, (h) 500× and (i) 10,000×. The nanofiber structure is present throughout substantially the entire scaffold. For example, FIG. 5C(c) illustrates pores lined with aligned nanofibers. FIG. 5C(f) is an image of a portion of the collagen cross-section having unoriented nanofibers. FIG. 5C(i) is an image of a portion of the bottom of the collagen product having both aligned and unoriented nanofibers. The image 5C(c) shows the nano fiber structure, image 5C(f) describes iso-orientation of collagen fiber bundles (precipitated) with interstice open areas and image 5C(i) describes the collagen fiber in dense film like presentation.

Figure 5D:
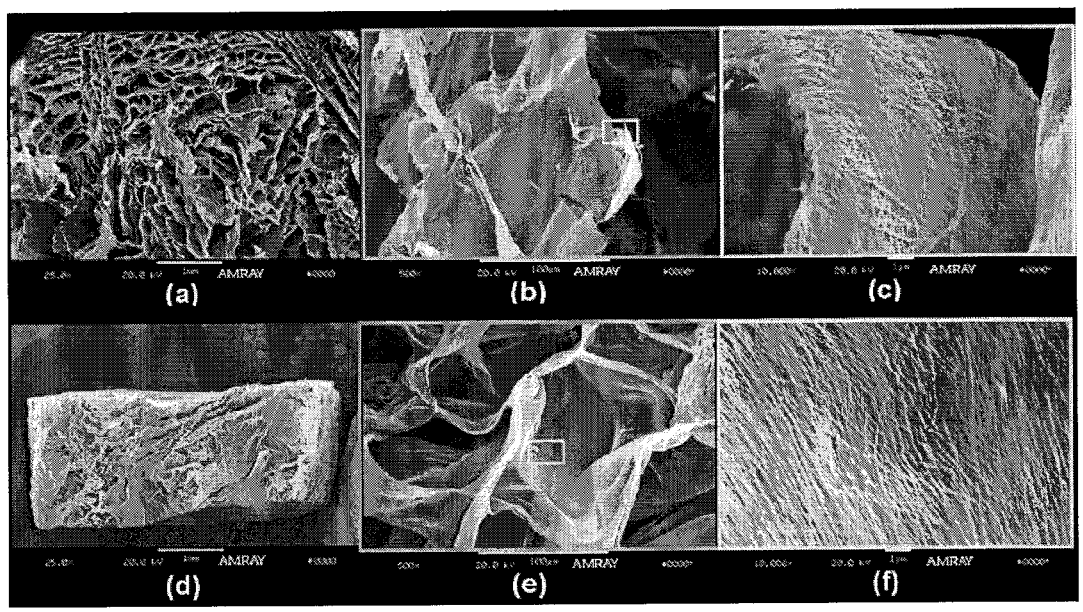
FIGS. 5D(a)-(f) are images of a collagen product scaffold before and after compression in accordance with certain embodiments of the present invention.
Figure 6:
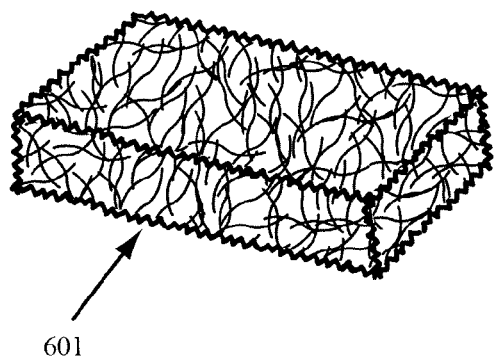
FIG. 6 is an illustration of a wound repair dressing constructed from a human or human-like collagen product in accordance with an embodiment of the present invention.

FIGS. 5D(a)-(f) depict SEM images of another collagen product scaffold before (FIGS. 5D(a)-(c)) and after having been compressed (4000 psi to 0.004" shims 30 s), reconstituted (0.9% saline/5 mins.) and dried (60:70:80:90:100:100% series of 200 proof alcohol/critical point dried (e.g., supercritical $CO_2$)) (FIGS. 5D(d)-(f)). FIGS. 5D(a)-(c) are images of a profile of the collagen product before compression at magnifications of (a) 25×, (b) 500× and (c) 10,000×. FIGS. 5D(d)-(f) are images of the bottom of the product that has been compressed and relofted at magnifications of (d) 25×, (e) 500× and (f) 10,000×. As can be seen from FIGS. 5D(c)-(f), the nanofiber structure is present after reconstitution or relofting of the collagen product, and the microstructure is similar to that of the collagen product of FIGS. 5C(a)-(i). Accordingly, reconstitution (e.g., hydration) does not lead to excessive swelling that would block pores or obstruct nanofibers. Thus, the collagen product scaffold, when implanted, may retain its favorable biological properties even after being pressed and reconstituted. Embodiments provided herein thus recreate three-dimensional scaffolds having a nanofiber structure, which may help increase the rate of cell growth and maintain natural tissue morphology. Additionally, an open pore structure with nanofibers on the open pore structure is favorable to cell growth and supports the growth of blood vessels into the scaffold. Images 5C(d) and (f) depict the open structure of collagen fiber bundles that can be used to produce sheet like form of fiber bundles depicted in image 5D(c). 5D(f) shows oriented fiber bundles that further manage the direction of cellular ingrowth.

When the collagen product sheet or film is to be used as an implant, it is removed from its packaging, if present, and may be wetted or relofted, e.g., by wetting in saline, e.g., about 0.9% saline, so that the film or sheet expands into its original sponge-like shape, e.g., into the collagen product scaffold depicted in FIG. 5A, or into a sponge-like shape that may be thinner compared to its original pre-compressed shape when the collagen product scaffold is compressed before, and in some embodiments after, cross-linking. The rewetted collagen product implant is ready for implantation and may be any or all of flexible, drapeable, capable of forming a seal with adjacent structures, strong and/or resistant to suture pullout.

In addition, a pressed collagen product, provided according to certain embodiments, retains a pressed flat condition when dry, whereas a bovine collagen scaffold does not. Alternatively, a collagen product scaffold may be pressed and implanted in the dried state, and may be reconstituted or rehydrated via body fluids after implantation.

A drapeable scaffold, e.g., a scaffold that is prepared by relofting, may have improved capability to conform to an implant site, e.g., the brain. A scaffold resistant to suture pullout or tear-out provides a collagen product implant that demonstrates an ability to be sutured without buckling or lifting. In some implementations, where relofting results in an implant that is slightly thinner than the original thickness, the collagen product may exhibit improved strength and is more resistant to suture pullout or tear-out. A drapeable and suturable scaffold can provide a gentle, yet comprehensive seal at an implant site.

The sponge-like or film-like wound repair scaffolds and grafts of FIGS. 4D-4W and 5A-D may have various applications and may be used as a dura/meningeal repair dressing, sponge-like or foam-like or otherwise absorbent hemostat, dermal repair dressing, cartilage repair scaffold, cell growth media, and/or substance delivery media, e.g., drugs, nutrients, growth factors, etc. Wound repair matrices may be used in combination with other medical implant structures with or without human-derived or human-like collagen components. Matrices fabricated according to certain implementations may be flexible, tough, soft, drape-like, have a high degree of plasticity, and/or be resistant to suture pullout; and may be useful in applications such as neurosurgery, orthopaedic surgery, laboratory applications, dermatology, and/or plastic surgery.

Example

Comparison of Collagen Scaffolds Based on Starting Collagen Material

Scaffold characteristics may be at least partly dependent on the source of the collagen used to prepare the intermediate collagen product. For purposes of example, bovine tendon is compared to human tendon. A dispersion of about 0.75% bovine collagen derived from bovine tendon is more viscous, e.g., has a thickness of honey, and results in a stiffer sponge compared to a dispersion of about 0.75% human collagen derived from human tendon, which is comparatively thinner (e.g., slightly more viscous than water) and is self-leveling. In another example, bovine fascia is compared to human fascia. A dispersion of about 0.75% bovine collagen derived from bovine fascia is a non-free-flowing highly viscous dispersion that results in a stiffer sponge compared to a dispersion of about 0.75% human collagen product derived from human fascia, which on the other hand, is free-flowing (e.g., nearly water-like) and self-leveling. Each of the human-derived products has a beige color and their dispersions may have a yellow/green color, whereas bovine dispersions and products are relatively white. The resulting human-derived collagen product scaffold has a higher degree of plasticity and elasticity compared to the bovine sponge, which allows the scaffold to generally return to its original shape when manipulated. Further, human-derived collagen product scaffold is flexible and resistant to cracking which allows the scaffold to be bent and twisted without creasing. In addition, the scaffold made from the human collagen product has better draping and handling properties, which allows the scaffold to be wetted and conformed and adhered to an implant area. Moreover, for human-derived collagen products made from tendon compared to fascia, a tendon-sourced collagen product scaffold is stiffer compared to the fascia-sourced collagen product scaffold, but both are more elastic and plastic compared to bovine-derived collagen scaffolds. Although, human-derived fascia and tendon are contemplated as a starting material for producing collagen product scaffolds, intermediate collagen products and other collagen implants may be produced using other human-derived sources, e.g., any type of human-derived collagen. It will be appreciated, however, that bovine-sourced collagen-containing tissue and other non-human collagen-containing tissue may be used as a starting material according to certain aspects of the invention, and the above comparison should not be construed to mean that bovine or non-human-sourced collagen is unsuitable for embodiments of the invention. For example, non-human tissue may be enzymatically treated to remove immunilogically active glycoproteins and recombinant collagen, while retaining non-collagenous proteins that may provide beneficial effects in humans. Accordingly, non-human derived tissue may be processed in a similar or same manner as the methods described above in order to provide an implant that produces no or a low immunogenic response in humans.

Example

Comparison of Collagen Product Scaffolds Based on Intermediate Collagen Product

Collagen product scaffolds have different physical characteristics when formed from intermediate collagen product II, III, and an intermediate collagen product that contains the liquid component of the blended collagen product dispersion, i.e., with any foam removed.

Figure 15:
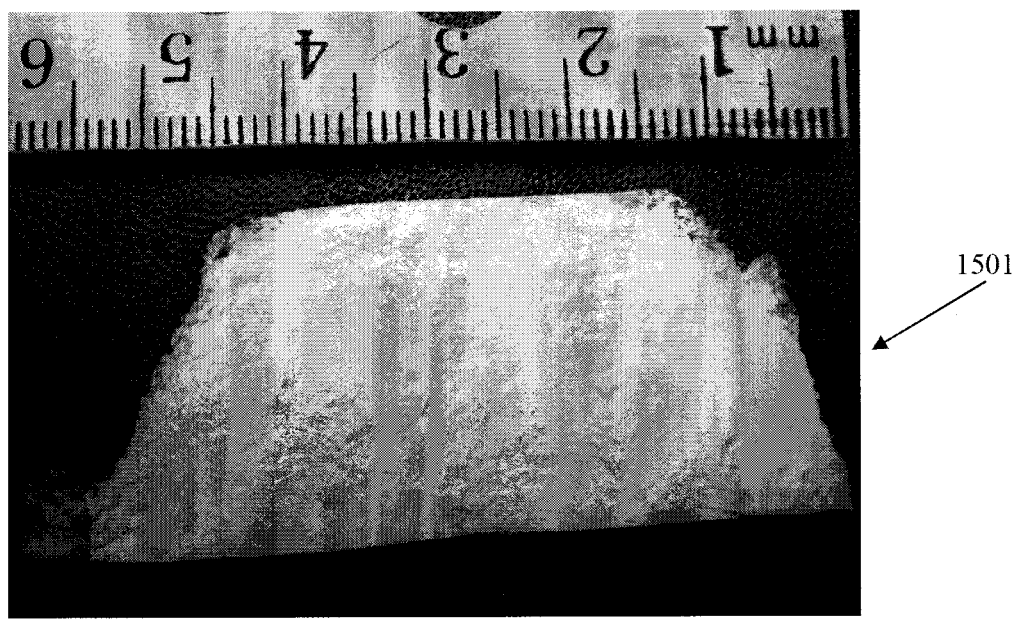
FIG. 15 is a photograph of a human-derived collagen product matrix prepared from intermediate collagen product II made from human fascia that may be prepared for use as a medical implant in accordance with certain embodiments of the present invention.

A collagen product scaffold made from intermediate collagen product II, e.g. a reconstituted collagen product foam layer from human-derived fascia and a leveling agent, is substantial, resists deformation and tearing when handled roughly, but is pliable. FIG. 15 is a photograph of a collagen product scaffold 1501 produced from intermediate collagen product II made from human fascia as a starting material, which may be prepared for use as a medical implant in accordance with certain embodiments of the present invention.

A scaffold produced from intermediate collagen product III, e.g., collagen product from human-derived fascia and a leveling agent, is flexible, firm and has elastic/plastic characteristics that are substantially similar in both the x and y directions. However, the scaffold produced from intermediate collagen product III is not as substantive or strong compared to the scaffold produced from intermediate collagen product II.

A collagen product scaffold produced from a collagen product dispersion without a foam component, e.g., with the foam layer removed, is soft, sensitive to the touch, and easily deformable, not elastic, and tears upon rough handling. Accordingly, the collagen scaffolds formed from the collagen product intermediate II and III exhibits differing physical and mechanical properties.

Characterization of Collagen Scaffolds

Collagen product scaffolds produced with intermediate product III, e.g., with the collagen dispersion and re-liquefied foam component, and subjected to various tests for characterization.

Tensile Test:

Dry collagen product scaffolds formed from human fascia were cut into 12 mm×80 mm samples and rehydrated in 0.9% saline solution for 5 minutes or at least until hydrated prior to testing. Samples were subjected to testing on a MTS® machine at a strain rate of 60 mm/min. The ultimate tensile strength for five samples, along with the average ultimate tensile strength and standard deviation are provided in Table 1.

TABLE 1

| Sample | Ult Stress (MPa) |
|---|---|
| A | 5.951 |
| B | 1.708 |
| C | 2.544 |
| D | 2.208 |
| E | 1.496 |
| Average | 2.782 |
| Std. Dev. | 1.819 |

Suture Retention Test:

Collagen product scaffolds described above were cut into 10 mm×20 mm samples and rehydrated. A 4-0 Ethicon silk thread in a tf-1 tapered needle formed a suture, 3 mm suture bite 20 mm width. A MTS® machine was run at a strain rate of 20 mm/min. The suture strength for five samples, along with the average strength and standard deviation are provided in Table 2.

TABLE 2

| Sample | Strength (N) |
|---|---|
| A | 0.582 |
| B | 0.651 |
| C | 0.546 |
| D | 0.582 |
| E | 0.624 |
| Average | 0.597 |
| Std. Dev. | 0.041 |

Burst Strength Test:

Collagen product scaffolds described above were cut into 100 mm×100 mm samples and rehydrated. A Mullen Burst apparatus was attached to a MTS® machine and a constant strain rate of 305 mm/min. was applied (ASTM 3787). The burst strength for five samples, along with the average burst strength and standard deviation are provided in Table 3.

TABLE 3

| Set | Burst (N) | @ Displacement (mm) | Linear Stiffness (N/mm) |
|---|---|---|---|
| A | 20.7130 | 13.9778 | 2.1687 |
|   | 31.1333 | 16.1899 | 3.0481 |
|   | 30.7907 | 13.9891 | 3.8112 |
|   | 25.9281 | 13.1448 | 3.3830 |
|   | 25.9233 | 15.1670 | 3.2199 |
| B | 34.1159 | 16.1587 | 3.2221 |
|   | 27.4880 | 15.1560 | 2.6919 |
|   | 22.1082 | 14.1627 | 2.2377 |
|   | 37.4927 | 16.1831 | 3.8224 |
|   | 39.6557 | 15.6670 | 4.0538 |
| C | 32.7945 | 15.3310 | 3.8650 |
|   | 25.2914 | 13.9613 | 3.2255 |
|   | 14.1775 | 12.1089 | 1.5695 |
|   | 25.1739 | 14.8091 | 2.9499 |
|   | 21.5813 | 14.6381 | 2.2134 |
| D | 18.8626 | 13.2826 | 2.4716 |
|   | 32.4219 | 16.1484 | 3.2478 |
|   | 20.4316 | 14.2975 | 2.0227 |
|   | 25.1739 | 14.9851 | 2.6338 |
|   | 26.8084 | 13.6325 | 3.1078 |
| Average | 26.9033 | 14.6495 | 2.9483 |
| Std. Dev | 6.4641 | 1.1414 | 0.6849 |

Denaturation Temperature Test:

Collagen product scaffolds described above were cut into 4 mm×4 mm samples and rehydrated for 15 minutes. The samples were placed in an aluminum crucible, sealed and run in a DSC analysis at a temperature increase of 10° C./min. The temperature a which each of the nine samples denatured, along with the average temperature and standard deviation are listed in Table 4.

TABLE 4

| Sample | Temperature (° C.) |
|---|---|
| A | 63.0 |
| B | 62.3 |
| C | 61.5 |
| D | 56.7 |
| E | 56.8 |
| F | 58.2 |
| G | 61.0 |
| H | 56.8 |
| I | 56.8 |
| J | 58.9 |
| K | 56.7 |
| L | 58.1 |
| Avg. ± Std. | 58.9 ± 2.4 |

Figure 16:
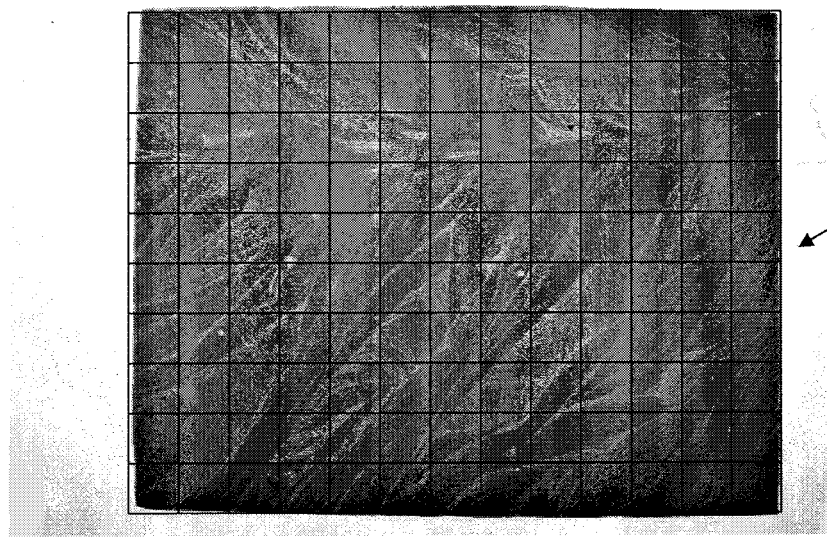
FIG. 16 is a photograph of a human-derived collagen product matrix prepared according to known methods.
Figure 17:
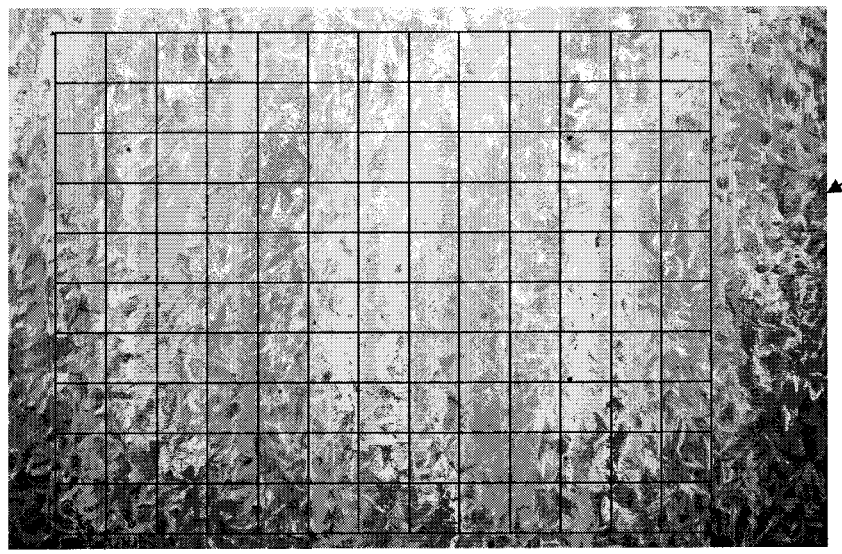
FIG. 17 is a photograph of a collagen product matrix prepared according to certain embodiments of the present invention.
Figures 18A, 18B:
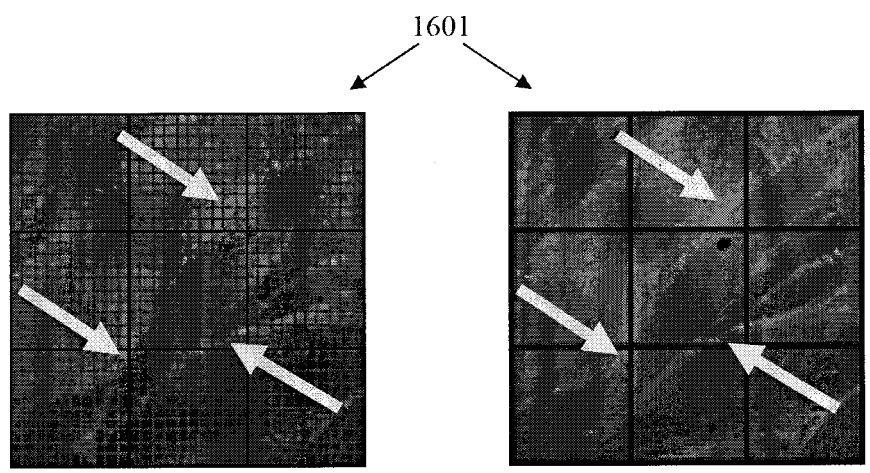
FIGS. 18A-B are photographs of a detailed portion of the collagen product matrix shown in FIG. 16.
Figures 19A, 19B:
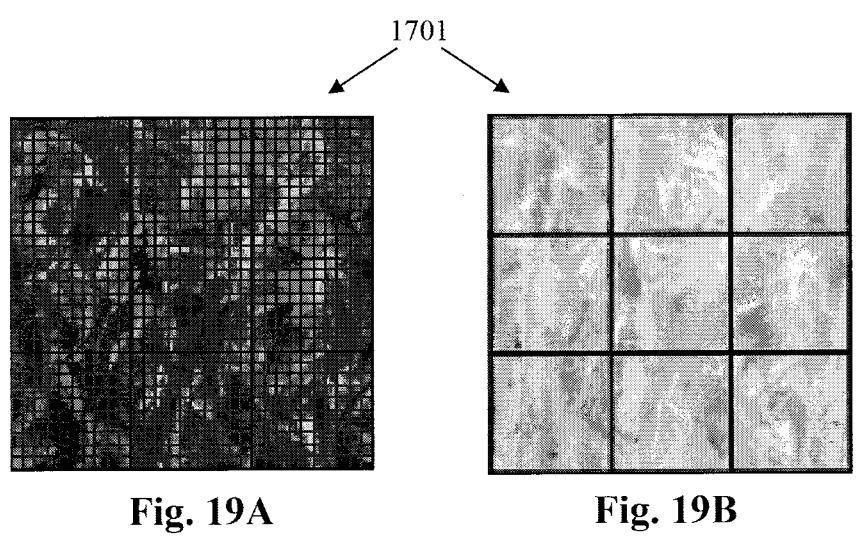
FIGS. 19A-B are photographs of a detailed portion of the collagen product matrix shown in FIG. 17.

Visual Characterization:

Lyophilized collagen product scaffolds produced according to certain embodiments of the present invention were compared to other collagen product scaffolds using stereology. FIG. 16 is a photograph with grid overlay of a 13 cm×10 cm collagen product scaffold produced according to known methods. The typical ice sharding pattern viewable in the collagen product scaffold 1601 of FIG. 16 produces large shards spanning areas over several square centimeters. FIG. 17 is a photograph of a collagen product scaffold 1701 with grid overlay of a 15 cm×11 cm collagen product scaffold produced according to embodiments of the present invention. According to FIG. 17, the ice sharding patterns are comparatively small. FIGS. 18A-B are 3 cm×3 cm areas of the scaffold 1601 of FIG. 16 showing an example large shard outlined by 3 arrows, which spans an area that is approximately 70 mm². FIG. 18B provides a clear image of the large shard with the small grid lines removed. In comparison, FIGS. 19A-B are 3 cm×3 cm areas of the scaffold 1701 of FIG. 17 where each shard is approximately 11 mm². FIG. 19B provides a clear image of the small shards with the small grid lines removed. In view of FIGS. 16-19, lyophilized collagen product scaffolds 1701 produced according to some implementations of the present invention are characterized by small shards when compared to lyophilized collagen product scaffolds 1601 produced by other means. It is believed that small shard patterning provides a stronger, more durable collagen product scaffold and that large shard patterning results in a weaker, less durable collagen product scaffold. Accordingly, collagen products, in particular lyophilized scaffolds, produced according to implementations of the present invention are high strength, durable and biologically compatible collagen product implants. In some implementations (not shown), collagen product scaffolds may be produced according to embodiments of the invention that further include the addition of glycerol to the collagen product suspension, which may affect the crystal size of the finished scaffold.

Scanning Electron Microscope (SEM) Characterization:

Lyophilized collagen product scaffolds produced according to certain embodiments were compressed at 3000 lbs, reconstituted and dried. SEM images of the lyophilized scaffolds 2001 show pore structure on a first surface of the scaffold, e.g., top surface, at a magnification of 50× (FIG. 20A), 100× (FIG. 20B), 250× (FIG. 20C) and 500× (FIG. 20D). SEM images of another lyophilized collagen product scaffold 2101 shows the scaffold structure of another surface of the scaffold, e.g., bottom surface or the scaffold surface that is directly adjacent to the surface it was frozen upon, at a magnification of 25× (FIG. 21A), 50× (FIG. 21B), 100× (FIG. 21C) and 250× (FIG. 21D). From FIGS. 20A-D, the pore structure of the collagen product scaffold 2001 is relatively uniform. Uniformity in pore structure may provide a substantial and pliable implant that resists deformation and tearing when handled roughly.

Collagen Product Matrix/Sling

In further embodiments, the matrix or scaffold produced according to the methods depicted in FIGS. 4A, 4B, U.S. patent application Ser. No. 11/673,972, and variants thereof, may be further processed to alter or add material to the scaffold. For example, according to FIG. 4C, the liquid component is removed to form a matrix from FIG. 4A, and one or more cross-linking cycles (4005, 4006) may be added to the production process that will increase the density of the scaffold.

In addition or alternatively, and according to FIG. 4C, the scaffold may be reinforced (4007) by adding to the scaffold PEEK film, polylactide and polypropylene sutures, bone, metal implants (e.g., steel), any number of bio active polymers, e.g., tyrosine polycarbonates and tyrosine polyarylates, bio active drugs in poly form, and/or other biocompatible materials. Processes for adding reinforcing materials to the matrix may include: lamination, vapor deposition, dispersion, and/or chemical reaction. In addition, the altered collagen product matrix or scaffold may be compressed. Moreover, collagen products may be altered by providing one or more of the above-mentioned materials inside of the collagen product matrix. For example, PEEK film may be provided as a mesh or other reinforcing component and the collagen product matrix may be formed over and around the mesh.

Altered collagen product matrices described above may be used as a repair matrix or sling in applications such as rotator cuff repair, breast reconstruction or augmentation, hernia repair, vaginal wall repair, sphincter repair, meniscus repair, and/or annular repair of the spine. Accordingly, the altered collagen product may be useful in general, orthopaedic, obstetric, gynecological, plastic, and/or urological surgical settings, for example.

Although the intermediate collagen products I-III may be produced according to the above-described methods in which isolated collagen fiber and/or thread base materials are used to produce the intermediate collagen product, e.g., previously recovered dried and dehydrated collagen, intermediate collagen products I-III produced during the collagen recovery process are also contemplated. For example, collagen recovery methods including the methods described in the above-mentioned patent application Ser. No. 11/673,972, filed Feb. 12, 2007, entitled "Methods for Collagen Processing and Products using Processed Collagen," may include a processing step in which a leveling agent, e.g., alcohol or a salt, is blended with the collagen so that the collagen is suspended in a foam and liquid layer. The foam may be recovered and the collagen product therein further processed according various collagen recovery steps in order to prepare collagen and produce intermediate collagen products II and/or III.

Furthermore, intermediate collagen production methods and collagen implant production methods described above may include some or all of the steps in any order. For example, an intermediate collagen product may include the liquid component of the blended collagen dispersion containing a leveling agent and not the foam component. Such an intermediate product may be useful when preparing composite collagen products, for example, that have a collagen product made from only the collagen foam, and a collagen product made only from the collagen dispersion left after the foam is removed. Moreover, although the products described above have associated exemplary applications, other applications for the products are also contemplated. For example, wound repair matrices resembling a sponge or a film may serve as a growth media or substrate (e.g., stem cell growth media).

The above-described structural implants and method of making the implants that include human-derived or human-like collagen products should not be construed as limiting. For example, additional collagen types may be used in addition to or as an alternative to human-derived collagen. In some embodiments, collagen products may be prepared from genetically modified animals in a manner that renders the collagen products non-immunogenic, or that renders collagen products having small amounts of antigenic components. In a particular example, collagen products derived from genetically modified pigs, which have no functional expression of the alpha 1,3 galactosyl transferase gene, may be used as a source of collagen. Furthermore, collagen products may be recovered from bovine, goat, sheep, or any animal genetically modified for use in humans. In another example, animal collagen products that have been enzymatically treated to remove glycoproteins to make the collagen substantially similar to human collagen may be used in accordance with some embodiments. In another example a substantially non-immunogenic collagen-containing soft tissue xenograft may be used as a starting material, and is disclosed in U.S. Pat. No. 6,455,309, issued Sep. 24, 2002, entitled "Proteoglycan-reduced soft tissue xenografts," which is incorporated by reference herein in its entirety. Collagen may also be grown in cell cultures (e.g., recombinant collagen), which may be engineered to possess human or human-like characteristics. In a further example, xenograft placenta may comprise a source of collagen, which may be used as a collagen product implant alone or in combination with collagen derived from humans, e.g., human placenta. Collagen fiber and/or thread base materials sourced from human collagen-containing tissue or human-like or from the above-described genetically modified or otherwise treated collagen used to form the products described are believed to be less likely to produce an immunogenic response when used for implantation into humans, and thus are likely to be accepted at an implant site.

The above-described structural implants should not be construed as limiting. For example, according to certain embodiments, various products having human-derived or human-like collagen product fiber and/or thread base materials may be combined to form a composite of two or more of the above-mentioned products. In one example, a collagen product thread may be combined with a collagen product scaffold/matrix, each which may be produced using the same or a different intermediate collagen product as a starting material. In another example, collagen films may be combined with a collagen product scaffold/matrix by incorporating the film into and/or on the collagen product scaffold/matrix. In a further example, collagen product fibers, threads, fibrils and/or particles may be combined with each other, or may be combined with a collagen film, scaffold, etc. Other products not having human-derived or human-like collagen product fiber and/or thread base materials may also be combined with the various products described herein. Moreover, although the products described above have associated exemplary applications, other applications for the products are also contemplated. For example, wound repair scaffolds resembling a sponge or a collagen product film may serve as a growth media or substrate. In addition, medical implants having human-derived or human-like collagen fiber and/or thread base materials may be formed as a flexible or rigid implant depending on the implant's intended application.

Furthermore, products incorporating human-derived or human-like collagen fiber and/or thread base materials may be designed to include various physical characteristics. For example, structural repair implants having incorporated collagen product fiber and/or thread base materials may be constructed so that the implant is suturable, e.g., where the patch is produced to include suture holes in the non-woven fabric 701 seen in FIG. 7, such that the implant can be fixed at an implant site. In addition, medical implants incorporating human-derived or human-like collagen product fiber and/or thread base materials may be formed as a flexible or rigid implant depending on the implant's intended application. In another example, human-derived or human-like collagen products may be mixed with synthetic collagen or other synthetic biocompatible substances in order to achieve a desired product, physical property or performance. In a particular example, a synthetic, collagen product, or synthetic/collagen product fabric and/or scaffold may be incorporated with a collagen product scaffold, which may be implanted or compressed to yield a low profile material suitable for implantation. In another example, a collagen product is mixed with elastin from any source, or from humans, bovine, and/or porcine sources to yield products having particular strength characteristics. In addition, human-derived or human-like collagen products may be processed into putties or pastes so that the implant may be melted and/or shaped for an appropriate implantation use.

In accordance with some embodiments, other additives, including but not limited to those described below, may be added as a supplement to the human collagen products. It will be appreciated that the amount of additive used will vary depending upon the type of additive, the specific activity of the particular additive preparation employed, and the intended use of the composition. Any of a variety of medically and/or surgically useful optional substances can be added to, or associated with, the collagen product material, at any appropriate stage of the processing.

For example, angiogenesis may be an important contributing factor for the collagen product device in certain applications. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the collagen product to increase angiogenesis. For example, class 3 semaphorins, e.g., SEMA3, controls vascular morphogenesis by inhibiting integrin function in the vascular system, Serini et al., Nature, (July 2003) 424:391-397, and may be included in the collagen product device.

In accordance with other embodiments, collagen product devices may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder as described in U.S. Pat. No. 5,073,373; hydroxyapatite and/or other minerals; xenogenic collagen products, insoluble collagen product derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; antiemetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; BMPs; osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a cell attachment sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmcopeial Convention, Inc., Rockville Md., 2001.

In some embodiments, the agent to be delivered may be adsorbed to or otherwise associated with the human collagen. The agent may be associated with the collagen product through specific or non-specific interactions, covalent or non-covalent interactions, etc. Examples of specific interactions include those between a ligand and a receptor, an epitope and an antibody, etc. Examples of non-specific interactions include hydrophobic interactions, electrostatic interactions, magnetic interactions, dipole interactions, van der Waals interactions, hydrogen bonding, etc. In certain embodiments, the agent may be attached to the collagen product using a linker so that the agent is free to associate with its receptor or site of action in vivo. In other embodiments, the agent may be bound or captured within the collagen product as a result of collagen cross-linking. In certain embodiments, the agent to be delivered may be attached to a chemical compound such as a peptide. In another embodiment, the agent to be delivered may be attached to an antibody, or fragment thereof, that recognizes an epitope found within the collagen. In certain embodiments, at least two bioactive agents may be attached to the collagen product. In other embodiments, at least three bioactive agents may be attached to the collagen product. Sebald et al., PCT/EP00/00637, describes the production of exemplary engineered growth factors that are beneficial for use with the collagen device.

While the present disclosure is written primarily in terms of human tissue and human collagen, it is understood that some methods may be used in any appropriate context with any appropriate material. The present invention is directed to any type of tissue that may be implanted in an allogenic context in any vertebrate species. For example, equine collagen may be processed and used for equine implantation, canine collagen may be processed and used for canine implantation, etc. The use of tissue for implantation from the same species source can provide benefits due to the potential of the natural constituents, unique to the species, providing implantation benefits once implanted. For example, a biochemical response in the implantee recognizing the natural constituents in the implant as acceptable may facilitate biological processes such as cross-linking and integration.

The above description should not be construed as limiting, but merely as exemplifications of, preferred embodiments. Those skilled in the art will envision other modifications within the scope and spirit of the present disclosure.

What is claimed is:

1. A foam-formed human collagen strand material comprising a matrix of reticulated pores, said strand material formed by depositing a dispersed solution of human collagen strands on a template, the reticulated pores having a pore size ranging from greater than 0.6 mm to less than 2.0 mm, wherein the matrix of reticulated pores comprises a plurality of fenestrations oriented in a first direction providing channels configured to conduct fluid and cell movement within and throughout the foam-formed human collagen strand material; said material comprising the matrix of reticulated pores further comprising a surface being embossed to form a surface topography wherein matrices of intersecting embossed surface channels include an axial channel extending between an embossed top surface channel intersection point and an embossed bottom surface channel intersection point.

2. The foam-formed collagen strand material of claim 1, wherein said collagen comprises one or more native human constituents selected from non-collagenous proteins, growth factors, cells, and extracellular matrix.

3. The foam-formed human collagen strand material of claim 1, wherein said foam-formed human collagen strand material makes up at least a portion of a mesh structure.

4. The foam-formed human collagen strand material of claim 1, wherein the strand material makes up at least a portion of a fabric.

5. The foam-formed human collagen strand material of claim 4, wherein the fabric comprises at least one of a woven, knitted, or felted fabric.

6. The foam-formed human collagen strand material of claim 1, wherein the foam-formed collagen strand material comprises at least a portion of a wound repair scaffold, at least a portion of the foam-formed collagen strand material being configured to promote directional movement of biological materials along the length of the strand.

7. The foam-formed human collagen strand material of claim 1, wherein the foam-formed collagen strand material comprises a compressed and twisted strand.

8. The foam-formed human collagen strand material of claim 7, wherein the compressed and twisted strand comprises a cross-sectional diameter of about 0.006" to about 0.009".

9. The foam-formed human collagen strand material of claim 7, wherein the compressed and twisted strand comprises a cross-sectional diameter of about 0.010" to about 0.012".

10. The foam-formed human collagen strand material of claim 7, wherein the compressed and twisted strand makes up at least a portion of a braided cable.

11. The foam-formed human collagen strand material of claim 10, wherein the braided cable further comprises non-collagenous filament or hybrid filaments.

12. The foam-formed human collagen strand material of claim 1, wherein the human collagen is intestinal, placenta, bladder fascia, or tendon tissue.

13. A medical implant comprising a foam-formed human collagen strand material according to claim 1.

14. The medical implant of claim 13, wherein said implant comprises a braided cable.

15. The medical implant of claim 13, wherein said implant comprises a woven patch.

16. The foam-formed human collagen strand material of claim 1, wherein the matrix of reticulated pores further comprises a plurality of fenestrations oriented in a second direction and extending from a first lateral surface to a second lateral surface of the foam-formed collagen strand material, the plurality of fenestrations oriented in the first direction extending from a top surface of the foam-formed collagen strand material to a bottom surface of the foam-formed collagen strand material.

17. The foam-formed human collagen strand material of claim 16, wherein the plurality of fenestrations oriented in the first direction and the plurality of fenestrations oriented in the second direction intersect.

18. The foam-formed human collagen strand material of claim 16, wherein the plurality of fenestrations oriented in the first direction and the plurality of fenestrations oriented in the second direction overlap without intersecting.

19. The foam-formed human collagen strand material of claim 16, wherein the surface being embossed to form a surface topography is configured for facilitating fluid and cell movement to the plurality of fenestrations oriented in the first direction and the plurality of fenestrations oriented in the second direction.

* * * * *